United States Patent
Wondka et al.

(10) Patent No.: US 8,567,399 B2
(45) Date of Patent: Oct. 29, 2013

(54) METHODS AND DEVICES FOR PROVIDING INSPIRATORY AND EXPIRATORY FLOW RELIEF DURING VENTILATION THERAPY

(75) Inventors: Anthony Wondka, Thousand Oaks, CA (US); Gregory Kapust, San Ramon, CA (US)

(73) Assignee: Breathe Technologies, Inc., Irvine, CA (US)

( * ) Notice: Subject to any disclaimer, the term of this patent is extended or adjusted under 35 U.S.C. 154(b) by 1403 days.

(21) Appl. No.: 12/239,723

(22) Filed: Sep. 26, 2008

(65) Prior Publication Data

US 2009/0151724 A1    Jun. 18, 2009

Related U.S. Application Data

(60) Provisional application No. 60/960,370, filed on Sep. 26, 2007.

(51) Int. Cl.
*A61M 16/00* (2006.01)

(52) U.S. Cl.
USPC ............ 128/204.23; 128/200.24; 128/204.18; 128/204.21

(58) Field of Classification Search
USPC ............ 128/200.24, 200.26, 204.18, 204.21, 128/204.23, 205.25, 206.21, 206.29, 128/207.14, 207.18; 604/256, 523, 604/533–539, 284, 93.01, 95.02, 118, 264, 604/258, 94.01
See application file for complete search history.

(56) References Cited

U.S. PATENT DOCUMENTS

| | | | |
|---|---|---|---|
| 50,641 A | 10/1865 | Stone | |
| 428,592 A | 5/1890 | Chapman | |
| 697,181 A | 4/1902 | Smith | |
| 718,785 A | 1/1903 | McNary | |
| 853,439 A | 5/1907 | Clark | |
| 859,156 A | 7/1907 | Warnken | |

(Continued)

FOREIGN PATENT DOCUMENTS

| | | |
|---|---|---|
| DE | 19626924 | 1/1998 |
| DE | 29902267 U1 | 7/1999 |

(Continued)

OTHER PUBLICATIONS

In the U.S. Patent and Trademark Office, Supplemental Notice of Allowance dated in re: U.S. Appl. No. 10/771,803, dated Dec. 2, 2008, 2 pages.

(Continued)

*Primary Examiner* — Annette Dixon
(74) *Attorney, Agent, or Firm* — Stetina Brunda Garred & Brucker

(57) ABSTRACT

Respiratory support and/or controlled mechanical ventilation of a patient are provided. A ventilation apparatus may include a ventilator, a transtracheal prosthesis, and a respiratory relief device. The transtracheal prostheses and ventilation catheter may be arranged such that the patient can breathe freely through the upper airway and/or the tracheal prostheses. Respiratory sensors may measure a breathing rate, lung pressure, airway pressure, or a combination thereof. Pulses of gas may be provided to the patient through the ventilation catheter during inspiration. The pulses may have a first volume while the patient breathes normal and a second volume when the sensors detect a cessation of breathing or reduction in breathing volume. The second volume may be provided at 1-5 times the normal breathing rate, with a volume 25-500% times the first volume, or both.

12 Claims, 16 Drawing Sheets

(56) References Cited

U.S. PATENT DOCUMENTS

| | | |
|---|---|---|
| 909,002 A | 1/1909 | Lambert |
| 1,125,542 A | 1/1915 | Humphries |
| 1,129,619 A | 2/1915 | Zapf |
| 1,331,297 A | 2/1920 | Walker |
| 2,178,800 A | 11/1939 | Lombard |
| 2,259,817 A | 10/1941 | Hawkins |
| 2,552,595 A | 5/1951 | Seeler |
| 2,663,297 A | 12/1953 | Turnberg |
| 2,693,800 A | 11/1954 | Caldwell |
| 2,735,432 A | 2/1956 | Hudson |
| 2,792,000 A | 5/1957 | Richardson |
| 2,843,122 A | 7/1958 | Hudson |
| 2,859,748 A | 11/1958 | Hudson |
| 2,931,358 A | 4/1960 | Sheridan |
| 2,947,938 A | 8/1960 | Bennett |
| 3,172,407 A | 3/1965 | Von Pechmann |
| 3,267,935 A | 8/1966 | Andreasen et al. |
| 3,319,627 A | 5/1967 | Windsor |
| 3,357,424 A | 12/1967 | Schreiber |
| 3,357,427 A | 12/1967 | Wittke et al. |
| 3,357,428 A | 12/1967 | Carlson |
| 3,437,274 A | 4/1969 | Apri |
| 3,460,533 A | 8/1969 | Riú Plá |
| 3,493,703 A | 2/1970 | Finan |
| 3,513,844 A | 5/1970 | Smith |
| 3,610,247 A | 10/1971 | Jackson |
| 3,625,206 A | 12/1971 | Charnley |
| 3,625,207 A | 12/1971 | Agnew |
| 3,631,438 A | 12/1971 | Lewin |
| 3,643,660 A | 2/1972 | Hudson et al. |
| 3,657,740 A | 4/1972 | Cialone |
| 3,682,171 A | 8/1972 | Dali et al. |
| 3,721,233 A | 3/1973 | Montgomery et al. |
| 3,726,275 A | 4/1973 | Jackson et al. |
| 3,727,606 A | 4/1973 | Sielaff |
| 3,733,008 A | 5/1973 | Churchill et al. |
| 3,741,208 A | 6/1973 | Jonsson et al. |
| 3,754,552 A | 8/1973 | King |
| 3,794,026 A | 2/1974 | Jacobs |
| 3,794,072 A | 2/1974 | Diedrich et al. |
| 3,802,431 A | 4/1974 | Farr |
| 3,831,596 A | 8/1974 | Cavallo |
| 3,881,480 A | 5/1975 | Lafourcade |
| 3,896,800 A | 7/1975 | Cibulka |
| 3,903,881 A | 9/1975 | Weigl |
| 3,905,362 A | 9/1975 | Eyrick et al. |
| 3,949,749 A | 4/1976 | Stewart |
| 3,951,143 A | 4/1976 | Kitrilakis et al. |
| 3,961,627 A | 6/1976 | Ernst et al. |
| 3,972,327 A | 8/1976 | Ernst et al. |
| 3,985,131 A | 10/1976 | Buck et al. |
| 3,991,790 A | 11/1976 | Russell |
| 4,003,377 A | 1/1977 | Dahl |
| 4,036,253 A | 7/1977 | Fegan et al. |
| 4,054,133 A | 10/1977 | Myers |
| 4,067,328 A | 1/1978 | Manley |
| 4,106,505 A | 8/1978 | Salter et al. |
| 4,146,885 A | 3/1979 | Lawson, Jr. |
| 4,206,754 A | 6/1980 | Cox et al. |
| 4,211,086 A | 7/1980 | Leonard et al. |
| 4,216,769 A | 8/1980 | Grimes |
| 4,231,363 A | 11/1980 | Grimes |
| 4,231,365 A | 11/1980 | Scarberry |
| 4,256,101 A | 3/1981 | Ellestad |
| 4,261,355 A | 4/1981 | Glazener |
| 4,263,908 A | 4/1981 | Mizerak |
| 4,265,237 A | 5/1981 | Schwanbom et al. |
| 4,266,540 A | 5/1981 | Panzik et al. |
| 4,273,124 A | 6/1981 | Zimmerman |
| 4,274,162 A | 6/1981 | Joy et al. |
| 4,278,082 A | 7/1981 | Blackmer |
| 4,282,869 A | 8/1981 | Zidulka |
| 4,306,567 A | 12/1981 | Krasner |
| 4,323,064 A | 4/1982 | Hoenig et al. |
| 4,354,488 A | 10/1982 | Bartos |
| 4,365,636 A | 12/1982 | Barker |
| 4,367,735 A | 1/1983 | Dali |
| 4,377,162 A | 3/1983 | Staver |
| 4,393,869 A | 7/1983 | Boyarsky et al. |
| 4,406,283 A | 9/1983 | Bir |
| 4,411,267 A | 10/1983 | Heyman |
| 4,413,514 A | 11/1983 | Bowman |
| 4,421,113 A | 12/1983 | Gedeon et al. |
| 4,422,456 A | 12/1983 | Tiep |
| 4,449,523 A | 5/1984 | Szachowicz et al. |
| 4,454,880 A | 6/1984 | Muto et al. |
| 4,462,398 A | 7/1984 | Durkan et al. |
| 4,469,097 A | 9/1984 | Kelman |
| 4,481,944 A | 11/1984 | Bunnell |
| 4,488,548 A | 12/1984 | Agdanowski |
| 4,495,946 A | 1/1985 | Lemer |
| 4,506,666 A | 3/1985 | Durkan |
| 4,506,667 A | 3/1985 | Ansite |
| 4,519,387 A | 5/1985 | Durkan et al. |
| 4,520,812 A | 6/1985 | Freitag et al. |
| 4,527,557 A | 7/1985 | DeVries et al. |
| 4,535,766 A | 8/1985 | Baum |
| 4,537,188 A | 8/1985 | Phuc |
| 4,539,984 A | 9/1985 | Kiszel et al. |
| 4,548,590 A | 10/1985 | Green |
| 4,559,940 A | 12/1985 | McGinnis |
| 4,570,631 A | 2/1986 | Durkan |
| 4,571,741 A | 2/1986 | Guillaumot |
| 4,584,996 A | 4/1986 | Blum |
| 4,590,951 A | 5/1986 | O'Connor |
| 4,592,349 A | 6/1986 | Bird |
| 4,621,632 A | 11/1986 | Bartels et al. |
| 4,630,606 A | 12/1986 | Weerda et al. |
| 4,630,614 A | 12/1986 | Atlas |
| 4,644,947 A | 2/1987 | Whitwam et al. |
| 4,648,395 A | 3/1987 | Sato et al. |
| 4,648,398 A | 3/1987 | Agdanowski et al. |
| 4,658,832 A | 4/1987 | Brugnoli |
| 4,660,555 A | 4/1987 | Payton |
| 4,682,591 A | 7/1987 | Jones |
| 4,684,398 A | 8/1987 | Dunbar et al. |
| 4,686,974 A | 8/1987 | Sato et al. |
| 4,686,975 A | 8/1987 | Naimon et al. |
| 4,688,961 A | 8/1987 | Shioda et al. |
| 4,705,034 A | 11/1987 | Perkins |
| 4,744,356 A | 5/1988 | Greenwood |
| 4,747,403 A | 5/1988 | Gluck et al. |
| 4,753,233 A | 6/1988 | Grimes |
| 4,773,411 A | 9/1988 | Downs |
| 4,776,333 A | 10/1988 | Miyamae |
| 4,782,832 A | 11/1988 | Trimble et al. |
| 4,784,130 A | 11/1988 | Kenyon et al. |
| 4,803,981 A | 2/1989 | Vickery |
| 4,807,616 A | 2/1989 | Adahan |
| 4,807,617 A | 2/1989 | Nesti |
| 4,808,160 A | 2/1989 | Timmons et al. |
| 4,813,431 A | 3/1989 | Brown |
| 4,817,897 A | 4/1989 | Kreusel |
| 4,818,320 A | 4/1989 | Weichselbaum |
| 4,823,788 A | 4/1989 | Smith et al. |
| 4,825,859 A | 5/1989 | Lambert |
| 4,827,922 A | 5/1989 | Champain et al. |
| 4,832,014 A | 5/1989 | Perkins |
| 4,838,255 A | 6/1989 | Lambert |
| 4,841,953 A | 6/1989 | Dodrill |
| 4,848,333 A | 7/1989 | Waite |
| 4,850,350 A | 7/1989 | Jackson |
| 4,865,586 A | 9/1989 | Hedberg |
| 4,869,718 A | 9/1989 | Brader |
| 4,899,740 A | 2/1990 | Napolitano |
| 4,905,688 A | 3/1990 | Vicenzi et al. |
| 4,915,103 A | 4/1990 | Visveshwara et al. |
| 4,915,105 A | 4/1990 | Lee |
| 4,919,128 A | 4/1990 | Kopala et al. |
| 4,919,132 A | 4/1990 | Miser |
| 4,938,212 A | 7/1990 | Snook et al. |
| 4,944,310 A | 7/1990 | Sullivan |
| 4,967,743 A | 11/1990 | Lambert |
| 4,971,049 A | 11/1990 | Rotariu et al. |

(56) References Cited

U.S. PATENT DOCUMENTS

| | | |
|---|---|---|
| 4,982,735 A | 1/1991 | Yagata et al. |
| 4,986,269 A | 1/1991 | Hakkinen |
| 4,989,599 A | 2/1991 | Carter |
| 4,990,157 A | 2/1991 | Roberts et al. |
| 5,000,175 A | 3/1991 | Pue |
| 5,002,050 A | 3/1991 | McGinnis |
| 5,005,570 A | 4/1991 | Perkins |
| 5,018,519 A | 5/1991 | Brown |
| 5,022,394 A | 6/1991 | Chmielinski |
| 5,024,219 A | 6/1991 | Dietz |
| 5,025,805 A | 6/1991 | Nutter |
| 5,038,771 A | 8/1991 | Dietz |
| 5,042,478 A | 8/1991 | Kopala et al. |
| 5,046,491 A | 9/1991 | Derrick |
| 5,046,492 A | 9/1991 | Stackhouse et al. |
| 5,048,515 A | 9/1991 | Sanso |
| 5,048,516 A | 9/1991 | Soderberg |
| 5,052,400 A | 10/1991 | Dietz |
| 5,054,484 A | 10/1991 | Hebeler, Jr. |
| 5,058,580 A | 10/1991 | Hazard |
| 5,074,299 A | 12/1991 | Dietz |
| 5,076,267 A | 12/1991 | Pasternack |
| 5,090,408 A | 2/1992 | Spofford et al. |
| 5,097,827 A | 3/1992 | Izumi |
| 5,099,836 A | 3/1992 | Rowland et al. |
| 5,099,837 A | 3/1992 | Russel, Sr. et al. |
| 5,101,820 A | 4/1992 | Christopher |
| 5,103,815 A | 4/1992 | Siegel et al. |
| 5,105,807 A | 4/1992 | Kahn et al. |
| 5,107,830 A | 4/1992 | Younes |
| 5,107,831 A | 4/1992 | Halpern et al. |
| 5,113,857 A | 5/1992 | Dickerman et al. |
| 5,117,818 A | 6/1992 | Palfy |
| 5,117,819 A | 6/1992 | Servidio et al. |
| 5,127,400 A | 7/1992 | DeVries et al. |
| 5,134,995 A | 8/1992 | Gruenke et al. |
| 5,134,996 A | 8/1992 | Bell |
| 5,140,045 A | 8/1992 | Askanazi et al. |
| 5,148,802 A | 9/1992 | Sanders et al. |
| 5,161,525 A | 11/1992 | Kimm et al. |
| 5,165,397 A | 11/1992 | Arp |
| 5,181,509 A | 1/1993 | Spofford et al. |
| 5,184,610 A | 2/1993 | Marten et al. |
| 5,186,167 A | 2/1993 | Kolobow |
| 5,193,532 A | 3/1993 | Moa et al. |
| 5,193,533 A | 3/1993 | Body et al. |
| 5,199,424 A | 4/1993 | Sullivan et al. |
| 5,211,170 A | 5/1993 | Press |
| 5,217,008 A | 6/1993 | Lindholm |
| 5,233,978 A | 8/1993 | Callaway |
| 5,233,979 A | 8/1993 | Strickland |
| 5,239,994 A | 8/1993 | Atkins |
| 5,239,995 A | 8/1993 | Estes et al. |
| 5,243,972 A | 9/1993 | Huang |
| 5,245,995 A | 9/1993 | Sullivan et al. |
| 5,255,675 A | 10/1993 | Kolobow |
| 5,258,027 A | 11/1993 | Berghaus |
| 5,269,296 A | 12/1993 | Landis |
| 5,271,388 A | 12/1993 | Whitwam et al. |
| 5,271,391 A | 12/1993 | Graves |
| 5,275,159 A | 1/1994 | Griebel |
| 5,279,288 A | 1/1994 | Christopher |
| 5,287,852 A | 2/1994 | Arkinstall |
| 5,303,698 A | 4/1994 | Tobia et al. |
| 5,303,700 A | 4/1994 | Weismann et al. |
| 5,318,019 A | 6/1994 | Celaya |
| 5,331,995 A | 7/1994 | Westfall et al. |
| 5,335,656 A | 8/1994 | Bowe et al. |
| 5,339,809 A | 8/1994 | Beck, Jr. et al. |
| 5,349,946 A | 9/1994 | McComb |
| 5,368,017 A | 11/1994 | Sorenson et al. |
| 5,370,112 A | 12/1994 | Perkins |
| 5,373,842 A | 12/1994 | Olsson et al. |
| 5,375,593 A | 12/1994 | Press |
| 5,388,575 A | 2/1995 | Taube |
| 5,394,870 A | 3/1995 | Johansson |
| 5,398,676 A | 3/1995 | Press et al. |
| 5,398,682 A | 3/1995 | Lynn |
| 5,400,778 A | 3/1995 | Jonson et al. |
| 5,419,314 A | 5/1995 | Christopher |
| 5,438,979 A | 8/1995 | Johnson, Jr. et al. |
| 5,438,980 A | 8/1995 | Phillips |
| 5,443,075 A | 8/1995 | Holscher |
| 5,460,174 A | 10/1995 | Chang |
| 5,460,613 A | 10/1995 | Ulrich et al. |
| 5,474,062 A | 12/1995 | DeVires et al. |
| 5,477,852 A | 12/1995 | Landis et al. |
| 5,485,850 A | 1/1996 | Dietz |
| 5,490,502 A | 2/1996 | Rapoport et al. |
| 5,503,146 A | 4/1996 | Froehlich et al. |
| 5,503,497 A | 4/1996 | Dudley et al. |
| 5,507,282 A | 4/1996 | Younes |
| 5,509,409 A | 4/1996 | Weatherholt |
| 5,513,628 A | 5/1996 | Coles et al. |
| 5,513,631 A | 5/1996 | McWilliams |
| 5,513,635 A | 5/1996 | Bedi |
| 5,522,382 A | 6/1996 | Sullivan et al. |
| 5,526,806 A | 6/1996 | Sansoni |
| 5,529,060 A | 6/1996 | Salmon et al. |
| 5,533,506 A | 7/1996 | Wood |
| 5,535,738 A | 7/1996 | Estes et al. |
| 5,537,997 A | 7/1996 | Mechlenburg et al. |
| 5,538,002 A | 7/1996 | Boussignac et al. |
| 5,542,415 A | 8/1996 | Brody |
| 5,546,935 A | 8/1996 | Champeau |
| 5,549,106 A | 8/1996 | Gruenke et al. |
| 5,551,419 A | 9/1996 | Froehlich et al. |
| 5,558,086 A | 9/1996 | Smith et al. |
| 5,564,416 A | 10/1996 | Jones |
| 5,575,282 A | 11/1996 | Knoch et al. |
| 5,582,164 A | 12/1996 | Sanders |
| 5,593,143 A | 1/1997 | Ferrarin |
| 5,595,174 A | 1/1997 | Gwaltney |
| 5,598,837 A | 2/1997 | Sirianne, Jr. et al. |
| 5,598,840 A | 2/1997 | Iund et al. |
| 5,603,315 A | 2/1997 | Sasso, Jr. |
| 5,605,148 A | 2/1997 | Jones |
| 5,626,131 A | 5/1997 | Chua et al. |
| 5,632,269 A | 5/1997 | Zdrojkowski |
| 5,636,630 A | 6/1997 | Miller et al. |
| 5,645,053 A | 7/1997 | Remmers et al. |
| 5,645,054 A | 7/1997 | Cotner et al. |
| 5,647,351 A | 7/1997 | Weismann et al. |
| 5,669,377 A | 9/1997 | Fenn |
| 5,669,380 A | 9/1997 | Garry et al. |
| 5,676,132 A | 10/1997 | Tillotson et al. |
| 5,676,135 A | 10/1997 | McClean |
| 5,682,878 A | 11/1997 | Ogden |
| 5,682,881 A | 11/1997 | Winthrop et al. |
| 5,687,713 A | 11/1997 | Bahr et al. |
| 5,687,714 A | 11/1997 | Kolobow et al. |
| 5,687,715 A | 11/1997 | Landis et al. |
| 5,690,097 A | 11/1997 | Howard et al. |
| 5,692,497 A | 12/1997 | Schnitzer et al. |
| 5,697,364 A | 12/1997 | Chua et al. |
| 5,704,345 A | 1/1998 | Berthon-Jones |
| 5,711,296 A | 1/1998 | Kolobow |
| 5,715,812 A | 2/1998 | Deighan et al. |
| 5,715,815 A | 2/1998 | Lorenzen et al. |
| 5,720,278 A | 2/1998 | Lachmann et al. |
| 5,735,268 A | 4/1998 | Chua et al. |
| 5,735,272 A | 4/1998 | Dillon et al. |
| 5,740,796 A | 4/1998 | Skog |
| 5,752,511 A | 5/1998 | Simmons et al. |
| 5,762,638 A | 6/1998 | Shikani et al. |
| 5,791,337 A | 8/1998 | Coles et al. |
| 5,819,723 A | 10/1998 | Joseph |
| 5,826,579 A | 10/1998 | Remmers et al. |
| 5,845,636 A | 12/1998 | Gruenke et al. |
| 5,865,173 A | 2/1999 | Froehlich |
| 5,865,174 A | 2/1999 | Kloeppel |
| 5,868,133 A * | 2/1999 | DeVries et al. .......... 128/204.21 |
| 5,881,723 A | 3/1999 | Wallace et al. |
| 5,904,648 A | 5/1999 | Arndt et al. |

(56) References Cited

U.S. PATENT DOCUMENTS

| | | |
|---|---|---|
| 5,906,204 A | 5/1999 | Beran et al. |
| 5,911,756 A | 6/1999 | Debry |
| 5,915,379 A | 6/1999 | Wallace et al. |
| 5,915,381 A | 6/1999 | Nord |
| 5,918,597 A | 7/1999 | Jones et al. |
| 5,921,238 A | 7/1999 | Bourdon |
| 5,921,942 A | 7/1999 | Remmers et al. |
| 5,921,952 A | 7/1999 | Desmond, III et al. |
| 5,927,276 A | 7/1999 | Rodriguez |
| 5,928,189 A | 7/1999 | Phillips et al. |
| 5,931,159 A * | 8/1999 | Suzuki et al. ............ 128/204.18 |
| 5,931,160 A | 8/1999 | Gilmore et al. |
| 5,931,162 A | 8/1999 | Christian |
| 5,937,853 A | 8/1999 | Strom |
| 5,937,855 A | 8/1999 | Zdrojkowski et al. |
| 5,938,118 A | 8/1999 | Cooper |
| 5,954,050 A | 9/1999 | Christopher |
| 5,957,136 A | 9/1999 | Magidson et al. |
| 5,964,223 A | 10/1999 | Baran |
| 5,975,077 A | 11/1999 | Hofstetter et al. |
| 5,975,081 A | 11/1999 | Hood et al. |
| 5,979,440 A | 11/1999 | Honkonen et al. |
| 5,989,193 A | 11/1999 | Sullivan |
| 6,000,396 A | 12/1999 | Melker et al. |
| 6,019,101 A | 2/2000 | Cotner et al. |
| 6,039,696 A | 3/2000 | Bell |
| 6,050,260 A | 4/2000 | Daniell et al. |
| 6,076,519 A | 6/2000 | Johnson |
| 6,085,747 A | 7/2000 | Axe et al. |
| 6,091,973 A | 7/2000 | Colla et al. |
| 6,093,169 A | 7/2000 | Cardoso |
| 6,105,575 A | 8/2000 | Estes et al. |
| 6,109,264 A | 8/2000 | Sauer |
| 6,112,746 A | 9/2000 | Kwok et al. |
| 6,119,694 A | 9/2000 | Correa et al. |
| 6,120,460 A | 9/2000 | Abreu |
| 6,123,668 A | 9/2000 | Abreu |
| 6,131,571 A | 10/2000 | Lampotang et al. |
| 6,135,970 A | 10/2000 | Kadhiresan et al. |
| 6,152,132 A | 11/2000 | Psaros |
| 6,152,134 A | 11/2000 | Webber et al. |
| 6,158,432 A | 12/2000 | Biondi et al. |
| 6,192,883 B1 | 2/2001 | Miller, Jr. |
| 6,203,502 B1 | 3/2001 | Hilgendorf et al. |
| 6,213,119 B1 | 4/2001 | Brydon et al. |
| 6,213,955 B1 | 4/2001 | Karakasoglu et al. |
| 6,220,244 B1 | 4/2001 | McLaughlin |
| 6,224,560 B1 | 5/2001 | Gazula et al. |
| 6,227,200 B1 | 5/2001 | Crump et al. |
| 6,247,470 B1 | 6/2001 | Ketchedjian |
| 6,269,811 B1 | 8/2001 | Duff et al. |
| 6,269,812 B1 | 8/2001 | Wallace et al. |
| 6,273,859 B1 | 8/2001 | Remmers et al. |
| 6,279,574 B1 * | 8/2001 | Richardson et al. ...... 128/204.18 |
| 6,286,508 B1 | 9/2001 | Remmers et al. |
| D449,376 S | 10/2001 | McDonald et al. |
| D449,883 S | 10/2001 | McDonald et al. |
| 6,298,850 B1 | 10/2001 | Argraves |
| 6,305,374 B1 | 10/2001 | Zdrojkowski et al. |
| 6,314,957 B1 | 11/2001 | Boissin et al. |
| 6,315,739 B1 | 11/2001 | Merilainen et al. |
| D451,598 S | 12/2001 | McDonald et al. |
| 6,328,038 B1 | 12/2001 | Kessler et al. |
| 6,328,753 B1 | 12/2001 | Zammit |
| 6,332,463 B1 | 12/2001 | Farrugia et al. |
| 6,345,619 B1 | 2/2002 | Finn |
| 6,357,438 B1 | 3/2002 | Hansen |
| 6,357,440 B1 | 3/2002 | Hansen et al. |
| 6,360,741 B2 | 3/2002 | Truschel |
| 6,360,745 B1 | 3/2002 | Wallace et al. |
| 6,363,933 B1 | 4/2002 | Berthon-Jones |
| 6,367,474 B1 | 4/2002 | Berthon-Jones et al. |
| 6,369,838 B1 | 4/2002 | Wallace et al. |
| 6,371,114 B1 | 4/2002 | Schmidt et al. |
| 6,378,520 B1 | 4/2002 | Davenport |
| 6,390,091 B1 | 5/2002 | Banner et al. |
| 6,394,088 B1 | 5/2002 | Frye et al. |
| 6,398,739 B1 | 6/2002 | Sullivan et al. |
| 6,418,928 B1 | 7/2002 | Bordewick et al. |
| 6,422,240 B1 | 7/2002 | Levitsky et al. |
| 6,423,001 B1 | 7/2002 | Abreu |
| 6,427,690 B1 | 8/2002 | McCombs et al. |
| 6,431,172 B1 | 8/2002 | Bordewick |
| 6,439,228 B1 | 8/2002 | Hete et al. |
| 6,439,229 B1 | 8/2002 | Du et al. |
| 6,439,234 B1 | 8/2002 | Curti et al. |
| 6,439,235 B1 | 8/2002 | Larquet et al. |
| 6,450,164 B1 | 9/2002 | Banner et al. |
| 6,450,166 B1 | 9/2002 | McDonald et al. |
| 6,457,472 B1 | 10/2002 | Schwartz et al. |
| 6,467,477 B1 | 10/2002 | Frank et al. |
| 6,478,026 B1 | 11/2002 | Wood |
| 6,494,202 B2 | 12/2002 | Farmer |
| 6,494,206 B1 | 12/2002 | Bergamaschi et al. |
| 6,505,623 B1 | 1/2003 | Hansen |
| 6,505,624 B1 | 1/2003 | Campbell, Sr. |
| 6,516,801 B2 | 2/2003 | Boussignac |
| 6,520,176 B1 | 2/2003 | Dubois et al. |
| 6,520,183 B2 | 2/2003 | Amar |
| 6,530,373 B1 | 3/2003 | Patron et al. |
| 6,532,958 B1 | 3/2003 | Buan et al. |
| 6,532,960 B1 | 3/2003 | Yurko |
| 6,536,432 B2 | 3/2003 | Truschel |
| 6,536,436 B1 | 3/2003 | McGlothen |
| 6,550,478 B2 | 4/2003 | Remmers et al. |
| 6,553,992 B1 | 4/2003 | Berthon-Jones et al. |
| 6,561,188 B1 | 5/2003 | Ellis |
| 6,561,193 B1 | 5/2003 | Noble |
| 6,564,797 B1 | 5/2003 | Mechlenburg et al. |
| 6,564,800 B1 | 5/2003 | Olivares |
| 6,568,391 B1 | 5/2003 | Tatarek et al. |
| 6,571,794 B1 | 6/2003 | Hansen |
| 6,571,796 B2 | 6/2003 | Banner et al. |
| 6,571,798 B1 | 6/2003 | Thornton |
| 6,575,159 B1 | 6/2003 | Frye et al. |
| 6,575,944 B1 | 6/2003 | McNary et al. |
| 6,584,973 B1 | 7/2003 | Biondi et al. |
| 6,588,422 B1 | 7/2003 | Berthon-Jones et al. |
| 6,588,423 B1 | 7/2003 | Sinderby |
| 6,591,834 B1 | 7/2003 | Colla et al. |
| 6,591,835 B1 | 7/2003 | Blanch |
| 6,595,207 B1 | 7/2003 | McDonald et al. |
| 6,595,215 B2 | 7/2003 | Wood |
| 6,609,517 B1 | 8/2003 | Estes et al. |
| 6,622,726 B1 | 9/2003 | Du |
| 6,626,174 B1 | 9/2003 | Genger et al. |
| 6,626,175 B2 | 9/2003 | Jafari et al. |
| 6,629,525 B2 | 10/2003 | Hill et al. |
| 6,629,527 B1 | 10/2003 | Estes et al. |
| 6,629,529 B2 | 10/2003 | Arnott |
| 6,631,713 B1 * | 10/2003 | Christopher ............ 128/200.21 |
| 6,631,919 B1 | 10/2003 | West et al. |
| 6,634,356 B1 | 10/2003 | O'Dea et al. |
| 6,635,021 B1 | 10/2003 | Sullivan et al. |
| 6,640,806 B2 | 11/2003 | Yurko |
| 6,644,305 B2 | 11/2003 | MacRae et al. |
| 6,644,311 B1 | 11/2003 | Truitt et al. |
| 6,644,315 B2 | 11/2003 | Ziaee |
| 6,651,653 B1 | 11/2003 | Honkonen et al. |
| 6,651,656 B2 | 11/2003 | Demers et al. |
| 6,651,658 B1 | 11/2003 | Hill et al. |
| 6,655,382 B1 | 12/2003 | Kolobow |
| 6,655,385 B1 | 12/2003 | Curti et al. |
| 6,666,208 B1 | 12/2003 | Schumacher et al. |
| 6,668,828 B1 | 12/2003 | Figley et al. |
| 6,668,829 B2 | 12/2003 | Biondi et al. |
| 6,669,712 B1 | 12/2003 | Cardoso |
| 6,675,796 B2 | 1/2004 | McDonald |
| 6,675,801 B2 | 1/2004 | Wallace et al. |
| 6,679,265 B2 | 1/2004 | Strickland et al. |
| 6,681,764 B1 | 1/2004 | Honkonen et al. |
| 6,684,883 B1 | 2/2004 | Burns |
| 6,691,702 B2 | 2/2004 | Appel et al. |
| 6,691,707 B1 | 2/2004 | Gunaratnam et al. |

(56) References Cited

U.S. PATENT DOCUMENTS

| | | |
|---|---|---|
| 6,694,973 B1 | 2/2004 | Dunhao et al. |
| 6,694,978 B1 | 2/2004 | Bennarsten |
| 6,698,423 B1 | 3/2004 | Honkonen et al. |
| 6,705,314 B1 | 3/2004 | O'Dea |
| 6,705,315 B2 | 3/2004 | Sullivan et al. |
| 6,722,360 B2 | 4/2004 | Doshi |
| 6,722,362 B2 | 4/2004 | Hete et al. |
| 6,742,517 B1 | 6/2004 | Frye et al. |
| 6,745,768 B2 | 6/2004 | Colla et al. |
| 6,752,150 B1 | 6/2004 | Remmers et al. |
| 6,752,151 B2 | 6/2004 | Hill |
| 6,752,152 B2 | 6/2004 | Gale et al. |
| 6,755,193 B2 | 6/2004 | Berthon-Jones et al. |
| 6,758,217 B1 | 7/2004 | Younes |
| 6,761,172 B2 | 7/2004 | Boussignac et al. |
| 6,763,832 B1 | 7/2004 | Kirsch et al. |
| 6,769,432 B1 | 8/2004 | Keifer |
| 6,776,162 B2 | 8/2004 | Wood |
| 6,776,163 B2 | 8/2004 | Dougill et al. |
| 6,789,539 B2 | 9/2004 | Martinez |
| 6,796,305 B1 | 9/2004 | Banner et al. |
| 6,799,575 B1 | 10/2004 | Carter |
| 6,805,126 B2 | 10/2004 | Dutkiewicz |
| 6,807,966 B2 | 10/2004 | Wright |
| 6,807,967 B2 | 10/2004 | Wood |
| 6,810,876 B2 | 11/2004 | Berthon-Jones |
| 6,814,073 B2 | 11/2004 | Wickham |
| 6,814,077 B1 | 11/2004 | Eistert |
| 6,823,866 B2 * | 11/2004 | Jafari et al. ............ 128/204.21 |
| 6,827,340 B2 | 12/2004 | Austin et al. |
| 6,837,238 B2 | 1/2005 | McDonald |
| 6,840,240 B1 | 1/2005 | Berthon-Jones et al. |
| 6,843,247 B2 | 1/2005 | Frye et al. |
| 6,848,446 B2 | 2/2005 | Noble |
| 6,854,462 B2 | 2/2005 | Berthon-Jones et al. |
| 6,863,069 B2 | 3/2005 | Wood |
| 6,866,041 B2 | 3/2005 | Hardy, Jr. et al. |
| 6,877,511 B2 | 4/2005 | DeVries et al. |
| 6,880,556 B2 | 4/2005 | Uchiyama et al. |
| 6,910,480 B1 | 6/2005 | Berthon-Jones |
| 6,910,482 B2 | 6/2005 | Bliss et al. |
| 6,910,510 B2 | 6/2005 | Gale et al. |
| 6,913,601 B2 | 7/2005 | St. Goar et al. |
| 6,915,803 B2 | 7/2005 | Berthon-Jones et al. |
| 6,920,875 B1 | 7/2005 | Hill et al. |
| 6,920,877 B2 | 7/2005 | Remmers et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,938,620 B2 | 9/2005 | Payne, Jr. |
| 6,941,950 B2 | 9/2005 | Wilson et al. |
| 6,948,497 B2 | 9/2005 | Zdrojkowski et al. |
| 6,951,217 B2 | 10/2005 | Berthon-Jones |
| 6,971,382 B1 | 12/2005 | Corso |
| 6,986,353 B2 | 1/2006 | Wright |
| 6,994,089 B2 | 2/2006 | Wood |
| 6,997,177 B2 | 2/2006 | Wood |
| 6,997,881 B2 | 2/2006 | Green et al. |
| 7,000,612 B2 | 2/2006 | Jafari et al. |
| 7,004,170 B1 | 2/2006 | Gillstrom |
| 7,007,692 B2 | 3/2006 | Aylsworth et al. |
| 7,011,091 B2 | 3/2006 | Hill et al. |
| 7,013,892 B2 | 3/2006 | Estes et al. |
| 7,013,898 B2 | 3/2006 | Rashad et al. |
| 7,017,574 B2 | 3/2006 | Biondi et al. |
| 7,017,575 B2 | 3/2006 | Yagi et al. |
| 7,024,945 B2 | 4/2006 | Wallace |
| 7,036,504 B2 | 5/2006 | Wallace et al. |
| 7,044,129 B1 | 5/2006 | Truschel et al. |
| 7,047,969 B2 | 5/2006 | Noble |
| 7,047,974 B2 | 5/2006 | Strickland et al. |
| 7,051,735 B2 | 5/2006 | Mechlenburg et al. |
| 7,055,522 B2 | 6/2006 | Berthon-Jones |
| 7,059,328 B2 | 6/2006 | Wood |
| 7,066,173 B2 | 6/2006 | Banner et al. |
| 7,066,178 B2 | 6/2006 | Gunaratnam et al. |
| 7,077,132 B2 | 7/2006 | Berthon-Jones |
| 7,077,133 B2 | 7/2006 | Yagi et al. |
| 7,080,645 B2 | 7/2006 | Genger et al. |
| 7,080,646 B2 | 7/2006 | Wiesmann et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,121,277 B2 | 10/2006 | Strom |
| 7,128,578 B2 | 10/2006 | Lampotang et al. |
| 7,152,598 B2 | 12/2006 | Morris et al. |
| 7,152,604 B2 | 12/2006 | Hickle et al. |
| 7,156,090 B2 | 1/2007 | Nomori |
| 7,156,097 B2 | 1/2007 | Cardoso |
| 7,162,296 B2 | 1/2007 | Leonhardt et al. |
| 7,168,429 B2 | 1/2007 | Matthews et al. |
| 7,188,621 B2 | 3/2007 | DeVries et al. |
| 7,188,624 B2 | 3/2007 | Wood |
| 7,195,016 B2 | 3/2007 | Loyd et al. |
| 7,195,018 B1 | 3/2007 | Goldstein |
| 7,201,169 B2 | 4/2007 | Wilkie et al. |
| 7,201,269 B2 | 4/2007 | Buscher et al. |
| D542,912 S | 5/2007 | Gunaratnam et al. |
| 7,222,623 B2 | 5/2007 | DeVries et al. |
| 7,225,811 B2 | 6/2007 | Ruiz et al. |
| 7,234,465 B2 | 6/2007 | Wood |
| 7,237,205 B2 | 6/2007 | Sarel |
| 7,246,620 B2 | 7/2007 | Conroy, Jr. |
| D549,323 S | 8/2007 | Kwok et al. |
| 7,255,103 B2 | 8/2007 | Bassin |
| 7,255,107 B1 | 8/2007 | Gomez |
| 7,267,122 B2 | 9/2007 | Hill |
| 7,267,123 B2 | 9/2007 | Aylsworth et al. |
| 7,270,126 B2 | 9/2007 | Wallace et al. |
| 7,270,128 B2 | 9/2007 | Berthon-Jones et al. |
| 7,296,569 B2 | 11/2007 | Frye et al. |
| 7,296,573 B2 | 11/2007 | Estes et al. |
| D557,802 S | 12/2007 | Miceli, Jr. et al. |
| 7,302,950 B2 | 12/2007 | Berthon-Jones et al. |
| 7,305,987 B2 | 12/2007 | Scholler et al. |
| 7,318,437 B2 | 1/2008 | Gunaratnam et al. |
| 7,320,321 B2 | 1/2008 | Pranger et al. |
| 7,328,703 B1 | 2/2008 | Tiep |
| 7,353,826 B2 | 4/2008 | Sleeper et al. |
| 7,367,337 B2 | 5/2008 | Berthon-Jones et al. |
| 7,370,652 B2 | 5/2008 | Matula, Jr. et al. |
| 7,373,939 B1 | 5/2008 | DuBois et al. |
| 7,406,966 B2 | 8/2008 | Wondka |
| 7,418,965 B2 | 9/2008 | Fukunaga et al. |
| 7,422,015 B2 | 9/2008 | Delisle et al. |
| 7,431,035 B2 | 10/2008 | Mizuta et al. |
| 7,451,762 B2 | 11/2008 | Chua et al. |
| 7,455,717 B2 | 11/2008 | Sprinkle |
| 7,461,656 B2 | 12/2008 | Gunaratnam et al. |
| 7,468,040 B2 | 12/2008 | Hartley et al. |
| 7,469,697 B2 | 12/2008 | Lee et al. |
| 7,472,702 B2 | 1/2009 | Beck et al. |
| 7,478,641 B2 | 1/2009 | Rousselet |
| 7,481,219 B2 | 1/2009 | Lewis et al. |
| 7,481,221 B2 | 1/2009 | Kullik et al. |
| 7,487,774 B2 | 2/2009 | Acker |
| 7,487,778 B2 | 2/2009 | Freitag |
| 7,490,605 B2 | 2/2009 | Frye et al. |
| D588,258 S | 3/2009 | Judson et al. |
| D589,139 S | 3/2009 | Guney et al. |
| 7,500,482 B2 | 3/2009 | Biederman |
| 7,509,957 B2 | 3/2009 | Duquette et al. |
| D591,419 S | 4/2009 | Chandran et al. |
| 7,533,670 B1 | 5/2009 | Freitag et al. |
| 7,556,038 B2 | 7/2009 | Kirby et al. |
| 7,559,327 B2 | 7/2009 | Hernandez |
| 7,562,657 B2 | 7/2009 | Blanch et al. |
| 7,562,659 B2 | 7/2009 | Matarasso |
| 7,578,294 B2 | 8/2009 | Pierro et al. |
| 7,588,033 B2 | 9/2009 | Wondka |
| 7,591,265 B2 | 9/2009 | Lee et al. |
| 7,631,642 B2 | 12/2009 | Freitag et al. |
| 7,640,934 B2 | 1/2010 | Zollinger et al. |
| 7,658,189 B2 | 2/2010 | Davidson et al. |

(56) References Cited

U.S. PATENT DOCUMENTS

| | | |
|---|---|---|
| D614,288 S | 4/2010 | Judson et al. |
| 7,721,733 B2 | 5/2010 | Hughes et al. |
| 7,721,736 B2 | 5/2010 | Urias et al. |
| 7,740,013 B2 | 6/2010 | Ishizaki et al. |
| 7,743,770 B2 | 6/2010 | Curti et al. |
| 7,762,253 B2 | 7/2010 | Acker et al. |
| 7,766,009 B2 | 8/2010 | Frye et al. |
| 7,787,946 B2 | 8/2010 | Stahmann et al. |
| 7,814,906 B2 | 10/2010 | Moretti |
| 7,819,120 B2 | 10/2010 | Taylor et al. |
| D626,646 S | 11/2010 | Lubke et al. |
| D627,059 S | 11/2010 | Wood et al. |
| 7,832,400 B2 | 11/2010 | Curti et al. |
| 7,837,761 B2 | 11/2010 | Bliss et al. |
| 7,841,343 B2 | 11/2010 | Deane et al. |
| 7,845,350 B1 | 12/2010 | Kayyali et al. |
| 7,849,854 B2 | 12/2010 | DeVries et al. |
| 7,856,982 B2 | 12/2010 | Matula, Jr. et al. |
| 7,866,318 B2 | 1/2011 | Bassin |
| 7,874,290 B2 | 1/2011 | Chalvignac |
| 7,874,291 B2 | 1/2011 | Ging et al. |
| 7,874,293 B2 | 1/2011 | Gunaratnam et al. |
| 7,878,980 B2 | 2/2011 | Ricciardelli |
| 7,882,834 B2 | 2/2011 | Gradon et al. |
| 7,886,740 B2 | 2/2011 | Thomas et al. |
| 7,891,353 B2 | 2/2011 | Chalvignac |
| 7,891,357 B2 | 2/2011 | Carron et al. |
| 7,896,958 B2 | 3/2011 | Sermet et al. |
| 7,900,627 B2 | 3/2011 | Aylsworth et al. |
| 7,900,628 B2 | 3/2011 | Matula, Jr. et al. |
| 7,900,635 B2 | 3/2011 | Gunaratnam et al. |
| 7,901,361 B2 | 3/2011 | Rapoport et al. |
| 7,905,231 B2 | 3/2011 | Chalvignac |
| 7,913,691 B2 | 3/2011 | Farrugia |
| 7,914,459 B2 | 3/2011 | Green et al. |
| 7,918,226 B2 | 4/2011 | Acker et al. |
| 7,926,486 B2 | 4/2011 | Childers |
| 7,926,487 B2 | 4/2011 | Drew et al. |
| 7,931,023 B2 | 4/2011 | Berthon-Jones et al. |
| 7,934,499 B2 | 5/2011 | Berthon-Jones |
| 7,938,114 B2 | 5/2011 | Matthews et al. |
| 7,942,150 B2 | 5/2011 | Guney et al. |
| 7,942,380 B2 | 5/2011 | Bertinetti et al. |
| 7,958,892 B2 | 6/2011 | Kwok et al. |
| 7,975,694 B2 | 7/2011 | Ho |
| 7,980,245 B2 | 7/2011 | Rice et al. |
| 7,987,847 B2 | 8/2011 | Wickham et al. |
| 7,987,850 B2 | 8/2011 | Zollinger et al. |
| 7,987,851 B2 | 8/2011 | Blom et al. |
| 7,992,557 B2 | 8/2011 | Nadjafizadeh et al. |
| 7,997,270 B2 | 8/2011 | Meier |
| 7,997,271 B2 | 8/2011 | Hickle et al. |
| 7,997,272 B2 | 8/2011 | Isaza |
| 8,001,967 B2 | 8/2011 | Wallace et al. |
| D645,557 S | 9/2011 | Scheiner et al. |
| 8,011,365 B2 | 9/2011 | Douglas et al. |
| 8,011,366 B2 | 9/2011 | Knepper |
| 8,015,971 B2 | 9/2011 | Kwok |
| 8,015,974 B2 | 9/2011 | Christopher et al. |
| 8,020,558 B2 | 9/2011 | Christopher et al. |
| 8,025,052 B2 | 9/2011 | Matthews et al. |
| RE42,843 E | 10/2011 | Strickland et al. |
| 8,042,535 B2 | 10/2011 | Kenyon et al. |
| 8,042,537 B2 | 10/2011 | Mechlenburg et al. |
| 8,042,539 B2 | 10/2011 | Chandran et al. |
| 8,042,546 B2 | 10/2011 | Gunaratnam et al. |
| 8,061,354 B2 | 11/2011 | Schneider et al. |
| 8,066,004 B2 | 11/2011 | Morris et al. |
| 2001/0035185 A1 | 11/2001 | Christopher |
| 2001/0035186 A1 | 11/2001 | Hill |
| 2001/0042548 A1 | 11/2001 | Boussignac |
| 2002/0014241 A1 | 2/2002 | Gradon et al. |
| 2002/0017300 A1 | 2/2002 | Hickle et al. |
| 2002/0020930 A1 | 2/2002 | Austin et al. |
| 2002/0026941 A1 | 3/2002 | Biondi et al. |
| 2002/0043264 A1 | 4/2002 | Wickham |
| 2002/0046751 A1 | 4/2002 | MacRae et al. |
| 2002/0046755 A1 | 4/2002 | De Voss |
| 2002/0046756 A1 | 4/2002 | Laizzo et al. |
| 2002/0053346 A1 | 5/2002 | Curti et al. |
| 2002/0055685 A1 | 5/2002 | Levitsky et al. |
| 2002/0059935 A1 | 5/2002 | Wood |
| 2002/0066452 A1 | 6/2002 | Kessler et al. |
| 2002/0078957 A1 | 6/2002 | Remmers et al. |
| 2002/0092527 A1 | 7/2002 | Wood |
| 2002/0112730 A1 | 8/2002 | Dutkiewicz |
| 2002/0153010 A1 | 10/2002 | Rozenberg et al. |
| 2002/0157673 A1 | 10/2002 | Kessler et al. |
| 2002/0159323 A1 | 10/2002 | Makabe et al. |
| 2002/0179090 A1 | 12/2002 | Boussignac |
| 2003/0000522 A1 | 1/2003 | Lynn et al. |
| 2003/0047185 A1 | 3/2003 | Olsen et al. |
| 2003/0069489 A1 | 4/2003 | Abreu |
| 2003/0079749 A1 | 5/2003 | Strickland et al. |
| 2003/0094178 A1 | 5/2003 | McAuley et al. |
| 2003/0111081 A1 | 6/2003 | Gupta |
| 2003/0116163 A1 | 6/2003 | Wood |
| 2003/0121519 A1 | 7/2003 | Estes et al. |
| 2003/0145852 A1 | 8/2003 | Schmidt et al. |
| 2003/0145853 A1 | 8/2003 | Muellner |
| 2003/0145856 A1 | 8/2003 | Zdrojkowski et al. |
| 2003/0150455 A1 | 8/2003 | Bliss et al. |
| 2003/0159696 A1 | 8/2003 | Boussignac et al. |
| 2003/0159697 A1 | 8/2003 | Wallace |
| 2003/0168067 A1 | 9/2003 | Dougill et al. |
| 2003/0213488 A1 | 11/2003 | Remmers et al. |
| 2003/0221687 A1 | 12/2003 | Kaigler |
| 2003/0230308 A1 | 12/2003 | Linden |
| 2004/0020493 A1 | 2/2004 | Wood |
| 2004/0025881 A1 | 2/2004 | Gunaratnam et al. |
| 2004/0035431 A1 | 2/2004 | Wright |
| 2004/0040560 A1 | 3/2004 | Euliano et al. |
| 2004/0050387 A1 | 3/2004 | Younes |
| 2004/0074494 A1 | 4/2004 | Frater |
| 2004/0159323 A1 | 8/2004 | Schmidt et al. |
| 2004/0206352 A1 | 10/2004 | Conroy |
| 2004/0221848 A1 | 11/2004 | Hill |
| 2004/0221854 A1 | 11/2004 | Hete et al. |
| 2004/0226566 A1 | 11/2004 | Gunaratnam et al. |
| 2004/0231674 A1 | 11/2004 | Tanaka |
| 2004/0237963 A1 | 12/2004 | Berthon-Jones |
| 2004/0254501 A1 | 12/2004 | Mault |
| 2004/0255943 A1 | 12/2004 | Morris et al. |
| 2005/0005938 A1 | 1/2005 | Berthon-Jones et al. |
| 2005/0010125 A1 | 1/2005 | Joy et al. |
| 2005/0011524 A1 | 1/2005 | Thomlinson et al. |
| 2005/0016534 A1 | 1/2005 | Ost |
| 2005/0033247 A1 | 2/2005 | Thompson |
| 2005/0034724 A1 | 2/2005 | O'Dea |
| 2005/0061322 A1 | 3/2005 | Freitag |
| 2005/0061326 A1 | 3/2005 | Payne |
| 2005/0072430 A1 | 4/2005 | Djupesland |
| 2005/0081849 A1 | 4/2005 | Warren |
| 2005/0087190 A1 | 4/2005 | Jafari et al. |
| 2005/0098179 A1 | 5/2005 | Burton et al. |
| 2005/0103343 A1 | 5/2005 | Gosweiler |
| 2005/0121033 A1 | 6/2005 | Starr et al. |
| 2005/0121037 A1 | 6/2005 | Wood |
| 2005/0121038 A1 | 6/2005 | Christopher |
| 2005/0150498 A1 | 7/2005 | McDonald |
| 2005/0161049 A1 | 7/2005 | Wright |
| 2005/0166924 A1 | 8/2005 | Thomas et al. |
| 2005/0199242 A1 | 9/2005 | Matula et al. |
| 2005/0205096 A1 | 9/2005 | Matula et al. |
| 2005/0247308 A1 | 11/2005 | Frye et al. |
| 2005/0257793 A1 | 11/2005 | Tatsumoto |
| 2005/0274381 A1 | 12/2005 | Deane et al. |
| 2006/0005834 A1 | 1/2006 | Aylsworth et al. |
| 2006/0005842 A1 | 1/2006 | Rashad et al. |
| 2006/0011199 A1 | 1/2006 | Rashad et al. |
| 2006/0027234 A1 | 2/2006 | Gradon et al. |
| 2006/0048781 A1 | 3/2006 | Nawata |
| 2006/0054169 A1 | 3/2006 | Han et al. |
| 2006/0070625 A1 | 4/2006 | Ayappa et al. |

(56) References Cited

U.S. PATENT DOCUMENTS

| | | |
|---|---|---|
| 2006/0076017 A1* | 4/2006 | Walker et al. ............ 128/205.24 |
| 2006/0079799 A1 | 4/2006 | Green et al. |
| 2006/0096596 A1 | 5/2006 | Occhialini et al. |
| 2006/0107958 A1 | 5/2006 | Sleeper |
| 2006/0112959 A1 | 6/2006 | Mechlenburg et al. |
| 2006/0124131 A1 | 6/2006 | Chandran et al. |
| 2006/0124134 A1 | 6/2006 | Wood |
| 2006/0137690 A1 | 6/2006 | Gunaratnam et al. |
| 2006/0144396 A1 | 7/2006 | DeVries et al. |
| 2006/0149144 A1 | 7/2006 | Lynn et al. |
| 2006/0150972 A1 | 7/2006 | Mizuta et al. |
| 2006/0150973 A1 | 7/2006 | Chalvignac |
| 2006/0150982 A1 | 7/2006 | Wood |
| 2006/0174877 A1 | 8/2006 | Jagger et al. |
| 2006/0180149 A1 | 8/2006 | Matarasso |
| 2006/0185669 A1 | 8/2006 | Bassovitch |
| 2006/0201504 A1 | 9/2006 | Singhal et al. |
| 2006/0213518 A1 | 9/2006 | DeVries et al. |
| 2006/0213519 A1 | 9/2006 | Schmidt et al. |
| 2006/0225737 A1 | 10/2006 | Iobbi |
| 2006/0237013 A1 | 10/2006 | Kwok |
| 2006/0243278 A1 | 11/2006 | Hamilton et al. |
| 2006/0249155 A1 | 11/2006 | Gambone |
| 2006/0266361 A1 | 11/2006 | Hernandez |
| 2007/0000490 A1 | 1/2007 | DeVries et al. |
| 2007/0000495 A1 | 1/2007 | Matula et al. |
| 2007/0017515 A1 | 1/2007 | Wallace et al. |
| 2007/0056590 A1 | 3/2007 | Wolfson |
| 2007/0062529 A1 | 3/2007 | Choncholas et al. |
| 2007/0068528 A1 | 3/2007 | Bohm et al. |
| 2007/0074724 A1 | 4/2007 | Duquette et al. |
| 2007/0089743 A1 | 4/2007 | Hoffman |
| 2007/0089745 A1 | 4/2007 | Gabriel et al. |
| 2007/0095347 A1 | 5/2007 | Lampotang et al. |
| 2007/0107728 A1 | 5/2007 | Ricciardelli et al. |
| 2007/0107732 A1 | 5/2007 | Dennis et al. |
| 2007/0107737 A1 | 5/2007 | Landis et al. |
| 2007/0113850 A1 | 5/2007 | Acker et al. |
| 2007/0113856 A1 | 5/2007 | Acker et al. |
| 2007/0125379 A1 | 6/2007 | Pierro et al. |
| 2007/0137653 A1 | 6/2007 | Wood |
| 2007/0163600 A1 | 7/2007 | Hoffman |
| 2007/0173705 A1 | 7/2007 | Teller et al. |
| 2007/0181125 A1 | 8/2007 | Mulier |
| 2007/0193705 A1 | 8/2007 | Hsu |
| 2007/0199568 A1 | 8/2007 | Diekens et al. |
| 2007/0209662 A1 | 9/2007 | Bowen et al. |
| 2007/0215156 A1 | 9/2007 | Kwok |
| 2007/0232950 A1 | 10/2007 | West |
| 2007/0240716 A1 | 10/2007 | Marx |
| 2007/0251528 A1 | 11/2007 | Seitz et al. |
| 2007/0272249 A1 | 11/2007 | Chandran et al. |
| 2008/0000475 A1 | 1/2008 | Hill |
| 2008/0006271 A1 | 1/2008 | Aylsworth et al. |
| 2008/0011298 A1 | 1/2008 | Mazar et al. |
| 2008/0011301 A1 | 1/2008 | Qian |
| 2008/0041371 A1 | 2/2008 | Freitag |
| 2008/0041386 A1 | 2/2008 | Dodier et al. |
| 2008/0045815 A1 | 2/2008 | Derchak et al. |
| 2008/0047559 A1 | 2/2008 | Fiori |
| 2008/0051674 A1 | 2/2008 | Davenport et al. |
| 2008/0053438 A1 | 3/2008 | DeVries et al. |
| 2008/0053447 A1 | 3/2008 | Ratajczak et al. |
| 2008/0060646 A1 | 3/2008 | Isaza |
| 2008/0060657 A1 | 3/2008 | McAuley et al. |
| 2008/0066753 A1 | 3/2008 | Martin et al. |
| 2008/0072902 A1 | 3/2008 | Setzer et al. |
| 2008/0078392 A1 | 4/2008 | Pelletier et al. |
| 2008/0078407 A1 | 4/2008 | Sherman |
| 2008/0092904 A1 | 4/2008 | Gunaratnam et al. |
| 2008/0092905 A1 | 4/2008 | Gunaratnam et al. |
| 2008/0092906 A1 | 4/2008 | Gunaratnam et al. |
| 2008/0099024 A1 | 5/2008 | Gunaratnam et al. |
| 2008/0099027 A1 | 5/2008 | Gunaratnam et al. |
| 2008/0105264 A1 | 5/2008 | Gunaratnam et al. |
| 2008/0110462 A1 | 5/2008 | Chekal et al. |
| 2008/0121230 A1 | 5/2008 | Cortez et al. |
| 2008/0135044 A1 | 6/2008 | Freitag et al. |
| 2008/0142019 A1 | 6/2008 | Lewis et al. |
| 2008/0161653 A1 | 7/2008 | Lin et al. |
| 2008/0173304 A1 | 7/2008 | Zaiser et al. |
| 2008/0178880 A1 | 7/2008 | Christopher et al. |
| 2008/0178881 A1 | 7/2008 | Whitcher et al. |
| 2008/0178882 A1 | 7/2008 | Christopher et al. |
| 2008/0185002 A1 | 8/2008 | Berthon-Jones et al. |
| 2008/0185007 A1 | 8/2008 | Sleeper et al. |
| 2008/0190429 A1 | 8/2008 | Tatarek |
| 2008/0190436 A1 | 8/2008 | Jaffe et al. |
| 2008/0196715 A1 | 8/2008 | Yamamori |
| 2008/0196723 A1 | 8/2008 | Tilley |
| 2008/0196728 A1 | 8/2008 | Ho |
| 2008/0202528 A1 | 8/2008 | Carter et al. |
| 2008/0216834 A1 | 9/2008 | Easley et al. |
| 2008/0216838 A1 | 9/2008 | Wondka |
| 2008/0216841 A1 | 9/2008 | Grimes et al. |
| 2008/0223369 A1 | 9/2008 | Warren |
| 2008/0245369 A1 | 10/2008 | Matula et al. |
| 2008/0251079 A1 | 10/2008 | Richey |
| 2008/0264417 A1 | 10/2008 | Manigel et al. |
| 2008/0283060 A1 | 11/2008 | Bassin |
| 2008/0295846 A1 | 12/2008 | Han et al. |
| 2008/0302364 A1 | 12/2008 | Garde et al. |
| 2008/0308104 A1 | 12/2008 | Blomberg et al. |
| 2009/0007911 A1 | 1/2009 | Cleary et al. |
| 2009/0020121 A1 | 1/2009 | Bassin |
| 2009/0044808 A1 | 2/2009 | Guney et al. |
| 2009/0056708 A1 | 3/2009 | Stenzler et al. |
| 2009/0078255 A1 | 3/2009 | Bowman et al. |
| 2009/0078258 A1 | 3/2009 | Bowman et al. |
| 2009/0095298 A1 | 4/2009 | Gunaratnam et al. |
| 2009/0095300 A1 | 4/2009 | McMorrow |
| 2009/0095303 A1 | 4/2009 | Sher et al. |
| 2009/0099471 A1 | 4/2009 | Broadley et al. |
| 2009/0101147 A1 | 4/2009 | Landis et al. |
| 2009/0101154 A1 | 4/2009 | Mutti et al. |
| 2009/0107502 A1 | 4/2009 | Younes |
| 2009/0118632 A1 | 5/2009 | Goepp |
| 2009/0120437 A1 | 5/2009 | Oates et al. |
| 2009/0126739 A1 | 5/2009 | Ng et al. |
| 2009/0133699 A1 | 5/2009 | Nalagatla et al. |
| 2009/0139527 A1 | 6/2009 | Ng et al. |
| 2009/0145435 A1 | 6/2009 | White et al. |
| 2009/0151719 A1 | 6/2009 | Wondka et al. |
| 2009/0151726 A1 | 6/2009 | Freitag |
| 2009/0151729 A1 | 6/2009 | Judson et al. |
| 2009/0156953 A1 | 6/2009 | Wondka et al. |
| 2009/0165799 A1 | 7/2009 | Duquette et al. |
| 2009/0173347 A1 | 7/2009 | Berthon-Jones |
| 2009/0173349 A1 | 7/2009 | Hernandez et al. |
| 2009/0183739 A1 | 7/2009 | Wondka |
| 2009/0199855 A1 | 8/2009 | Davenport |
| 2009/0205662 A1 | 8/2009 | Kwok et al. |
| 2009/0241947 A1 | 10/2009 | Bedini et al. |
| 2009/0241951 A1 | 10/2009 | Jafari et al. |
| 2009/0250066 A1 | 10/2009 | Daly |
| 2009/0255533 A1 | 10/2009 | Freitag et al. |
| 2009/0260625 A1 | 10/2009 | Wondka |
| 2009/0277452 A1 | 11/2009 | Lubke et al. |
| 2009/0293877 A1 | 12/2009 | Blanch et al. |
| 2009/0301495 A1 | 12/2009 | Pierro et al. |
| 2009/0308395 A1 | 12/2009 | Lee et al. |
| 2009/0320851 A1 | 12/2009 | Selvarajan et al. |
| 2010/0043786 A1 | 2/2010 | Freitag et al. |
| 2010/0071693 A1 | 3/2010 | Allum et al. |
| 2010/0071697 A1 | 3/2010 | Jafari et al. |
| 2010/0083968 A1 | 4/2010 | Wondka et al. |
| 2010/0108073 A1 | 5/2010 | Zollinger et al. |
| 2010/0132716 A1 | 6/2010 | Selvarajan et al. |
| 2010/0132717 A1 | 6/2010 | Davidson et al. |
| 2010/0163043 A1 | 7/2010 | Hart et al. |
| 2010/0170512 A1 | 7/2010 | Kuypers et al. |
| 2010/0170513 A1 | 7/2010 | Bowditch et al. |
| 2010/0192957 A1 | 8/2010 | Hobson et al. |
| 2010/0218766 A1 | 9/2010 | Milne |

(56) References Cited

U.S. PATENT DOCUMENTS

| | | |
|---|---|---|
| 2010/0224196 A1 | 9/2010 | Jablons |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0252044 A1 | 10/2010 | Duquette et al. |
| 2010/0269834 A1 | 10/2010 | Freitag et al. |
| 2010/0275920 A1 | 11/2010 | Tham et al. |
| 2010/0275921 A1 | 11/2010 | Schindhelm et al. |
| 2010/0282251 A1 | 11/2010 | Calluaud et al. |
| 2010/0282810 A1 | 11/2010 | Hawes |
| 2010/0288279 A1 | 11/2010 | Seiver et al. |
| 2010/0288289 A1 | 11/2010 | Nasir |
| 2010/0300445 A1 | 12/2010 | Chatburn et al. |
| 2010/0300446 A1 | 12/2010 | Nicolazzi et al. |
| 2010/0307487 A1 | 12/2010 | Dunsmore et al. |
| 2010/0307495 A1 | 12/2010 | Kepler et al. |
| 2010/0307499 A1 | 12/2010 | Eger et al. |
| 2010/0307500 A1 | 12/2010 | Armitstead |
| 2010/0307502 A1 | 12/2010 | Rummery et al. |
| 2010/0313891 A1 | 12/2010 | Veliss et al. |
| 2010/0313898 A1 | 12/2010 | Richard et al. |
| 2010/0319703 A1 | 12/2010 | Hayman et al. |
| 2010/0326441 A1 | 12/2010 | Zucker et al. |
| 2010/0326446 A1 | 12/2010 | Behlmaier |
| 2011/0000489 A1 | 1/2011 | Laksov et al. |
| 2011/0009763 A1 | 1/2011 | Levitsky et al. |
| 2011/0011402 A1 | 1/2011 | Berthon-Jones |
| 2011/0023878 A1 | 2/2011 | Thiessen |
| 2011/0023881 A1 | 2/2011 | Thiessen |
| 2011/0034819 A1 | 2/2011 | Desforges et al. |
| 2011/0036352 A1 | 2/2011 | Estes et al. |
| 2011/0041850 A1 | 2/2011 | Vandine et al. |
| 2011/0041855 A1 | 2/2011 | Gunaratnam et al. |
| 2011/0061647 A1 | 3/2011 | Stahmann et al. |
| 2011/0067704 A1 | 3/2011 | Kooij et al. |
| 2011/0067709 A1 | 3/2011 | Doshi et al. |
| 2011/0071444 A1 | 3/2011 | Kassatly et al. |
| 2011/0073107 A1 | 3/2011 | Rodman et al. |
| 2011/0073116 A1 | 3/2011 | Genger et al. |
| 2011/0087123 A9 | 4/2011 | Choncholas et al. |
| 2011/0088690 A1 | 4/2011 | Djupesland et al. |
| 2011/0094518 A1 | 4/2011 | Cipollone et al. |
| 2011/0100365 A1 | 5/2011 | Wedler et al. |
| 2011/0114098 A1 | 5/2011 | Mcauley et al. |
| 2011/0125052 A1 | 5/2011 | Davenport et al. |
| 2011/0126841 A1 | 6/2011 | Matula, Jr. et al. |
| 2011/0132363 A1 | 6/2011 | Chalvignac |
| 2011/0139153 A1 | 6/2011 | Chalvignac |
| 2011/0146687 A1 | 6/2011 | Fukushima |
| 2011/0155140 A1 | 6/2011 | Ho et al. |
| 2011/0162650 A1 | 7/2011 | Miller et al. |
| 2011/0162655 A1 | 7/2011 | Gunaratnam et al. |
| 2011/0178419 A1 | 7/2011 | Wood et al. |
| 2011/0180068 A1 | 7/2011 | Kenyon et al. |
| 2011/0197885 A1 | 8/2011 | Wondka et al. |
| 2011/0209705 A1 | 9/2011 | Freitag |
| 2011/0214676 A1 | 9/2011 | Allum et al. |
| 2011/0220105 A1 | 9/2011 | Meier |
| 2011/0232642 A1 | 9/2011 | Bliss et al. |
| 2011/0247625 A1 | 10/2011 | Boussignac |
| 2011/0253147 A1 | 10/2011 | Gusky et al. |
| 2011/0259327 A1 | 10/2011 | Wondka et al. |
| 2011/0265796 A1 | 11/2011 | Amarasinghe et al. |
| 2011/0277765 A1 | 11/2011 | Christopher et al. |
| 2011/0284003 A1 | 11/2011 | Douglas et al. |

FOREIGN PATENT DOCUMENTS

| | | |
|---|---|---|
| DE | 19841070 | 5/2000 |
| DE | 19849571 | 5/2000 |
| DE | 10337138.9 | 3/2005 |
| DE | 10 2006 023 637.8 | 11/2007 |
| EP | 0125424 | 11/1984 |
| EP | 0692273 | 1/1996 |
| EP | 0778035 | 6/1997 |
| EP | 1359961 | 11/2003 |
| EP | 2377462 | 11/2010 |
| GB | 2174609 | 11/1986 |
| GB | 2201098 | 8/1988 |
| GB | 1055148 | 6/1989 |
| GB | 2338420 | 12/1999 |
| JP | S63-57060 | 3/1998 |
| JP | 2002-204830 | 7/2002 |
| WO | WO-92/11054 | 7/1992 |
| WO | WO-98/01176 | 1/1998 |
| WO | WO-99/04841 | 2/1999 |
| WO | WO-00/64521 | 11/2000 |
| WO | WO-01/76655 | 10/2001 |
| WO | WO-02/062413 | 8/2002 |
| WO | WO-2004/009169 | 1/2004 |
| WO | WO-2005/014091 | 2/2005 |
| WO | WO-2005/018524 | 3/2005 |
| WO | WO-2006/138580 | 12/2006 |
| WO | WO-2007/035804 | 3/2007 |
| WO | WO-2007/139531 | 12/2007 |
| WO | WO-2007142812 | 12/2007 |
| WO | WO-2008/014543 | 2/2008 |
| WO | WO-2008/019102 | 2/2008 |
| WO | WO-2008/052534 | 5/2008 |
| WO | WO-2008/112474 | 9/2008 |
| WO | WO-2008/138040 | 11/2008 |
| WO | WO-2008/144589 | 11/2008 |
| WO | WO-2008/144669 | 11/2008 |
| WO | WO-2009/042973 | 4/2009 |
| WO | WO-2009/042974 | 4/2009 |
| WO | WO-2009/059353 | 5/2009 |
| WO | WO-2009/064202 | 5/2009 |
| WO | WO-2009/074160 | 6/2009 |
| WO | WO-2009/082295 | 7/2009 |
| WO | WO-2009/087607 | 7/2009 |
| WO | WO-2009/092057 | 7/2009 |
| WO | WO-2009/103288 | 8/2009 |
| WO | WO-2009/109005 | 9/2009 |
| WO | WO-2009/115944 | 9/2009 |
| WO | WO-2009/115948 | 9/2009 |
| WO | WO-2009/115949 | 9/2009 |
| WO | WO-2009/129506 | 10/2009 |
| WO | WO-2009/136101 | 11/2009 |
| WO | WO-2009/139647 | 11/2009 |
| WO | WO-2009/149351 | 12/2009 |
| WO | WO-2009/149353 | 12/2009 |
| WO | WO-2009/149355 | 12/2009 |
| WO | WO-2009/149357 | 12/2009 |
| WO | WO-2009/151344 | 12/2009 |
| WO | WO-2009/151791 | 12/2009 |
| WO | WO-2010/000135 | 1/2010 |
| WO | WO-2010/021556 | 2/2010 |
| WO | WO-2010/022363 | 2/2010 |
| WO | WO-2010/039989 | 4/2010 |
| WO | WO-2010/041966 | 4/2010 |
| WO | WO-2010/044034 | 4/2010 |
| WO | WO-2010/057268 | 5/2010 |
| WO | WO-2010/059049 | 5/2010 |
| WO | WO-2010/060422 | 6/2010 |
| WO | WO-2010/068356 | 6/2010 |
| WO | WO-2010/070493 | 6/2010 |
| WO | WO-2010/070497 | 6/2010 |
| WO | WO-2010/070498 | 6/2010 |
| WO | WO-2010/076711 | 7/2010 |
| WO | WO-2010/081223 | 7/2010 |
| WO | WO-2010/091157 | 8/2010 |
| WO | WO-2010/099375 | 9/2010 |
| WO | WO-2010/102094 | 9/2010 |
| WO | WO-2010/115166 | 10/2010 |
| WO | WO-2010/115168 | 10/2010 |
| WO | WO-2010/115169 | 10/2010 |
| WO | WO-2010/115170 | 10/2010 |
| WO | WO-2010/116275 | 10/2010 |
| WO | WO-2010/132853 | 11/2010 |
| WO | WO-2010/136923 | 12/2010 |

(56) References Cited

FOREIGN PATENT DOCUMENTS

| WO | WO-2010/139014 | 12/2010 |
|---|---|---|
| WO | WO-2010/150187 | 12/2010 |
| WO | WO-2011/002608 | 1/2011 |
| WO | WO-2011/004274 | 1/2011 |
| WO | WO-2011/006184 | 1/2011 |
| WO | WO-2011/006199 | 1/2011 |
| WO | WO-2011/014931 | 2/2011 |
| WO | WO-2011/017033 | 2/2011 |
| WO | WO-2011/017738 | 2/2011 |
| WO | WO-2011/021978 | 2/2011 |
| WO | WO-2011/022779 | 3/2011 |
| WO | WO-2011/024383 | 3/2011 |
| WO | WO-2011/029073 | 3/2011 |
| WO | WO-2011/029074 | 3/2011 |
| WO | WO-2011/035373 | 3/2011 |
| WO | WO-2011/038950 | 4/2011 |
| WO | WO-2011/038951 | 4/2011 |
| WO | WO-2011/044627 | 4/2011 |
| WO | WO-2011/057362 | 5/2011 |
| WO | WO 2011/059346 | 5/2011 |
| WO | WO-2011/061648 | 5/2011 |
| WO | WO-2011/062510 | 5/2011 |
| WO | WO-2011/086437 | 7/2011 |
| WO | WO-2011/086438 | 7/2011 |
| WO | WO-2011/112807 | 9/2011 |

OTHER PUBLICATIONS

In the U.S. Patent and Trademark Office, Supplemental Notice of Allowance dated in re: U.S. Appl. No. 10/771,803, dated Nov. 7, 2008, 2 pages.
In the U.S. Patent and Trademark Office, Examiner's Interview Summary in re: U.S. Appl. No. 10/771,803, dated Oct. 31, 2008, 4 pages.
In the U.S. Patent and Trademark Office, Notice of Allowance dated in re: U.S. Appl. No. 10/771,803, dated Oct. 20, 2008, 8 pages.
In the U.S. Patent and Trademark Office, Examiner's Interview Summary in re: U.S. Appl. No. 10/771,803, dated Nov. 2, 2007, 2 pages.
In the U.S. Patent and Trademark Office, Office Action in re: U.S. Appl. No. 10/771,803, dated Jun. 14, 2007, 12 pages.
In the U.S. Patent and Trademark Office, Restriction Requirement in re: U.S. Appl. No. 12/271,484, dated Feb. 9, 2011, 5 pages.
In the U.S. Patent and Trademark Office, Restriction Requirement in re: U.S. Appl. No. 12/754,437, dated Aug. 16, 2011, 5 pages.
In the U.S. Patent and Trademark Office, Non-Final Office Action dated in re: U.S. Appl. No. 10/567,746, dated Oct. 5, 2009, 9 pages.
In the U.S. Patent and Trademark Office, Notice of Allowance and Examiner's Interview Summary in re: U.S. Appl. No. 11/523,519, dated Jan. 16, 2009, 10 pages.
In the U.S. Patent and Trademark Office, Examiner's Interview Summary in re: U.S. Appl. No. 11/523,519, dated Jan. 13, 2009, 4 pages.
In the U.S. Patent and Trademark Office, Final Office Action in re: U.S. Appl. No. 11/523,519, dated Jul. 11, 2008, 13 pages.
In the U.S. Patent and Trademark Office, Examiner's Interview Summary in re: U.S. Appl. No. 11/523,519, dated Apr. 10, 2008, 3 pages.
In the U.S. Patent and Trademark Office, Final Office Action in re: U.S. Appl. No. 11/523,519, dated Nov. 26, 2007, 14 pages.
In the U.S. Patent and Trademark Office, Office Action in re: U.S. Appl. No. 11/523,519, dated Mar. 7, 2007, 11 pages.
In the U.S. Patent and Trademark Office, Restriction Requirement in re: U.S. Appl. No. 11/523,518, dated Dec. 30, 2009, 4 pages.
In the U.S. Patent and Trademark Office, Supplemental Notice of Allowance in re: U.S. Appl. No. 11/798,965, dated Aug. 21, 2009, 4 pages.
In the U.S. Patent and Trademark Office, Notice of Allowance in re: U.S. Appl. No. 11/798,965, dated Jul. 17, 2009, 5 pages.
In the U.S. Patent and Trademark Office, Final Office Action in re: U.S. Appl. No. 11/798,965, dated Apr. 9, 2009, 6 pages.
In the U.S. Patent and Trademark Office, Office Action in re: U.S. Appl. No. 11/798,965, dated Jul. 29, 2008, 12 pages.
In the U.S. Patent and Trademark Office, Office Action in re: U.S. Appl. No. 12/578,283, dated Oct. 19, 2011, 5 pages.
In the U.S. Patent and Trademark Office, Restriction/Election Requirement in re: U.S. Appl. No. 11/882,530, dated Apr. 27, 2011, 5 pages.
In the U.S. Patent and Trademark Office, Supplemental Notice of Allowance in re: U.S. Appl. No. 10/870,849, dated Jun. 16, 2009, 2 pages.
In the U.S. Patent and Trademark Office, Notice of Allowance in re: U.S. Appl. No. 10/870,849, dated Jun. 3, 2009, 4 pages.
In the U.S. Patent and Trademark Office, Notice of Allowance in re: U.S. Appl. No. 10/870,849, dated May 14, 2009, 8 pages.
In the U.S. Patent and Trademark Office, Restriction in re: U.S. Appl. No. 10/870,849, dated Nov. 16, 2007, 5 pages.
In the U.S. Patent and Trademark Office, Examiner's Interview Summary in re: U.S. Appl. No. 10/870,849, dated Jul. 27, 2007, 2 pages.
In the U.S. Patent and Trademark Office, Office Action in re: U.S. Appl. No. 10/870,849, dated Feb. 22, 2007, 13 pages.
In the U.S. Patent and Trademark Office, Restriction/Election Requirement in re: U.S. Appl. No. 12/493,677, dated Aug. 5, 2011, 5 pages.
In the U.S. Patent and Trademark Office, Restriction/Election Requirement in re: U.S. Appl. No. 12/153,423, dated Oct. 6, 2011, 8 pages.
In the U.S. Patent and Trademark Office, Notice of Allowance in re: U.S. Appl. No. 10/922,054, dated Feb. 12, 2008, 6 pages.
In the U.S. Patent and Trademark Office, Final Office Action in re: U.S. Appl. No. 10/922,054, dated Nov. 27, 2007, 9 pages.
In the U.S. Patent and Trademark Office, Office Action in re: U.S. Appl. No. 10/922,054, dated Mar. 14, 2007, 14 pages.
In the U.S. Patent and Trademark Office, Office Action in re: U.S. Appl. No. 10/922,054, dated Sep. 7, 2006, 21 pages.
In the U.S. Patent and Trademark Office, Restriction Requirement in re: U.S. Appl. No. 10/922,054, dated May 17, 2006, 5 pages.
In the U.S. Patent and Trademark Office, Notice of Allowance and Examiner's Interview Summary in re: U.S. Appl. No. 12/076,062, dated Nov. 2, 2011, 8 pages.
In the U.S. Patent and Trademark Office, Office Action in re: U.S. Appl. No. 12/076,062, dated Jan. 13, 2011, 14 pages.
In the U.S. Patent and Trademark Office, Office Action in re: U.S. Appl. No. 12/355,753, dated Sep. 28, 2011, 32 pages.
In the U.S. Patent and Trademark Office, *Ex Parte Quayle* Office Action in re: U.S. Appl. No. 29/388,700, dated Oct. 7, 2011, 5 pages.
"AARC Clinical Practice Guideline: Oxygen Therapy in the Home or Extended Care Facility," *Resp. Care*, 1992: 37(8), pp. 918-922.
"ATS Statement: Guidelines for the Six-Minute Walk Test," *Am. J. Respir. Crit. Care Med.*, 2002: 166, pp. 111-117.
"Passy-Muir Speaking Valves," *Respiratory*, Nov. 13, 1998, 7 pages.
Ambrosino, "Exercise and noninvasive ventilatory support," *Monaldi Arch Chest Dis.*, 2000: 55(3): 242-246.
Ambrosino, "Weaning and Respiratory Muscle Dysfunction: The Egg Chicken Dilemma," *Chest*, 2005: 128(2), pp. 481-483.
Bach et al., "Intermittent Positive Pressure Ventilation via Nasal Access in the Management of Respiratory Insufficiency," *Chest*, 1987: 92(1), pp. 168-170.
Banner et al., "Extubating at a Pressure Support Ventilation Level Corresponding to Zero Imposed Work of Breathing," *Anesthesiology*, Sep. 1994: 81(3A), p. A271.
Banner et al., "Imposed Work of Breathing and Methods of Triggering a Demand-Flow, Continuous Positive Airway Pressure System," *Critical Care Medicine*, 1993: 21(2), pp. 183-190.
Banner et al., "Site of Pressure Measurement During Spontaneous Breathing with Continuous Positive Airway Pressure: Effect on Calculating Imposed Work of Breathing," *Critical Care Medicine*, 1992: 20(4), pp. 528-533.
Barakat et al., "Effect of noninvasive ventilatory support during exercise of a program in pulmonary rehabilitation in patients with COPD," *Int. J. Chron. Obstruct. Pulmon. Dis.*, 2007: 2(4), pp. 585-591.
Barreiro et al., "Noninvasive ventilation," *Crit Care Clin.*, 2007; 23(2): 201-22.
Bauer et al., "ADAM Nasal CPAP Circuit Adaptation: A Case Report," *Sleep*, 1991: 14(3), pp. 272-273.
Blanch, "Clinical Studies of Tracheal Gas Insufflation," *Resp. Care*, 2001: 45(2), pp. 158-166.

(56) References Cited

OTHER PUBLICATIONS

Borghi-Silva et al., "Non-invasive ventilation improves peripheral oxygen saturation and reduces fatigability of quadriceps in patients with COPD," Respirology, 2009, 14:537-546.
Bossi et al., "Continuous Positive Airway Pressure in the Spontaneously Breathing Newborn by Means of Bilateral Nasal Cannulation," *Monatsschr Kinderheilkd*, 1975: 123(4), pp. 141-146.
Boussarsar et al., "Relationship between ventilatory settings and barotrauma in the acute respiratory distress syndrome," Intensive Care Med., 2002: 28(4): 406-13.
Chang et al., "Reduced Inspiratory Muscle Endurance Following Successful Weaning From Prolonged Mechanical Ventilation," *Chest*, 2005: 128(2), pp. 553-559.
Charlotte Regional Medical Center, "Application of the Passy-Muir Tracheostomy and Ventilator," *Speech-Language Pathology Department*, Jan. 1995, 8 pages.
Christopher et al., "Preliminary Observations of Transtracheal Augmented Ventilation for Chronic Severe Respiratory Disease," *Resp. Care*, 2001: 46(1), pp. 15-25.
Christopher, et al., "Transtracheal Oxygen Therapy for Refractory Hypoxemia," *JAMA*, 1986: 256(4), pp. 494-497.
Ciccolella et al.; "Administration of High-Flow, Vapor-phased, Humidified Nasal Cannula Air (HF-HNC) Decreases Work of Breathing (WOB) in Healthy Subjects During Exercise," *AmJRCCM*, Apr. 2001: 163(5), Part 2, pp. A622. (Abstract Only).
Clini et al., "The Italian multicentre study on noninvasive ventilation in chronic obstructive pulmonary disease patients," *Eur. Respir. J.*, 2002, 20(3): 529-538.
Costa et al., "Influence of noninvasive ventilation by BiPAP® on exercise tolerance and respiratory muscle strength in chronic obstructive pulmonary disease patients (COPD)," *Rev. Lat. Am. Enfermagem.*, 2006: 14(3), pp. 378-382.
Díaz et al., "Breathing Pattern and Gas Exchange at Peak Exercise in COPD Patients With and Without Tidal Flow Limitation at Rest," *European Respiratory Journal*, 2001: 17, pp. 1120-1127.
Enright, "The six-minute walk test," *Resp. Care*, 2003: 8, pp. 783-785.
Ferreira et al., "Trigger Performance of Mid-level ICU Mechanical Ventilators During Assisted Ventilation: A Bench Study," *Intensive Care Medicine*, 2008,34:1669-1675.
Fink, "Helium-Oxygen: An Old Therapy Creates New Interest," *J. Resp. Care. Pract. now RT for Decision Makers in Respiratory Care*, 1999, pp. 71-76.
Gaughan et al., "A Comparison in a Lung Model of Low- and High-Flow Regulators for Transtracheal Jet Ventilation," *Anesthesiology*, 1992: 77(1), pp. 189-199.
Gregoretti, et al., "Transtracheal Open Ventilation in Acute Respiratory Failure Secondary to Severe Chronic Obstructive Pulmonary Disease Exacerbation," *Am. J. Resp. Crit. Care. Med.*, 2006: 173(8), pp. 877-881.
Haenel et al., "Efficacy of Selective Intrabronchial Air Insufflation in Acute Lobar Colapse," *Am. J. Surg.*, 1992: 164(5), pp. 501-505.
Keilty et al., "Effect of inspiratory pressure support on exercise tolerance and breathlessness in patients with severe stable chronic obstructive pulmonary disease," *Thorax*, 1994, 49(10): 990-994.
Köhnlein et al., "Noninvasive ventilation in pulmonary rehabilitation of COPD patients," *Respir. Med.*, 2009: 103: 1329-1336.
Koska et al., "Evaluation of a Fiberoptic System for Airway Pressure Monitoring," *J. Clin. Monit.*, 1993: 10(4), pp. 247-250.
Lewis, "Breathless No More, Defeating Adult Sleep Apnea," *FDA Consumer Magazine*, Jun. 1992, pp. 33-37.
Limberg et al., "Changes in Supplemental Oxygen Prescription in Pulmonary Rehabilitation," *Resp. Care*, 2006:51(11), p. 1302.
MacInryre, "Long-Term Oxygen Therapy: Conference Summary," *Resp. Care*, 2000: 45(2), pp. 237-245.
MacIntyre et al., "Acute exacerbations and repiratory failure in chronic obstructive pulmonary disease," *Proc. Am. Thorac. Soc.*, 2008: 5(4), pp. 530-535.

Massie et al., "Clinical Outcomes Related to Interface Type in Patients With Obstructive Sleep Apnea/Hypopnea Syndrome Who Are Using Continuous Positive Airway Pressure," *Chest*, 2003: 123(4), pp. 1112-1118.
McCoy, "Oxygen Conservation Techniques and Devices," *Resp. Care*, 2000: 45(1), pp. 95-104.
McGinley, "A nasal cannula can be used to treat obstructive sleep apnea"; *Am. J. Resp. Crit. Care Med.*, 2007: 176(2), pp. 194-200.
Menadue et al., "Non-invasive ventilation during arm exercise and ground walking in patients with chronic hypercapnic respiratory failure," *Respirology*, 2009, 14(2): 251-259.
Menon et al., "Tracheal Perforation. A Complication Associated with Transtracheal Oxygen Therapy," *Chest*, 1993: 104(2), pp. 636-637.
Messinger et al., "Tracheal Pressure Triggering a Demand-Flow CPAP System Decreases Work of Breathing," Anesthesiology, 1994: 81(3A), p. A272.
Messinger et al., "Using Tracheal Pressure to Trigger the Ventilator and Control Airway Pressure During Continuous Positive Airway Pressure Decreases Work of Breathing," *Chest*, 1995: vol. 108(2), pp. 509-514.
Mettey, "Use of CPAP Nasal Cannula for Aids of the Newborns in Tropical Countries," *Medecine Tropicale*, 1985: 45(1), pp. 87-90.
Nahmias et al., "Treatment of the Obstructive Sleep Apnea Syndrome Using a Nasopharyngeal Tube", *Chest*, 1988:94(6), pp. 1142-1147.
Nava et al., "Non-invasive ventilation," *Minerva Anestesiol.*, 2009: 75(1-2), pp. 31-36.
Passy-Muir Inc., "Clinical Inservice Outline", Apr. 2004, 19 pages.
Peters et al., "Combined Physiological Effects of Bronchodilators and Hyperoxia on Exertional Dyspnea in Normoxic COPD," *Thorax*, 2006: 61, pp. 559-567.
Polkey et al., "Inspiratory pressure support reduces slowing of inspiratory muscle relations rate during exhaustive treadmill walking in sever COPD," *Am. J. Resp. Crit. Care Med.*, 1996: 154(4, 10), pp. 1146-1150.
Porta et al., "Mask proportional assist vs pressure support ventilation in patients in clinically stable condition with chronic venilatory failure," *Chest*, 2002: 122(2), pp. 479-488.
Prigent et al., "Comparative Effects of Two Ventilatory Modes on Speech in Tracheostomized Patients with Neuromuscular Disease," *Am. J. Resp. Crit. Care Med.*, 2003: 167(8), pp. 114-119.
Puente-Maestu et al., "Dyspnea, Ventilatory Pattern, and Changes in Dynamic Hyperinflation Related to the Intensity of Constant Work Rate Exercise in COPD," *Chest*, 2005: 128(2), pp. 651-656.
Ram et al., "Non-invasive positive pressure ventilation for treatment of respiratory failure due to exacerbations of chroic obstructive pulmonary disease," *Cochrane Database Syst Rev.*, 2004(3):1-72.
Rothe et al., "Near Fatal Complication of Transtracheal Oxygen Therapy with the SCOOP(R) System," *Pneumologie*, 1996: 50(10), pp. 700-702. (English Abstract provided.).
Rothfleisch et al., "Facilitation of fiberoptic nasotracheal intubation in a morbidly obese patient by simultaneous use of nasal CPAP," Chest, 1994, 106(1): 287-288.
Sanders et al., "CPAP Via Nasal Mask: A Treatment for Occlusive Sleep Apnea," *Chest*, 1983: 83(1), pp. 144-145.
Sinderby et al., "Neural control of mechanical ventilation in respiratory failure," *Nat. Med.*, 1999: 5(12), pp. 1433-1436.
Somfay et al., "Dose-Response Effect of Oxygen on Hyperinflation and Exercise Endurance in Nonhypoxaemic COPD Patients," *Eur. Resp. J.*, 2001: 18, pp. 77-84.
Sullivan et al., "Reversal of Obstructive Sleep Apnoea by Continuous Positive Airway Pressure Applied Through the Nares," *The Lancet*, 1981: 1(8225), pp. 862-865.
Sullivan, "Home treatment of obstructive sleep apnoea with continuous positive airway pressure applied through a nose-mask," *Bull Eur Physiopathol Respir.*, 1984: 20(1), pp. 49-54.
Tiep et al., "Pulsed nasal and transtracheal oxygen delivery," *Chest*, 1990: 97, pp. 364-368.
Tsuboi et al., "Ventilatory Support During Exercise in Patients With Pulmonary Tuberculosis Sequelae," *Chest*, 1997: 112(4), pp. 1000-1007.
*VHA/DOD Clinical Practice Guideline*, "Management of Chronic Obstructive Pulmonary Disease," Aug. 1999, Ver. 1.1a, Updated Nov. 1999.

(56) References Cited

OTHER PUBLICATIONS

Wijkstra et al., "Nocturnal non-invasive positive pressure ventilation for stable chronic obstructive pulmonary disease," *Cochrane Database Syst. Rev.*, 2002, 3: 1-22.
Yaeger et al., "Oxygen Therapy Using Pulse and Continuous Flow With a Transtracheal Catheter and a Nasal Cannula," *Chest*, 1994: 106, pp. 854-860.
Walsh, "McGraw Hill Pocket reference Machinists' and Metalworker' Pocket Reference," *New York McGraw-Hill*, 2000, pp. 3-67, submitting 3 pages.
International Preliminary Report and Written Opinion on Patentability for PCT/DE2004/001646, dated Jul. 3, 2006.
European patent Office Search Report issued Oct. 19, 2007 in copending EP 04762494.
International Search Report and Written Opinion for PCT/US04/26800 issued Jun. 22, 2006.
International Search Report and Written Opinion for PCT/US07/12108, dated Aug. 8, 2008.
International Search Report and Written Opinion for PCT/US07/17400, dated Apr. 28, 2008.
International Search Report and Written Opinion for PCT/US08/64015, dated Sep. 26, 2008.
International Search Report and Written Opinion for PCT/US08/64164, dated Sep. 29, 2008.
International Search Report and Written Opinion for PCT/US08/78031, dated Nov. 24, 2008.
International Search Report and Written Opinion for PCT/US08/78033, dated Dec. 3, 2008.
International Search Report and Written Opinion for PCT/US09/054673, dated Oct. 8, 2009.
International Search Report and Written Opinion for PCT/US09/41027, dated Dec. 14, 2009.
International Search Report and Written Opinion for PCT/US09/59272, dated Dec. 2, 2009.
International Search Report and Written Opinion for PCT/US2006/036600, dated Apr. 3, 2007.
International Search Report and Written Opinion for PCT/US2009/031355 issued Mar. 11, 2009.
International Search Report and Written Opinion for PCT/US2009/041034, dated Jun. 10, 2009.
International Search Report and Written Opinion for PCT/US2010/029871, dated Jul. 12, 2010.
International Search Report and Written Opinion for PCT/US2010/029873, dated Jun. 28, 2010.
International Search Report and Written Opinion for PCT/US2010/029874, dated Jul. 12, 2010.
International Search Report and Written Opinion for PCT/US2010/029875, dated Jul. 12, 2010.
International Search Report and Written Opinion for PCT/US2010/047920, dated Nov. 1, 2010.
International Search Report and Written Opinion for PCT/US2010/047921, dated Jan. 27, 2011.
International Search Report for PCT/DE2004/001646, dated Jan. 17, 2005.

\* cited by examiner

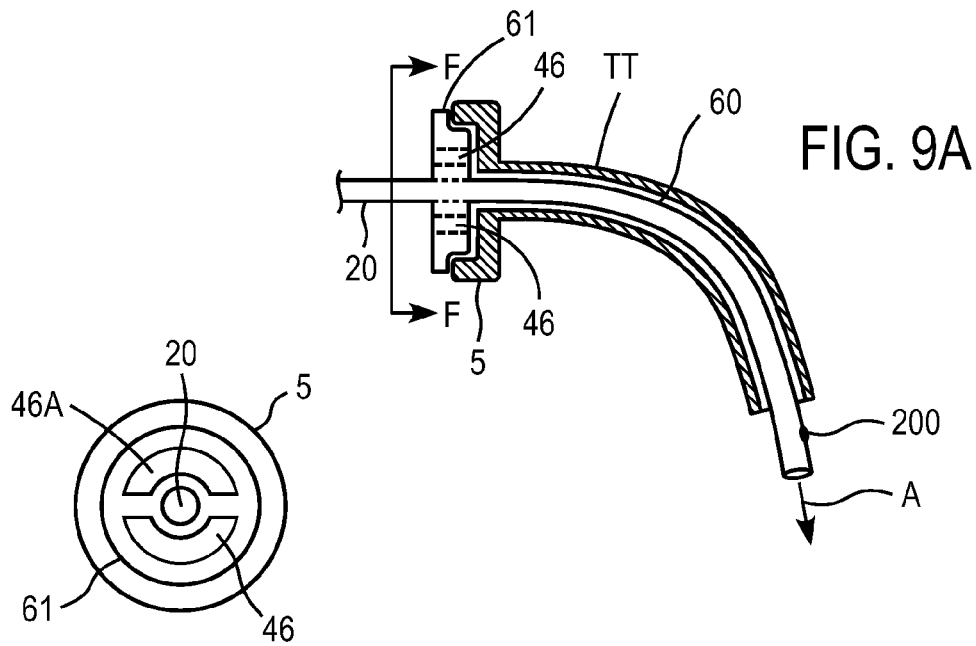
FIG. 9A
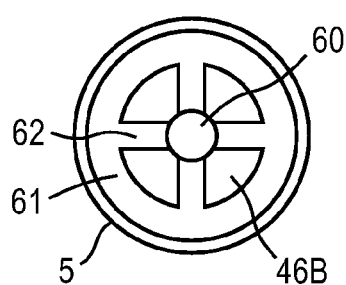
SECTION F-F
FIG. 9B
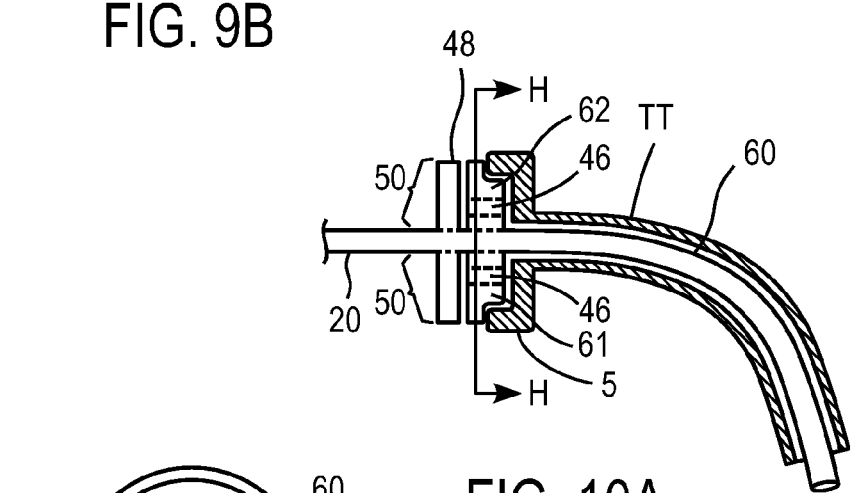
FIG. 10A
SECTION H-H
FIG. 10B

SECTION P-P

SECTION N-N

SECTION N-N

SECTION N-N

Section R-R

METHODS AND DEVICES FOR PROVIDING INSPIRATORY AND EXPIRATORY FLOW RELIEF DURING VENTILATION THERAPY

This application claims the benefit of U.S. Provisional Application No. 60/960,370 filed Sep. 26, 2007, which is incorporated by reference herein in its entirety.

FIELD OF THE INVENTION

This invention relates to ventilation therapy for persons suffering from respiratory impairment and breathing disorders, such as chronic obstructive pulmonary disease (COPD), pulmonary fibrosis, acute respiratory distress syndrome (ARDS), neuromuscular impairment, and sleep apnea.

The present invention relates specifically to providing a means for exhalation and inspiration through a ventilation tube in the event that an obstruction occurs which would otherwise prevent the patient from adequately inhaling or exhaling through their normal upper airway ventilation route.

BACKGROUND OF THE INVENTION

There are two general types of control systems for ventilators, or ventilation, known in the art. A first type of ventilation control system delivers gas to a patient based on a frequency that is selected by the clinician and is independent of patient activity. This type of ventilation, known as "controlled mechanical ventilation," (CMV) is used when a patient needs a ventilator to breathe for him or her. Non-limiting examples of when a patient needs CMV include when the patient is non-alert, sedated, unresponsive, or paralyzed. A second type of ventilation control system, delivers gas to a patient in response to an inspiratory effort generated by the patient. This type of ventilation, which includes "assisted ventilation" or "augmented ventilation" and may be referred to as "respiratory support", assists the patient to breathe. Non-limiting examples of patients who need or can benefit from this type of ventilation include patients suffering from respiratory insufficiency, respiratory impairment, or breathing disorders, such as patients suffering from COPD, pulmonary fibrosis, acute respiratory distress syndrome (ARDS), neuromuscular impairment, or sleep apnea. There are also ventilators and modes of ventilation that combine the two types of ventilators described above.

All ventilators comprise a ventilation interface connecting the ventilator to the patient. These interfaces can be non-invasive or invasive. A non-limiting example of non-invasive interfaces includes a mask over the nose and/or mouth. Non-limiting examples of invasive interfaces include an endotracheal tube, a tracheostomy tube, and a transtracheal catheter, which is placed into the airway of the patient.

A number of problems can arise during ventilation. The present invention addresses the problem of physical obstruction of inspiratory or expiratory airflow, which is one problem that can arise during ventilation. In the case of mechanical ventilation, an obstruction can occur anywhere in the gas delivery circuit or breathing circuit. Typically, such an obstruction in a mechanical ventilation system is annunciated by alarms, and an attending clinician is required to correct the problem, since the patient may not be capable of doing so. In the case of respiratory support ventilation, the obstruction can occur anywhere in the gas delivery circuit or breathing circuit, as well. In the case of respiratory support ventilation, there needs to be a valve somewhere in the gas delivery circuit or breathing circuit that can open or be opened to atmosphere so that the patient can breathe ambient air through that valve to prevent suffocation. Further, if the obstruction creates an overpressure condition, the same valve or a different valve must activate or be activated to open the gas delivery circuit to atmosphere to allow the lung pressure to decrease to prevent lung barotrauma.

In a more specific type of respiratory support ventilation, the patient receives gas from the ventilator in a gas delivery circuit known as an "open" system, meaning that the patient's lungs are open to atmosphere through their normal upper airway breathing routes (trachea, mouth, and nose). In this case, referred to throughout this specification as "open ventilation," the patient is breathing "spontaneously," or naturally, through their upper airway, but their breathing is augmented by receiving additional gas from the ventilator through the "open" gas delivery circuit. Typically the patient exhales directly to ambient through their airway and not through the gas delivery circuit. However, in some systems or some situations, that the patient may exhale through the gas delivery circuit. An open ventilation system is described in detail in US Patent Application No. 2005/003472 (Freitag) and in US Patent Application No. 2005/0005936 (Wondka), each of which is hereby incorporated by reference herein in its entirety. The ventilation interface in an open system is typically a transtracheal catheter that is placed percutaneously through the patient's neck into the tracheal lumen. Alternatively, the ventilation catheter is placed into an un-cuffed tracheostomy tube, a tracheostomy tube with a deflated cuff, a stent or stoma guide, such as a Montgomery T-Tube, or an airway prosthesis such as that shown in US Patent Application No. 2005/003472 (Freitag).

In "open" system ventilation, one concern about obstruction is an obstruction of the upper airway. Non-limiting examples of obstruction of the upper airway that may occur include swelling of the oro-pharyngeal structures; closure of the oro-pharyngeal structures, such as that which could occur in obstructive sleep apnea syndrome; stenosis of the airway caused, for example, by tracheal malacia; rapid swelling of the airway tissues; or inadvertent inflation of a cuff on a tracheostomy tube. If any event such these, or other airway-obstructing event, occurs, the patient is obstructed or restricted from being able to spontaneously breathe, and the amount of gas received from the ventilator through the open gas delivery circuit may not be enough to sustain respiration. Hence, an inspiratory and expiratory pressure or airflow relief mechanism is warranted in these circumstances to provide an additional spontaneous breathing route for the patient. The combination of labeling and an alert patient may obviate any real safety concern; however, providing a relief mechanism may provide some significant benefit and convenience to the users, and significantly improve efficacy of the therapy, or may be a significant benefit during product misuse, or during unanticipated clinical events.

SUMMARY OF THE INVENTION

The current invention is an improvement over existing ventilation interfaces and ventilation modes. The invention may include a ventilation interface with a spontaneous breathing flow path such that the patient can breathe ambient air freely through the interface if needed, and in the event of an obstruction, the patient is provided an alternate route of inspiring and/or exhaling. The invention may also include providing pressure and flow relief mechanisms in the ventilation interface to avoid undesirable lung pressures or to maintain desired lung pressures.

In one embodiment, the invention provides a ventilation apparatus comprising a ventilator, a gas delivery circuit, a transtracheal prosthesis or catheter, a respiratory relief device, and at least one respiratory sensor; and wherein the one or more respiratory sensor is adapted to detect an obstruction of the airway, or adapted to predict an obstruction of the airway when the obstruction is developing; and further wherein the respiratory relief device is adapted to open when the obstruction is detected or predicted.

In another embodiment, the invention provides a ventilation apparatus comprising (a) a ventilator; (b) a transtracheal prosthesis operably connected to the ventilator and arranged such that a patient using the ventilation apparatus can breathe freely through the patient's upper airway; and (c) a respiratory relief device; wherein the respiratory relief device is located proximal to the patient and is adapted to allow a patient using the ventilation apparatus to exhale to ambient, to inhale from ambient, or both through the tracheal prosthesis.

In another embodiment, the invention provides a ventilation apparatus comprising (a) a ventilator; (b) a gas delivery circuit operably connected to the ventilator; (c) a ventilation catheter operably connected to the gas delivery circuit; (d) the ventilator adapted to provide a pulse of gas to the patient through the ventilation catheter during inspiration by the patient; (e) a transtracheal prosthesis, wherein the ventilation catheter is placed coaxially in the transtracheal prostheses; and wherein the transtracheal prostheses and ventilation catheter are arranged such that a patient using the ventilation apparatus can breathe freely through the patient's upper airway; (f) one or more respiratory sensor adapted to measure the patient's breathing rate, lung pressure, airway pressure, or a combination thereof; and to determine when the patient inspires; (g) a respiratory relief device; wherein the respiratory relief device is located proximal to the patient and is adapted to allow a patient using the ventilation apparatus to exhale to ambient, to inhale from ambient, or both through the tracheal prosthesis; wherein the respiratory relief device has an open state and a closed state; (h) the one or more respiratory sensor is adapted to calculate to calculate a normal breathing rate for the patient, a normal lung pressure for the patient, a normal airway pressure for the patient, or a combination thereof; (i) the respiratory relief device is adapted to be provided in a closed state while the one or more breath sensor detects that the patient is breathing with the normal breathing rate, normal lung pressure, normal airway pressure, or a combination thereof; (j) the one or more respiratory sensor is adapted to detect a variation in the patient's breathing rate from the normal breathing rate, a variation in the patient's lung pressure from the normal lung pressure, a variation in the patient's airway pressure from the normal airway pressure, or a combination thereof; and (k) the respiratory relief device is adapted to open or be opened in response to detection of the variation.

In another embodiment, the invention provides a ventilation apparatus comprising (a) a ventilator; (b) a gas delivery circuit operably connected to the ventilator; (c) a transtracheal prosthesis operably connected to the gas delivery circuit; wherein the transtracheal prostheses and is arranged such that a patient using the ventilation apparatus can breathe freely through the patient's upper airway; (d) a ventilator configured to provide a pulse of gas to the patient through the transtracheal prosthesis during inspiration by the patient; (e) one or more one or more respiratory sensor adapted to measure a patient's breathing rate, lung pressure, airway pressure, or a combination thereof; and to determine when the patient inspires; (f) a respiratory relief device; wherein the respiratory relief device is located proximal to the patient and is configured to allow a patient using the ventilation apparatus to exhale to ambient, to inhale from ambient, or both through the tracheal prosthesis; (g) the respiratory relief device has an open state and a closed state; (h) one or more respiratory sensor is adapted to calculate to calculate a normal breathing rate for the patient, a normal lung pressure for the patient, a normal airway pressure for the patient, or a combination thereof; (i) the respiratory relief device is adapted to be provided in a closed state while the one or more breath sensor detects that the patient is breathing with the normal breathing rate, normal lung pressure, normal airway pressure, or a combination thereof; (j) the one or more respiratory sensor is adapted to detect a variation in the patient's breathing rate from the normal breathing rate, a variation in the patient's lung pressure from the normal lung pressure, a variation in the patient's airway pressure from the normal airway pressure, or a combination thereof; and (k) the respiratory relief device is adapted to open or be opened in response to detection of the variation.

In another embodiment, the invention provides a ventilation apparatus comprising (a) a ventilator adapted to (i) provide a pulse of gas to the patient during inspiration by a patient, wherein the pulse has a first volume; (ii) provide pulses of gas to a patient after detection of a cessation of breathing or reduction in breathing volume of the patient, wherein the pulses each have a second volume and wherein (1) the pulses are provided at a rate that is 1-5 times the normal breathing rate, (2) the second volume is 25-500% greater than the first volume, or (3) the pulses are provided at a rate that is 1-5 times the normal breathing rate and the second volume is 25-500% greater than the first volume; (b) a gas delivery circuit operably connected to the ventilator; (c) one or more respiratory sensor adapted to determine when the patient inspires, to calculate a normal breathing volume for the patient, to detect a cessation of breathing or reduction in breathing volume of the patient; (d) a respiratory relief device, wherein the respiratory relief device is configured to allow the patient to exhale to atmosphere.

In another embodiment, the invention provides a method of providing ventilation to a patient comprising providing a ventilation that provides transtracheal, open, inspiratory-synchronized, augmented ventilation; further comprising providing pressure or flow relief by providing at least one opening in the ventilation apparatus to ambient air at the ventilation interface in the event of an airway obstruction; and further comprising allowing the patient to breathe spontaneously through a transtracheal component of the ventilation apparatus.

In another embodiment, the invention provides a method of providing ventilation to a patient comprising (a) providing a ventilation apparatus comprising (i) a ventilator; (ii) a gas delivery circuit operably connected to the ventilator; (iii) a ventilation catheter operably connected to the gas delivery circuit; (iv) a transtracheal prosthesis placed in the trachea of the patient, wherein the ventilation catheter enters the patient's trachea through the transtracheal prostheses; and wherein the transtracheal prostheses and ventilation catheter are arranged such that the patient can breathe freely through the patient's upper airway; (v) one or more respiratory sensor adapted to measure the patient's breathing rate, lung pressure, airway pressure, or a combination thereof; and (vi) a respiratory relief device; wherein the respiratory relief device is located proximal to the patient and is configured to allow the patient to exhale to ambient, to inhale from ambient, or both through the tracheal prosthesis; and wherein the respiratory relief device has an open state and a closed state; (b) using the one or more respiratory sensor to determine when the patient inspires; (c) providing a pulse of gas to the patient through the ventilation catheter during inspiration by the patient; (d)

using the one or more respiratory sensor to measure the patient's breathing rate, lung pressure, airway pressure, or a combination thereof; (e) using the one or more respiratory sensor to calculate a normal breathing rate for the patient, a normal lung pressure for the patient, a normal airway pressure for the patient, or a combination thereof; (f) providing said respiratory relief device in a closed state while the one or more breath sensor detects that the patient is breathing with the normal breathing rate, normal lung pressure, normal airway pressure, or a combination thereof; (g) using the one or more respiratory sensor to detect a variation in the patient's breathing rate from the normal breathing rate, a variation in the patient's lung pressure from the normal lung pressure, a variation in the patient's airway pressure from the normal airway pressure, or a combination thereof; and (h) opening said respiratory relief device in response to detection of the variation.

In another embodiment, the invention provides a method of providing ventilation to a patient comprising (a) providing a ventilation apparatus comprising (i) a ventilator; (ii) a gas delivery circuit operably connected to the ventilator; (iii) a transtracheal prosthesis operably connected to the gas delivery circuit; wherein the transtracheal prosthesis is placed in the trachea of the patient; and wherein the transtracheal prosthesis and ventilation catheter is arranged such that the patient can breathe freely through the patient's upper airway; (v) one or more respiratory sensor adapted to measure the patient's breathing rate, lung pressure, airway pressure, or a combination thereof; and (vi) a respiratory relief device; wherein the respiratory relief device is located proximal to the patient and is configured to allow the patient to exhale to ambient, to inhale from ambient, or both through the tracheal prosthesis; (b) using the one or more respiratory sensor to determine when the patient inspires; (c) providing a pulse of gas to the patient through the ventilation catheter during inspiration by the patient; (d) providing a respiratory relief device according to claim 1N, further wherein the respiratory relief device has an open state and a closed state; (e) using the one or more respiratory sensor to measure the patient's breathing rate, lung pressure, airway pressure, or a combination thereof; (f) using the one or more respiratory sensor to calculate a normal breathing rate for the patient, a normal lung pressure for the patient, a normal airway pressure for the patient, or a combination thereof; (g) providing said respiratory relief device in a closed state while the one or more breath sensor detects that the patient is breathing with the normal breathing rate, normal lung pressure, normal airway pressure, or a combination thereof; (h) using the one or more respiratory sensor to detect a variation in the patient's breathing rate from the normal breathing rate, a variation in the patient's lung pressure from the normal lung pressure, a variation in the patient's airway pressure from the normal airway pressure, or a combination thereof; and (i) opening said respiratory relief device in response to detection of the variation.

In another embodiment, the invention provides a method of providing ventilation to a patient comprising (a) using a breath sensor to determine when the patient inspires; (b) providing a pulse of gas to the patient during inspiration by the patient, wherein the pulse has a first volume; (c) using the breath sensor to calculate a normal breathing volume for the patient; (d) providing a respiratory relief device, wherein the respiratory relief device is configured to allow the patient to exhale to atmosphere; (e) detecting a cessation of breathing or reduction in breathing volume of the patient; (f) after detecting a cessation of breathing or reduction in breathing volume of the patient, providing pulses of gas to the patient, wherein the pulses each have a second volume and wherein (i) the pulses are provided at a rate that is 1-5 times the normal breathing rate, (ii) the second volume is 25-500% greater than the first volume, or (iii) the pulses are provided at a rate that is 1-5 times the normal breathing rate and the second volume is 25-500% greater than the first volume.

Non-limiting examples of gas delivery circuits include dual limb breathing circuits, single limb breathing circuits, single limb ventilation gas delivery circuits, and small caliber ventilation gas delivery circuits.

Non-limiting examples of transtracheal prostheses include tracheal tubes, tracehostomy tubes, airway guides, catheter guides, tracheal prostheses, stoma guides, stoma stents, stents, outer cannulae, airway prostheses, tracheal stents, tracheal T-tubes, cricothyrotomy tubes, and other guiding structures.

Non-limiting examples of respiratory relief devices include breathing circuit ambient flow ports, ambient inspiratory relief valves, ambient expiratory relief valves, inspiratory relief valves, expiratory relief valves, ambient flow ports, secondary ambient flow ports, active valves, passive valves, inspiratory relief diaphragms, expiratory relief diaphragms, inflatable valves, deflatable valves, inflatable/deflatable valves, spring loaded valves, valves with electromechanical actuators, electromagnetic valves, and combinations thereof. A respiratory relief device may be always open, or opened or closed as desired or opened or closed in response to certain conditions.

When describing the location of a respiratory relief device, "proximal to the patient" may include locations between a tracheal prosthesis and ventilation catheter, locations within a tracheal prosthesis, locations that form part of or are integral to a tracheal prosthesis or ventilation catheter, and locations that form a part of or are integral to a catheter connector.

Non-limiting examples of respiratory sensors include intra-tracheal sensors, such thermal sensors, airway pressure sensors, impedance sensors, airflow sensors, neurological or muscular activity sensors, respiratory gas sensors, oximetry sensors, breath sensors, and combinations thereof. Respiratory sensors may be, as non-limiting examples, positioned in the trachea (intra-tracheal), positioned in a transtracheal prosthesis, positioned outside the patient and connected to an airflow channel within the gas delivery circuit lumen, or positioned outside the patient and connected to an airflow channel separate from the gas delivery circuit.

In embodiments of the invention, the gas delivery may optionally be synchronized with the patient's breathing cycle by use of a respiratory sensor(s). Preferably, the ventilator may provide augmented volume to the patient during the inspiratory breath phase of the patient. In embodiments of the invention, the gas delivery may optionally comprise Jet airflow dynamics, such as with exit speeds above 150 m/sec from the catheter.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTIONS OF THE FIGURES

The accompanying drawings, which are included to provide a further understanding of the invention and are incorporated in and constitute a part of this specification, illustrate preferred embodiments of the invention and together with the detailed description serve to explain the principles of the invention. In the drawings:

FIG. 9A illustrates a side view partial cross section of a portion of an open ventilation system with a ventilation gas delivery catheter and ambient flow ports that are always open.

FIG. 9B illustrates an end cross sectional view of FIG. 9A at line F-F.

FIG. 10A illustrates a side view partial cross section of a portion of an open ventilation system with ventilation gas delivery catheter and a passive exhalation pressure relief valve.

FIG. 10B illustrates an end cross sectional view of FIG. 10A at line H-H.

Figure 18A:
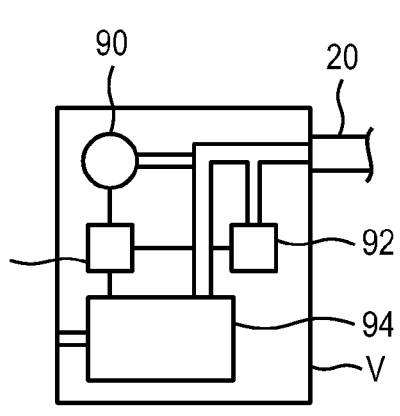

FIG. 18A a illustrates a portion of an open ventilation system with an inflation and deflation control system for an active inspiratory and expiratory relief valve.

Figure 18B:
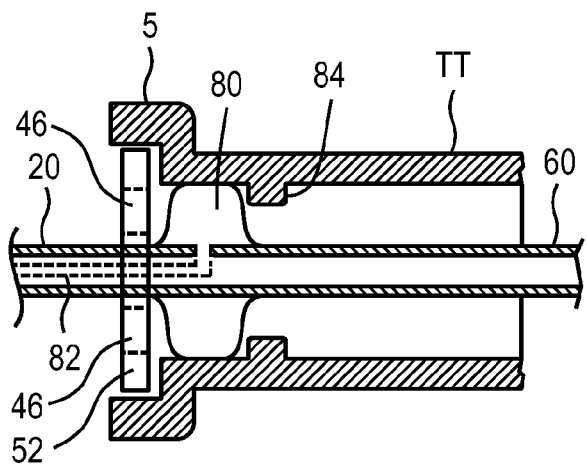

FIG. 18B illustrates a side view partial cross section of a portion of an active inspiratory and expiratory relief valve that acts by inflation and deflation.

Figure 18C:
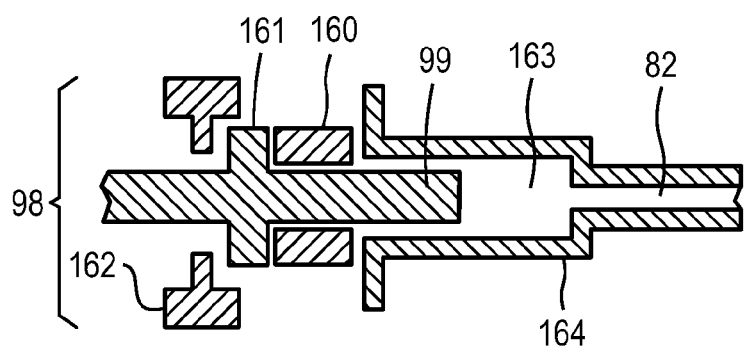

FIG. 18C illustrates a side view cross section of a piston mechanism for controlling an inflatable active inspiratory and expiratory relief valve.

Figure 19:
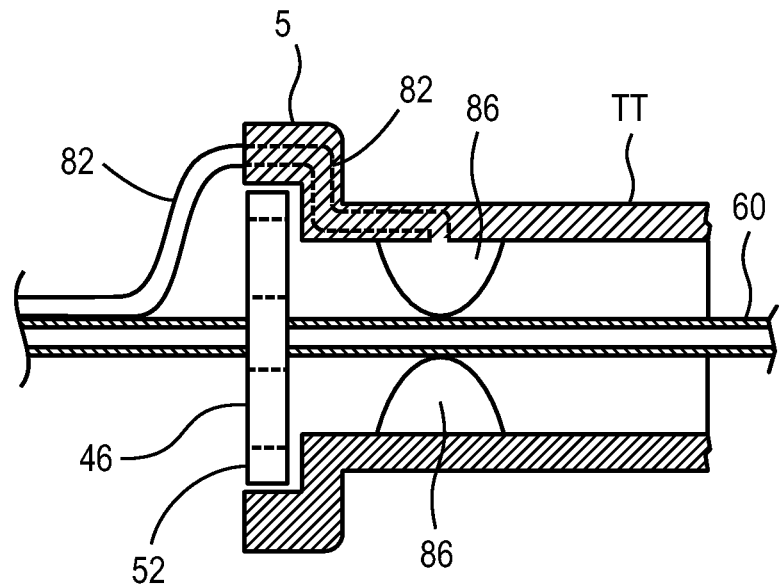

FIG. 19 illustrates a side view partial cross section of a portion of an open ventilation system with an active inspiratory and expiratory relief valve that acts by inflation and deflation of a valve element.

Figure 20:
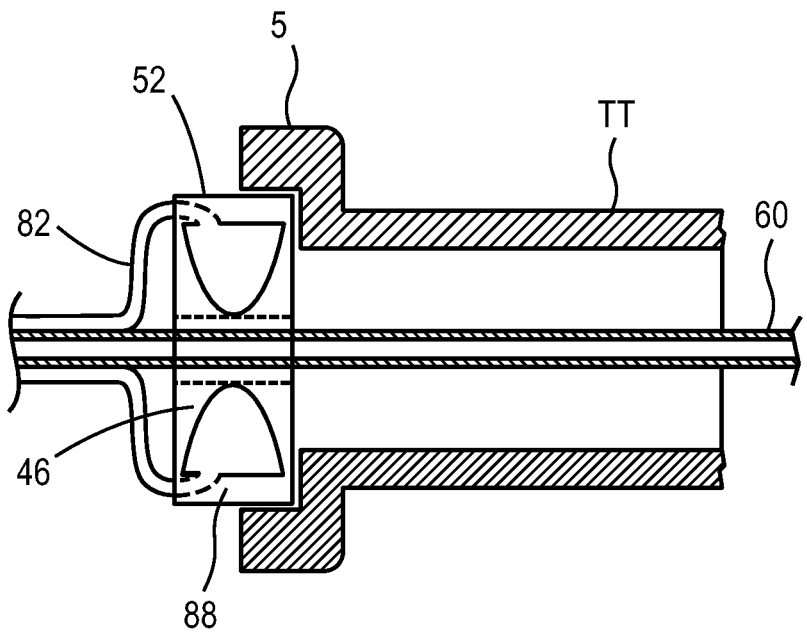

FIG. 20 illustrates a side view partial cross section of an open ventilation system with an active inspiratory and expiratory relief valve that acts by inflation and deflation of a valve element.

Figure 21:
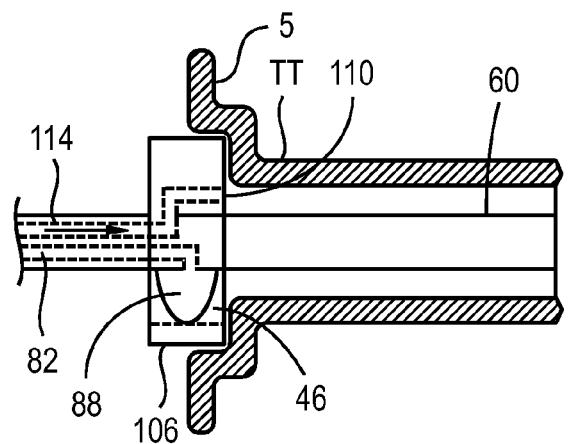

FIG. 21 illustrates a side view partial cross section of a portion of an open ventilation system with an active inflatable inspiratory and expiratory relief valve and a separate lung pressure monitoring line.

Figure 22A:
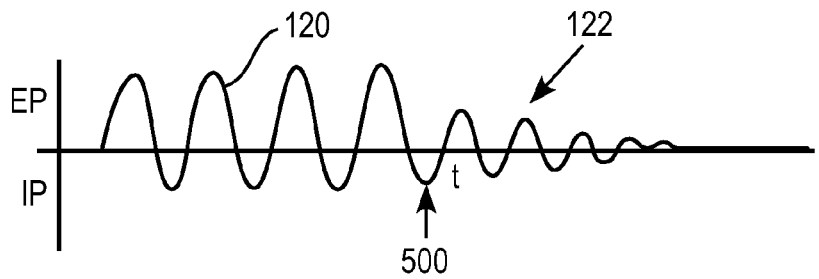

FIG. 22A graphically illustrates the breath signal appearance in an open ventilation system before and after an obstruction.

Figure 22B:
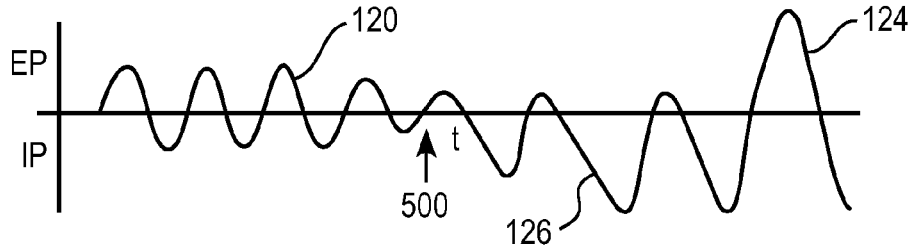

FIG. 22B graphically illustrates the lung pressure signal appearance in an open ventilation system before and after an obstruction.

Figure 22C:
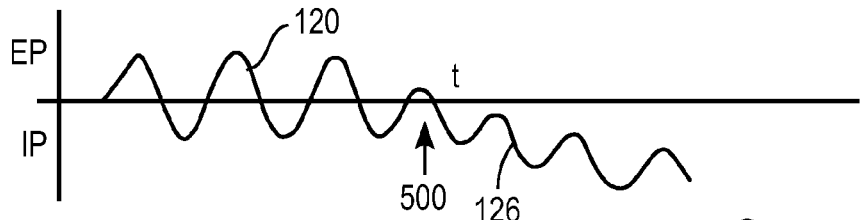

FIG. 22C graphically illustrates the lung pressure signal appearance in an open ventilation system before and after an obstruction.

Figure 22D:
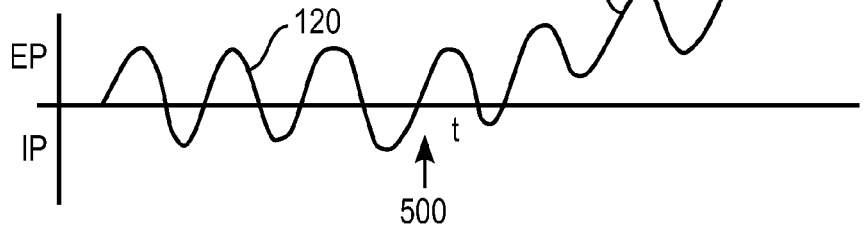

FIG. 22D graphically illustrates the lung pressure signal appearance in an open ventilation system before and after an obstruction.

Figure 23:
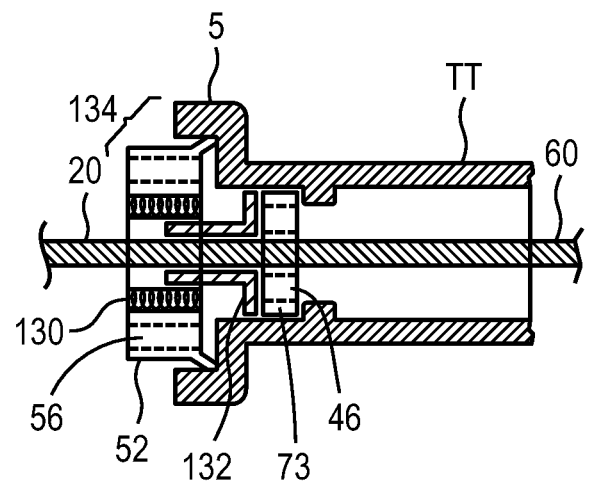

FIG. 23 illustrates a side view cross section of a portion of an open ventilation system with an active inspiratory and expiratory relief valve with an electromechanical valve actuator.

Figure 24:
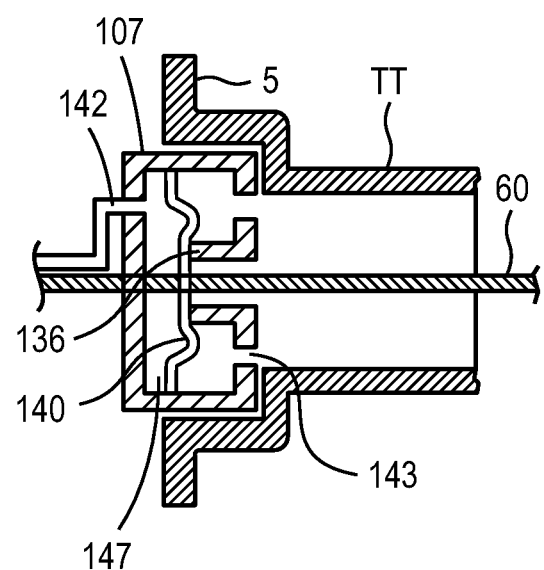

FIG. 24 illustrates a side view cross section of a portion of an open ventilation system with an active inspiratory and expiratory relief valve with a pilot signal controlling the pressure relief.

Figure 25A:
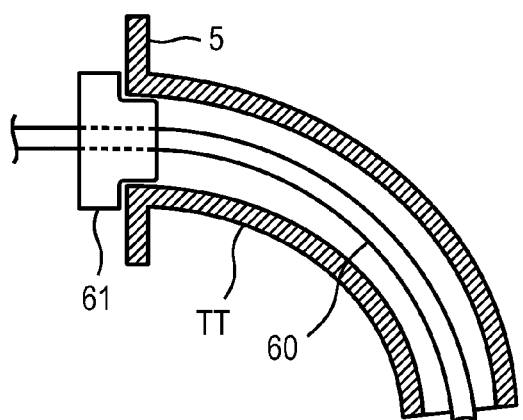

FIG. 25A illustrates a side view partial cross section of a portion of an open ventilation system with a ventilation gas delivery catheter occupying minimal space within the tracheal tube.

Figure 25B:
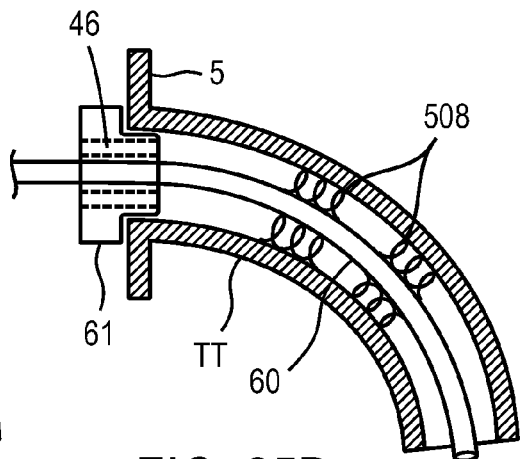

FIG. 25B illustrates an alternative to the catheter of FIG. 25A, in which the catheter is stabilized within the tracheal tube with coils.

Figure 25C:
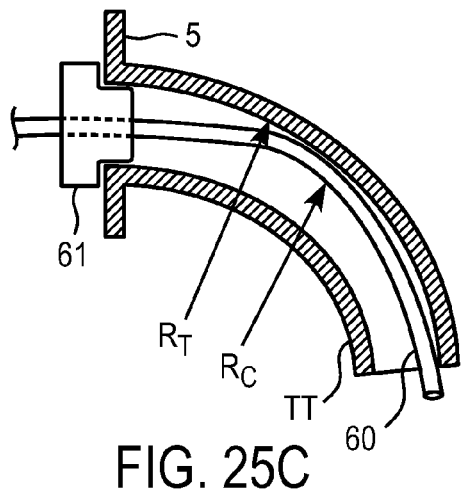

FIG. 25C illustrates an alternative to the catheter of FIG. 25A, in which the catheter is stabilized within the tracheal tube by a curve forcing it against the superior inside wall of the tracheal tube.

Figure 25D:
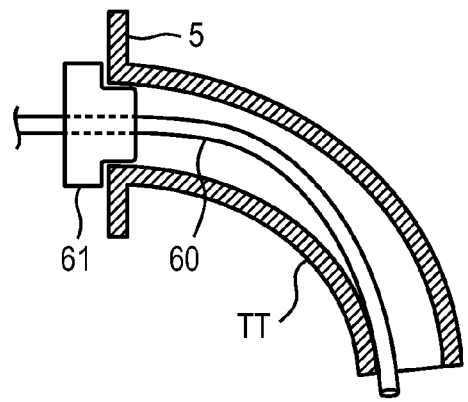

FIG. 25D illustrates an alternative to the catheter of FIG. 25A, in which the catheter is stabilized within the tracheal tube by a curve forcing it against the inferior inside wall of the tracheal tube.

Figure 25E:
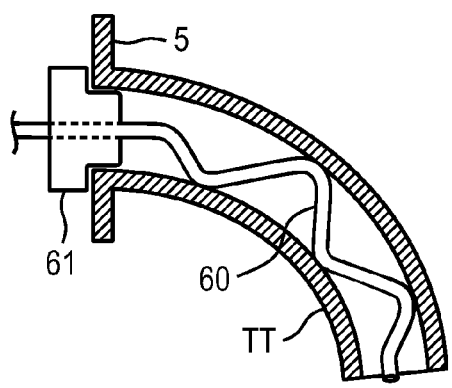
Figure 26A:
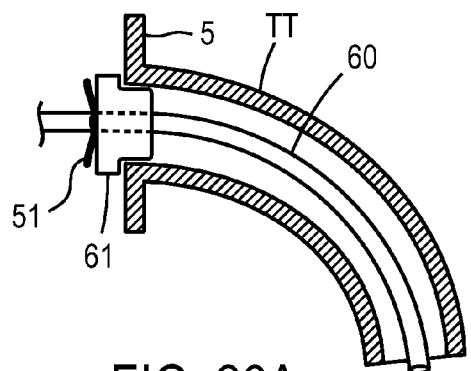

FIG. 25E illustrates an alternative to the catheter of FIG. 25A, in which the catheter is stabilized within the tracheal tube by multiple curves forcing it against the inside wall of the tracheal tube FIG. 26A illustrates a side view partial cross section of a portion of an open ventilation system with a relief valve located at the proximal end of the tracheal tube.

Figure 26B:
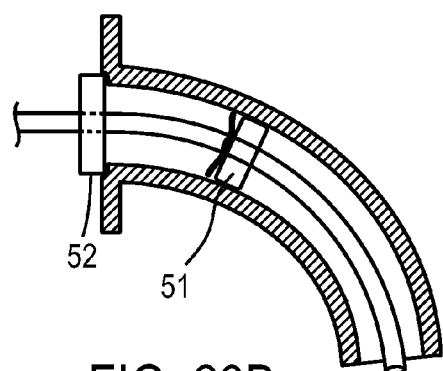

FIG. 26B illustrates a side view partial cross section of a portion of an open ventilation system with a relief valve located in the midsection of the tracheal tube.

Figure 26C:
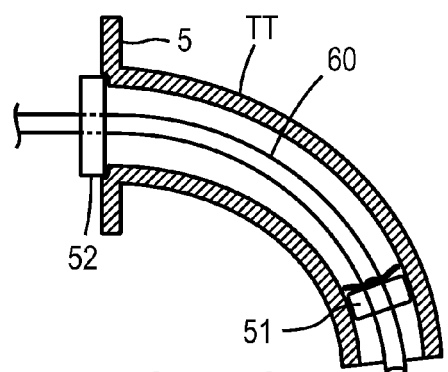

FIG. 26C illustrates a side view partial cross section of a portion of an open ventilation system with a relief valve located near the distal end of the tracheal tube.

Figure 26D:
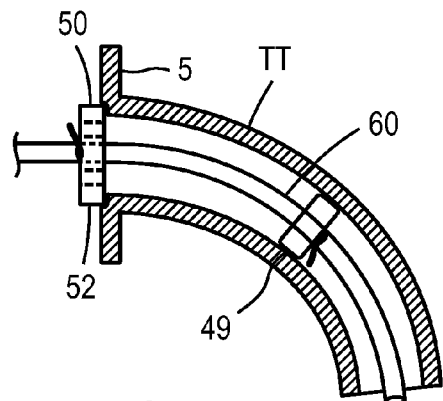

FIG. 26D illustrates a side view partial cross section of a portion of an open ventilation system with multiple relief valves located in the midsection and proximal end of the tracheal tube.

Figure 27:
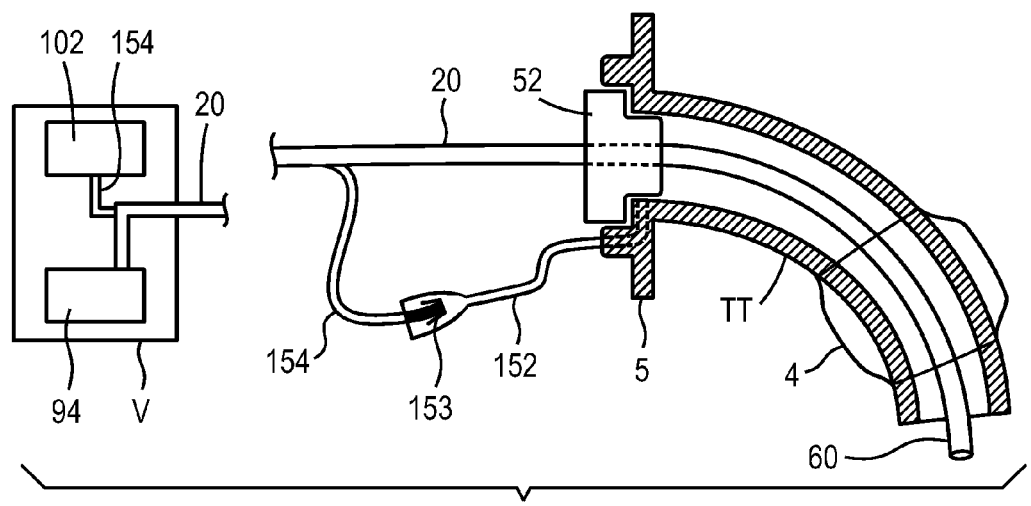

FIG. 27 illustrates portions of an open ventilation system with an active cuff deflation system.

Figure 28:
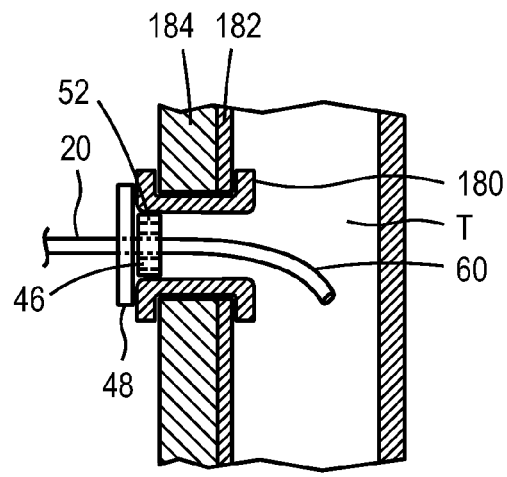

FIG. 28 illustrates a side view partial cross section of a portion of an open ventilation system with a passive expiratory relief valve, in which the gas delivery catheter is placed into a stoma guide or stent.

Figure 29A:
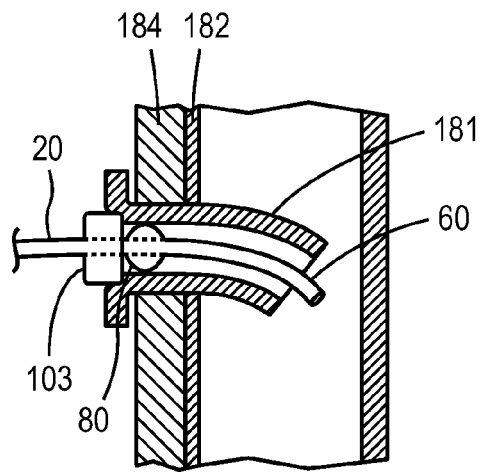

FIG. 29A illustrates a side view partial cross section of a portion of an open ventilation system with an active inspiratory and expiratory relief valve, in which the gas delivery catheter is placed into a stoma stent.

Figure 29B:
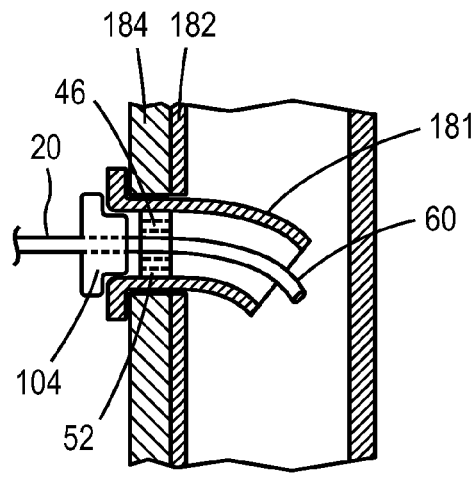

FIG. 29B illustrates a side view partial cross section of a portion of an open ventilation system with a passive inspiratory and expiratory relief valve, in which the gas delivery catheter is placed into a stoma guide.

Figure 29C:
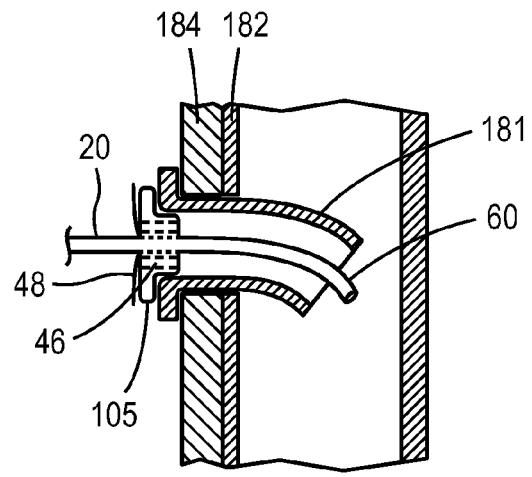

FIG. 29C illustrates a side view partial cross section of a portion of an open ventilation system with a passive expiratory relief valve, in which the gas delivery catheter is placed through the valve and into a stoma guide.

Figure 30A:
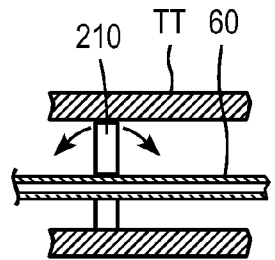

FIG. 30A illustrates a cross sectional side view of an alternative relief valve, wherein the mechanism is a leaf valve.

Figure 30B:
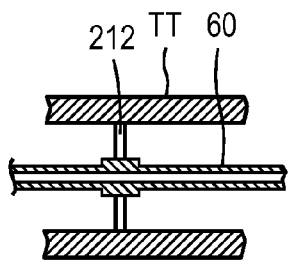

FIG. 30B illustrates a cross sectional side view of an alternative relief valve, wherein the mechanism is a diaphragm valve.

Figure 30C:
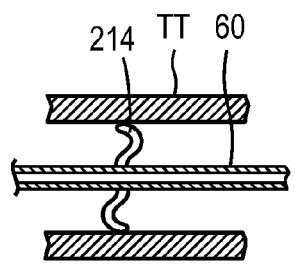

FIG. 30C illustrates a cross sectional side view of an alternative relief valve, wherein the mechanism is a convoluted diaphragm valve.

Figure 30D:
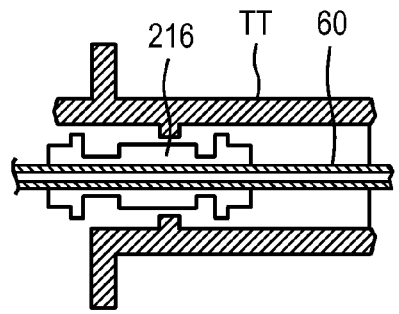

FIG. 30D illustrates a cross sectional side view of an alternative relief valve, wherein the mechanism is a poppet valve.

Figure 30E:
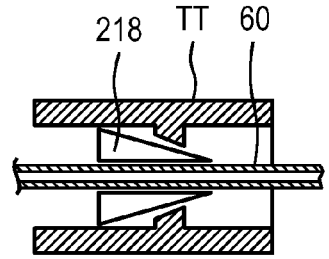

FIG. 30E illustrates a cross sectional side view of an alternative relief valve, wherein the mechanism is a duck billed valve.

Figure 30F:
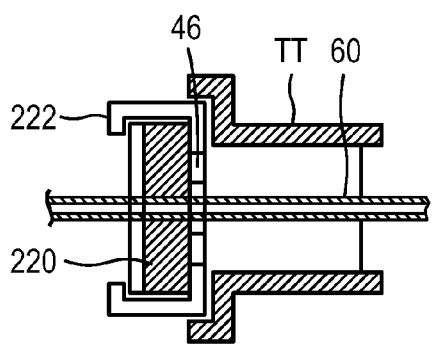

FIG. 30F illustrates a cross sectional side view of an alternative relief valve, wherein the mechanism is a spring element valve.

Figure 30G:
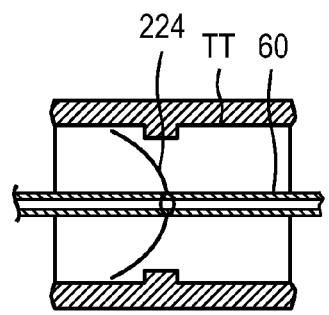

FIG. 30G illustrates a cross sectional side view of an alternative relief valve, wherein the mechanism is an umbrella valve.

Figure 30H:
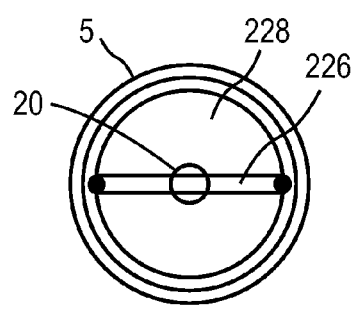

FIG. 30H illustrates an end view of an alternative relief valve, where the mechanism is a hinged leaflet valve.

Figure 30I:
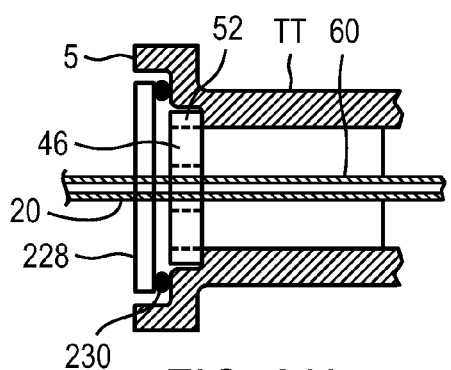

FIG. 30I illustrates a cross sectional side view of the valve in FIG. 30H.

Figure 31:
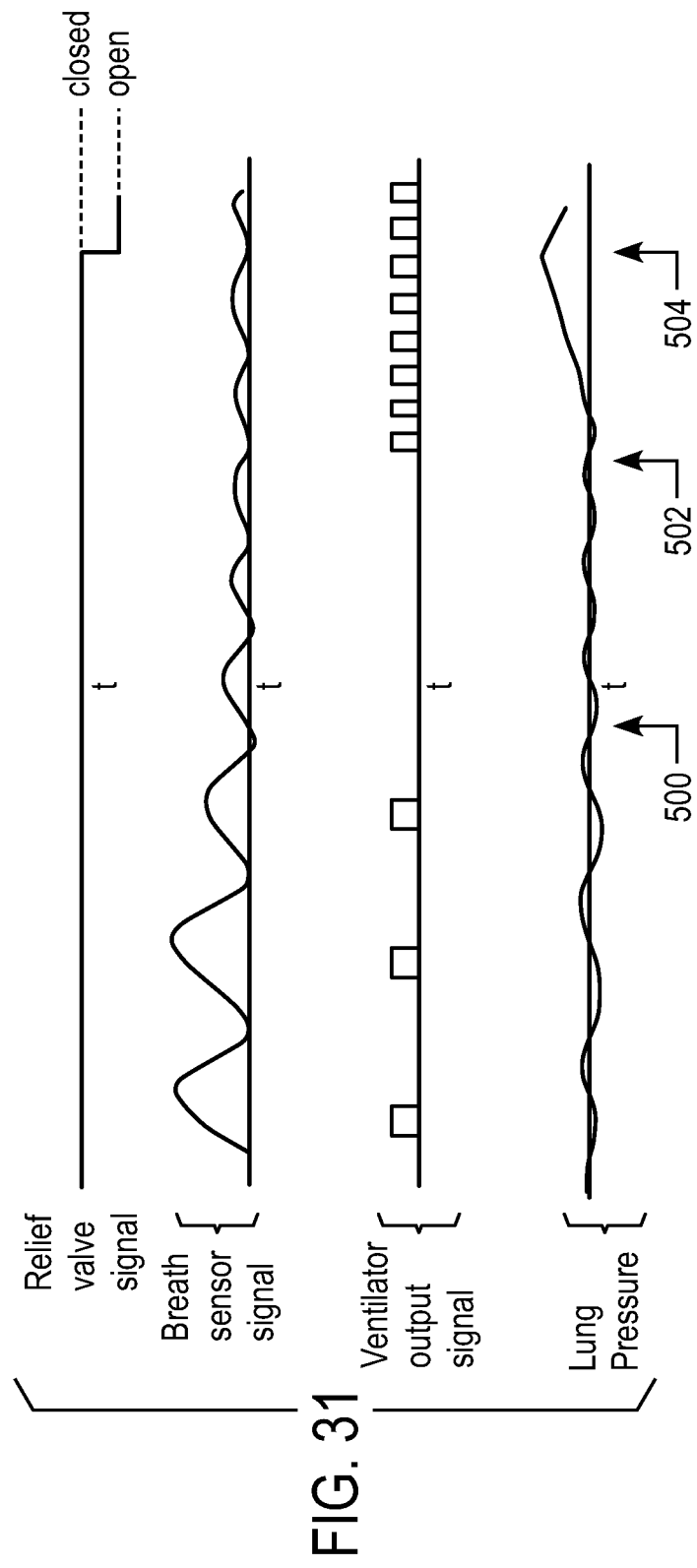

FIG. 31 graphically illustrates tidal volumes and lung pressures before and after an apneic event or an obstruction, and with an apnea or back up rate mode and an active or passive expiratory relief valve.

Figure 32:
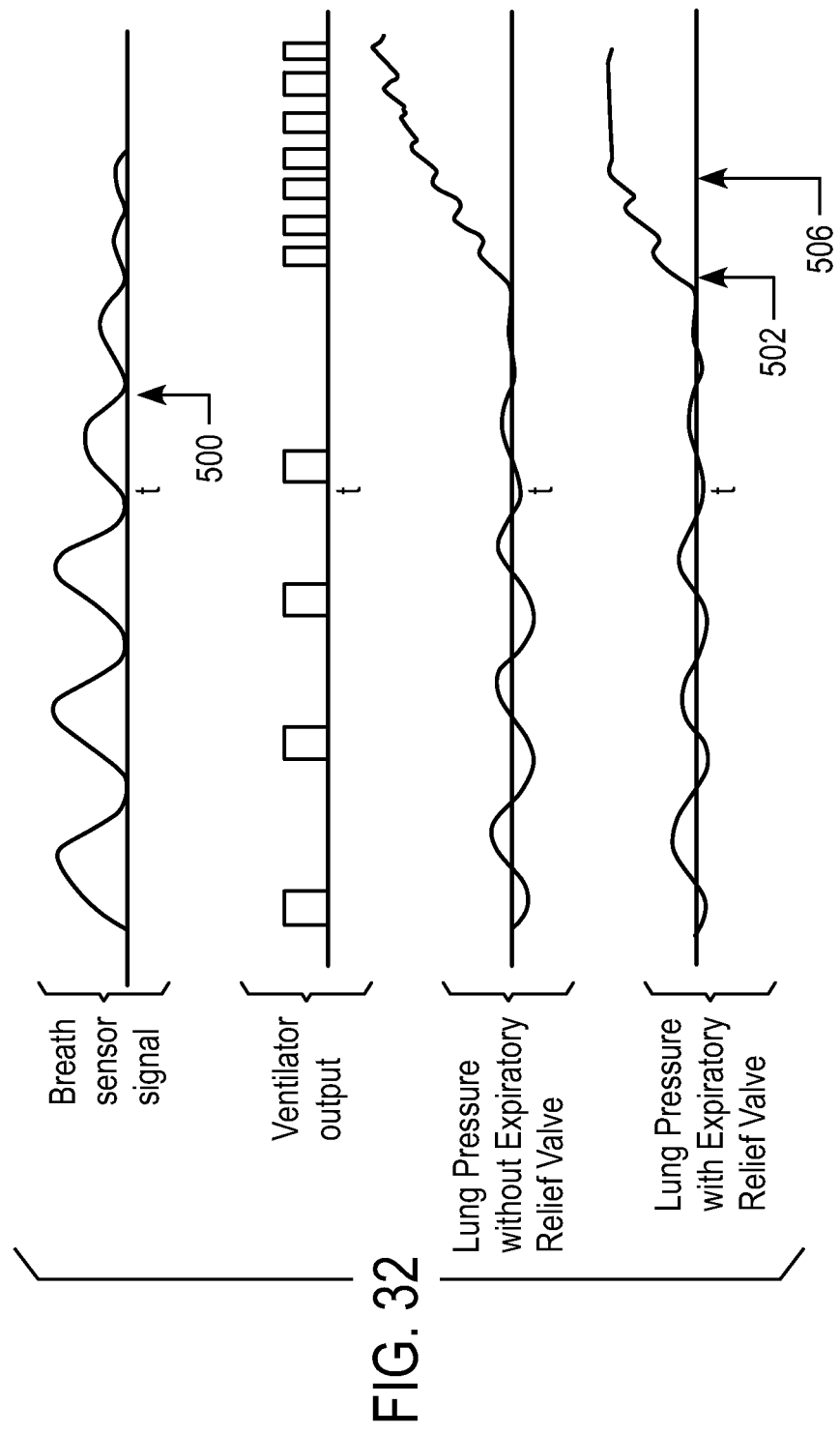

FIG. 32 graphically illustrates tidal volumes and lung pressures before and after an apneic event or an obstruction, and with an apnea or back up rate mode, with and without a relief valve.

LIST OF REFERENCE SYMBOLS USED IN THE FIGURES

A ventilator gas output
V ventilator delivery circuit
P Patient
T trachea
IL inspiratory limb
EL expiratory limb
ETT endotracheal tube ports
UA upper airway
TT tracheal tube or tracheostomy tube
I inspiratory flow
E expiratory flow
IP inspiratory pressure
EP expiratory pressure
t time axis
2 dual limb breathing circuit
4 tracheal tube cuff
5 tracheal tube flange/connector
8 inspiratory relief valve
10 expiratory relief valve
12 single limb breathing circuit
14 NIV mask ports
16 NIV mask
19 a single limb ventilation gas
20 small caliber ventilation gas
22 exhalation valve
30 UA obstruction/restriction
32 OA obstruction/restriction
36 breathing circuit ambient flow
38 ambient expiratory relief valve
40 ambient inspiratory relief valve
42 ambient inspiratory/expiratory relief valve
46 ambient flow ports
46A ambient flow ports
46B ambient flow ports
46C ambient flow ports
46D ambient flow ports
46E ambient flow ports
46F ambient flow ports
48 expiratory relief diaphragm
49 inspiratory relief valve
50 expiratory relief valve
51 inspiratory/expiratory relief pressure valve
52 catheter connector pressure
53 catheter connector pressure
54 inspiratory relief diaphragm
56 secondary ambient flow ports inspiratory vacuum
60 transtracheal ventilation catheter
61 catheter connector
62 expiratory diaphragm seat
64 inspiratory diaphragm seat relief valve
72 seat
73 seat
80 inflatable valve element
82 valve inflation/deflation channel
84 valve seat 86 inflatable/deflatable valve
88 inflatable/deflatable valve
90 pressure transducer
92 inflation/deflation mechanism
94 gas delivery mechanism
98 piston mechanism
99 piston
100 relief valve
102 vacuum source
103 sealing connector
104 sealing connector
105 sealing connector
106 catheter connector
107 catheter connector
110 sensing channel
114 purge flow
120 normal spontaneous breathing
122 reduced spontaneous breathing
124 increased spontaneous expiratory
126 increased spontaneous
130 valve actuator
132 sliding valve diaphragm
134 active inspiratory and expiratory
136 valve seat
140 convoluted diaphragm
142 pilot pressure signal line
143 airway pressure signal line
147 valve chamber
152 cuff inflation line
153 inflation line plug
154 cuff vacuum line
160 return spring
161 piston flange
162 piston stop
163 cylinder chamber
164 cylinder housing
170 processor
180 stoma stent
181 stoma guide
182 tracheal wall
184 neck
200 intra-tracheal respiration sensor
210 disk valve
212 diaphragm valve
214 convoluted diaphragm
216 poppet valve
218 duck billed valve
220 spring
222 spring valve
224 umbrella diaphragm valve
226 leaflet valve hinge
228 valve leaflet
230 leaflet valve seal
500 time obstruction occurs
502 time back up rate begins
504 time active relief valve opens
506 time passive relief valve opens
508 catheter centering members

DETAILED DESCRIPTION OF THE PREFERRED EMBODIMENTS

Figure 1:
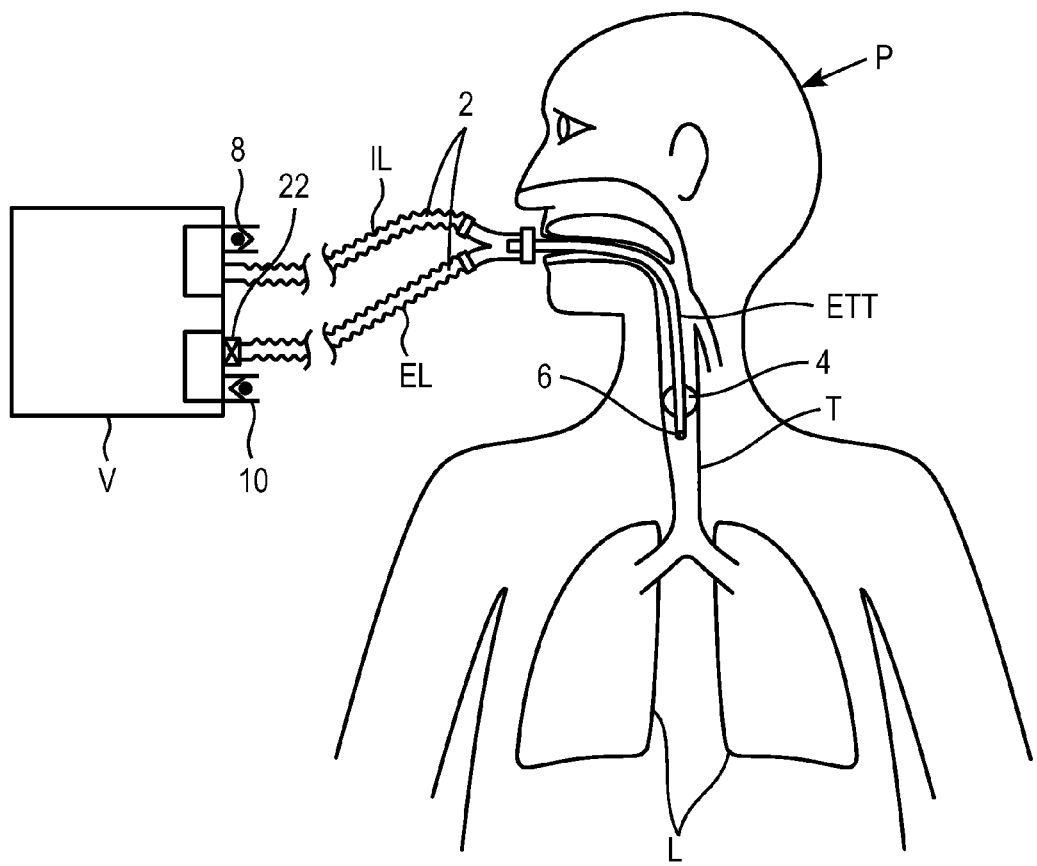
FIG. 1 illustrates a conventional, prior art, CMV closed ventilation system, typically used for full ventilatory support.

FIG. 1 illustrates a prior art conventional ventilation system, commonly known as a continuous mechanical ventilation (CMV) system, in which the ventilator (V) is connected to the patient (P) with a dual limb breathing circuit (2) and delivers gas to the patient via an inspiratory limb (IL), and gas is exhaled from the lung back an expiratory limb (IL) through an exhalation valve (22). A typical patient ventilation interface is an endotracheal tube (ETT) with a tracheal tube cuff (4), such that the patient's lungs are closed off from ambient air and are only connected to an air source through the ventilator breathing circuit. The ventilator in CMV systems typically includes one or more ambient relief valves to prevent over pressurization of the lung if an obstruction or high pressure event occurs and to enable access to ambient air if a ventilator failure occurs. The ventilator can include an inspiratory relief valve (8) so that the patient, if they have any breath effort capability, can open the inspiratory relief valve (8) and inspire ambient air through it. The ventilator can include an expiratory relief valve (10), so that if there is a dangerously high pressure being generated in the lungs due to an obstruction or malfunction, the expiratory relief valve (10) can open and exhaust gas to ambient.

Figure 2:
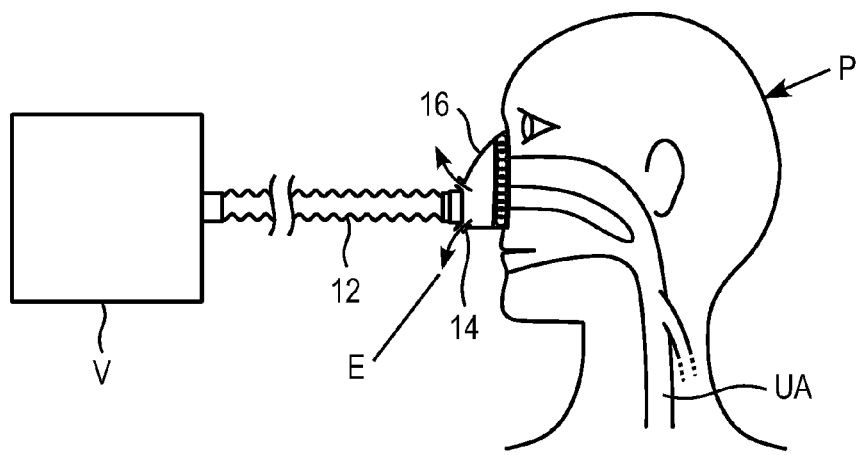
FIG. 2 illustrates a conventional, prior art, CPAP closed ventilation system, typically used for partial ventilatory support.

FIG. 2 illustrates a prior art conventional ventilation system including a ventilator (V), typically referred to as a Continuous Positive Airway Pressure (CPAP) system. There is a single limb breathing circuit (12) in the illustrated CPAP system, through which the patient inhales and exhales. All of the gas received by the patient is delivered by the CPAP ventilator. This system is also a closed ventilation system. The patient ventilation interface is typically a ventilation mask, commonly known as a non-invasive ventilation (NIV) mask (16) that is sealed against the patient's face, so that the respiratory system is closed to ambient air. Typically CPAP ventilation, with an NIV mask (16), is used when the patient at least some breath effort capability, but is still dependent on artificial ventilatory support. In this system, the patient receives gas supplied by the CPAP ventilator; i.e., the patient does not spontaneously breathe ambient air. CPAP systems include either (i) mask exhalation ports on the NIV mask (NIV mask ports (14)), so that exhalation through the breathing circuit can occur, or (ii) a valve in the breathing circuit or ventilator that permits exhalation. These ports or valves also serve as relief ports in the event of a malfunction of the ventilation system.

Figure 3:
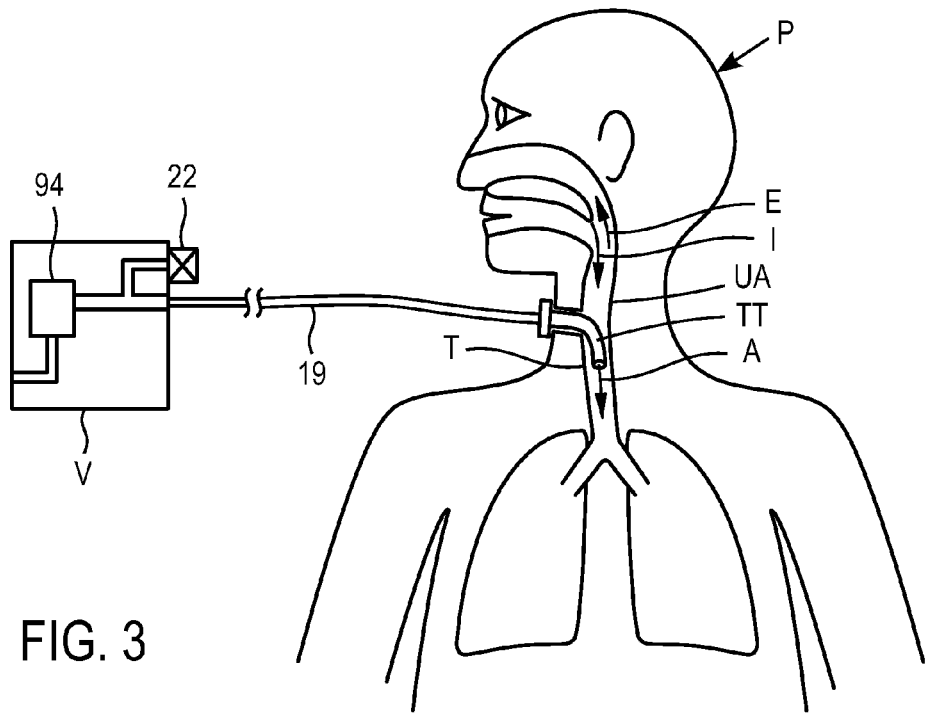
FIG. 3 illustrates an open ventilation system, typically used for augmenting the patient's spontaneous breathing with gas from the ventilator.

FIG. 3 illustrates an open ventilation system, in which the patient P is inspiring I and exhaling E ambient air naturally through their upper airway (UA). The patient ventilation interface can be a tracheostomy tube (TT), or a transtracheal catheter, which is typically connected to the ventilator (V) with a single limb ventilation gas delivery circuit (19) and a gas delivery mechanism (94). Non-limiting examples of gas delivery mechanisms include valves, pumps, accumulators, or pressurized gas supplies. The ventilator in this case provides ventilation assistance, or augmented ventilation, to the patient through a catheter (not shown), as illustrated by the ventilator gas output (A). If the internal dimensions of the components of the gas delivery circuit between the tracheostomy tube (TT) and ventilator's exhalation valve (22) are large enough in effective diameter, typically 8 mm effective diameter for an adult patient, the patient can exhale at least partially through the breathing circuit. If the internal dimensions of gas delivery circuit components are small than this diameter, the patient exhales predominantly or entirely through their upper airway. Exemplary open ventilation systems are described by Freitag in US Patent Application No. 2005/0034721 and by Wondka in US Patent Application No. 2005/0005936. For reasons of un-obtrusiveness and convenience to the user, or because of other performance factors such as ventilator gas delivery dynamics, in the open ventilation systems described in these applications, the gas delivery circuit components can in some cases be smaller than 4 mm in internal diameter, in which case the patient is expected to exhale predominantly through their natural breathing route (upper airway), and not through the gas delivery circuit.

Figure 4A:
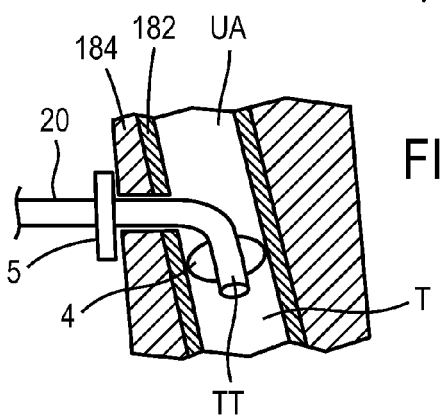
FIG. 4A illustrates a portion of an open ventilation system with an obstruction caused by an inadvertently inflated tracheostomy tube cuff.
Figure 4B:
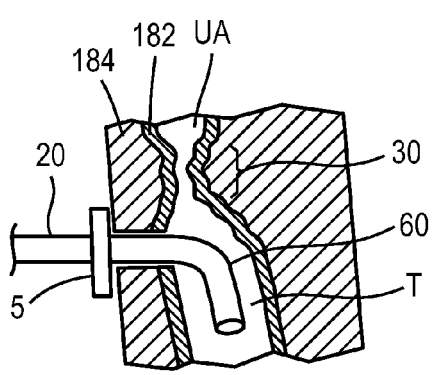
FIG. 4B illustrates a portion of an open ventilation system with an obstruction caused by stenosis or stricture of structures in the tracheal or laryngeal airway
Figure 4C:
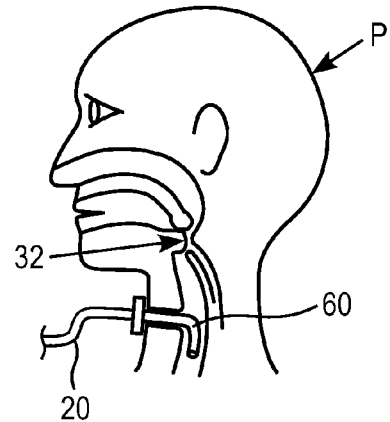
FIG. 4C illustrates a portion of an open ventilation system with an obstruction caused by swollen or collapsed tissues in the oropharyngeal airway.

FIGS. 4A-4C illustrate obstructions that can occur and that can compromise the function and safety of ventilation systems. In the embodiments that follow, the obstructions and the solutions described to mitigate them are described in the context of open ventilation systems; however, it should be recognized that many of the embodiments apply to closed ventilation systems as well, and one knowledgeable in the field will understand how to apply the embodiments to those systems. A tracheal tube (TT) or transtracheal ventilation catheter (60) is placed into the trachea (T) through the neck (184) and tracheal wall (182) and typically secured in place with a tracheal tube flange (5).

FIG. 4A illustrates a portion of an open ventilation system in which the patient ventilation interface is a cuffed tracheal tube (TT). It is necessary that the tracheal tube cuff (4) be deflated by the patient or clinician to administer open ventilation, and it is necessary that the cuff remain deflated during administration of open ventilation. If it is desired to switch to administration of closed ventilation, then the tracheal tube cuff (4) is inflated by the patient or clinician. However, as illustrated in FIG. 4A, the tracheal tube cuff (4) may accidentally or inadvertently be inflated when open ventilation is being administered, thus obstructing the airway of the patient.

FIG. 4B illustrates a portion of an open ventilation system in which the patient interface is, for example, a transtracheal ventilation catheter (60) as shown, or a tracheal tube (TT). As illustrated in FIG. 4B, the tracheal upper airway (UA) may develop an obstruction or restriction (30) due to, for example, spasmed or swollen vocal cords, or an airway stenosis, swelling, or stricture, such as could occur with, for example, tracheal malacia, an airway stent malfunction, a tumor growth, an injury, or an acute spasm or swelling.

FIG. 4C illustrates a portion of an open ventilation system in which the patient interface is, for example, a transtracheal ventilation catheter (60) as shown, or a tracheal tube (TT). As illustrated in FIG. 4C, the upper airway (UA) may develop a restriction or obstruction (32) in the oropharyngeal area, such as can occur, for example, in obstructive sleep apnea syndrome.

During trachea or upper airway obstruction events that can occur while administering open ventilation, such as those illustrated in FIGS. 4A-4C, the patient can no longer breathe adequately through their upper airway, and is therefore reliant on the ventilator for air and for a means to exhale. In the event that the ventilator is not capable of supplying enough volume to sustain respiration and/or the ventilator is not capable of allowing the patient to exhale through the ventilation gas delivery circuit, there is a need for a mechanism or mechanisms to be provided to allow the patient to inspire enough air from ambient, and/or to allow the patient to exhale air to ambient.

Figure 5:
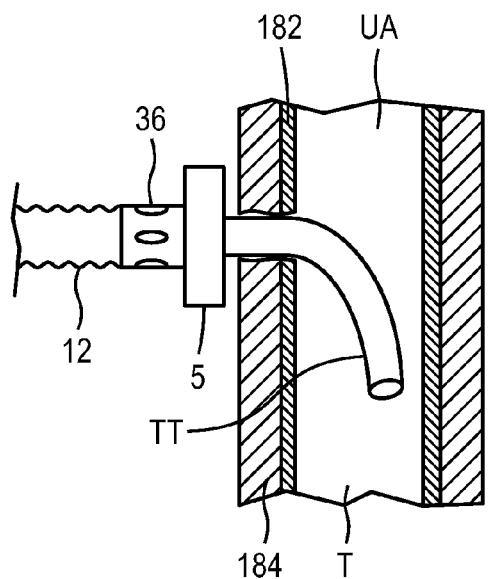
FIG. 5 illustrates a portion of an open ventilation system with a single limb breathing circuit that includes ambient breathing flow ports.

FIG. 5 illustrates a portion of an open ventilation system comprising a single limb breathing circuit (12) and breathing circuit ambient flow ports (36). The breathing circuit ambient flow ports (36) in the embodiment illustrated in FIG. 5 are always open, and the patient can inhale and exhale through these ports if the air flow through the upper airway (UA) becomes more restricted than the air flow through the ports. When the upper airway is unobstructed, only a small amount of air is breathed through the ports because they are selected to be more resistive to flow than the upper airway of the normal or typical patient, for example 2-5 times as resistive, so that breathing through the normal passages is encouraged, in order to maintain functions such as speech, smell, swallowing, etc. The ports may preferably be constructed so that their resistance is 3-50 cmH$_2$O/L/sec. More preferably, the ports may be constructed so that their resistance is 8-15 cmH$_2$O/L/sec. The ports may be a part of the gas delivery circuit, a part of the tracheal tube, or a part of a separate piece interconnecting the gas delivery circuit and tracheal tube. The flow resistance of the ports is determined by the size of the ports, and the ports are preferably of a size to provide the desired resistance. The tracheal tube can preferably be a 4-16 mm inner diameter ("ID") and 6-18 mm outer diameter ("OD") tube, or more preferably a 4-8 mm ID, 6-12 mm OD tube for adults. The tube can preferably be molded or extruded and formed and made from a thermoplastic material such as PVC, or can be a elastomeric material such as silicone.

Figure 6:
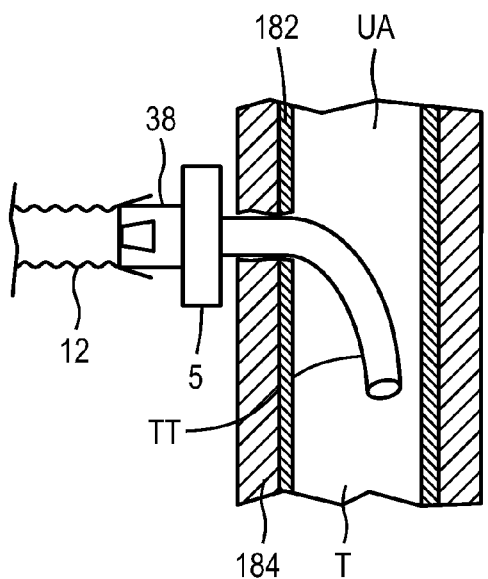
FIG. 6 illustrates a portion of an open ventilation system with a single limb breathing circuit and an expiratory relief valve shown in its open position.

FIG. 6 illustrates a portion of an open ventilation system comprising a single limb breathing circuit (12) and an ambient expiratory relief valve (38) shown in the open position. The ambient expiratory relief valve (38) shown in FIG. 6 typically is closed during normal operation of the ventilation system; however, when the patient cannot easily exhale through their upper airway, and exhalation pressure exceeds a desired level, such as a pressure above 10-40 cm H$_2$O, the ambient expiratory relief valve (38) opens, and the lungs can exhale to ambient through this valve. The ambient expiratory relief valve (38) can comprise diaphragm(s), leaf(s), or flap(s), that seal against a seat surrounding a port. The diaphragm(s), leaf(s), or flap(s) can be biased or preloaded with a force tending to keep them in the closed position. The diaphragm(s), leaf(s), or flap(s) thus have a cracking pressure, and is/are opened away from the seat to uncover, or open, the port when the cracking pressure is exceeded. The cracking pressure of expiratory valves or diaphragms used in embodiments of the present invention can preferably be 1 to 50 cmH$_2$O pressure, more preferably 5 to 50 cmH$_2$O, even more preferably 10 to 40 cmH2O, even more preferably 5 to 30 cmH$_2$O, even more preferably 20 to 25 cmH$_2$O, and most preferably 8 to 12 cmH$_2$O. The cracking pressure can also be adjustable, for example by tightening the valve against the seat. In valves such as shown in FIG. 5, the patient's breathing conditions, such as, for example, whether the patient has a restriction in their upper airway, control the state of the valve, i.e., open or closed. The valve's state is not controlled by an external mechanical system. This type of valve can be referred to as a "passive valve."

Figure 7:
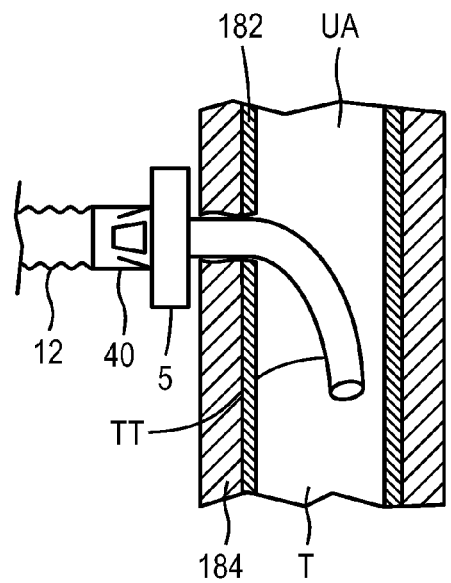
FIG. 7 illustrates a portion of an open ventilation system with a single limb breathing circuit and an inspiratory relief valve shown in its open position.

FIG. 7 illustrates a portion of an open ventilation system comprising a single limb breathing circuit (12) and an ambient inspiratory relief valve (40) shown in the open position. The ambient inspiratory relief valve (40) in illustrated in FIG. 7 typically is closed during normal operation of the ventilation system; however, when the patient can not inspire adequately through their upper airway, and the patient's lung pressure becomes more negative than a predetermined pressure, such as more negative than −6 to −20 cm H$_2$O, due to an increased effort by the patient to inspire, the ambient inspiratory relief valve (40) opens, and the patient can inspire ambient air through this valve. The components and operation of the ambient inspiratory relief valve (40) can be similar to the components and operation of the of ambient expiratory relief valve (38) shown in FIG. 6.

Figure 8:
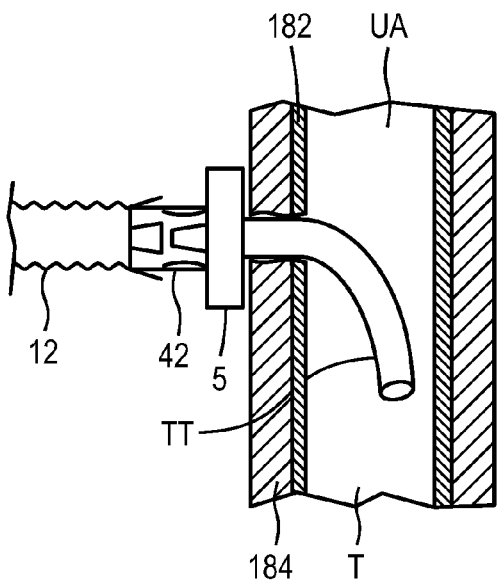
FIG. 8 illustrates a portion of an open ventilation system with single limb breathing circuit and combined inspiratory/expiratory relief valve with the expiratory shown it the closed position and the inspiratory shown in the closed position.

FIG. 8 illustrates a portion of an open ventilation system comprising a single limb breathing circuit (12) and an ambient inspiratory/expiratory relief valve (42), which combines the inspiratory and expiratory relief functions illustrated in FIGS. 6 and 7. In FIG. 8, the expiratory portion of the ambient inspiratory/expiratory relief valve (42) is located on the ventilator end of the valve and is shown open, while the inspiratory portion of the ambient inspiratory/expiratory relief valve

(42) is located on the patient end of the valve and is shown closed. The orientation of the inspiratory and expiratory portions is exemplary, and the ambient inspiratory/expiratory relief valve (42) may be constructed such that the inspiratory portion of the valve is located on the ventilator end of the valve, and the expiratory portion of the valve is located on the patient end of the valve. The components and operation of the each of the inspiratory and expiratory portions of the valve mechanism can be similar to the components and operation of the ambient expiratory relief valve (38) shown in FIG. 6 and the ambient inspiratory relief valve (40) shown in FIG. 7.

FIG. 9A illustrates a portion of an open ventilation system comprising a small caliber ventilation gas delivery circuit (20) and a transtracheal ventilation catheter (60) both shown in side view, and a tracheal tube (TT) shown in cross section. The small caliber ventilation gas delivery circuit (20) may have, for example, a 2-15 mm inner diameter channel for gas delivery. The small caliber ventilation gas delivery circuit (20) may preferably have a 3-5 mm inner diameter channel for gas delivery. Small caliber ventilation gas delivery circuit (20) may have a length that is preferably 20-100 inches, more preferably 30-40 inches. Small caliber ventilation gas delivery circuit (20) may have an outer diameter ("OD") of preferably 6-16 mm, more preferably 6-10 mm; and may have inner diameter ("ID") of preferably 2-10 mm, more preferably 3-5 mm. Transtracheal ventilation catheter (60) may be an end of small caliber ventilation gas delivery circuit (20); alternatively, transtracheal ventilation catheter (60) may be a separate component from small caliber ventilation gas delivery circuit (20), and the two may be operably connected using any art-known suitable method, such as via a catheter connector. The transtracheal ventilation catheter (60) may have, for example, a 1-5 mm diameter lumen for gas delivery. Transtracheal ventilation catheter (60) may preferably have an outer diameter ("OD") of 6-16 mm, more preferably 3-10 mm, more preferably 8-10 mm, most preferably 4-6 mm; and may preferably have an inner diameter ("ID"), or lumen diameter, of 0.75-3 mm, more preferably 1.5-2.5 mm, most preferably 1-2 mm. Transtracheal ventilation catheter (60) may have a length distal to the skin relative to the exterior of the patient that is preferably 10-200 mm, more preferably 20-100 mm. The annular gap between the transtracheal ventilation catheter (60) and tracheal tube (TT) is preferably 1-5 mm per side, more preferably 2-4 mm per side, and even more preferably 2.5-3.5 mm per side. The ambient flow ports (46) preferably have a cumulative cross sectional area of 8-20 mm$^2$, more preferably 10-12 mm$^2$. The resistance to airflow through the annular gap between the transtracheal ventilation catheter (60) and tracheal tube (TT) and ambient flow ports (46) is typically 2-20 cmH$_2$O/L/sec and preferably 5-15 cmH$_2$O/L/sec. Tracheal tube (TT) may have a length distal to the skin relative to the exterior of the patient that is preferably 10-200 mm, more preferably 20-100 mm. The transtracheal ventilation catheter (60) is preferably molded or extruded and formed typically from a thermoplastic material such as PVC, PVC urethane blends, or nylons or nylon blends, or molded using a elastomeric material such as silicone. The transtracheal ventilation catheter (60) material is preferably 60-90 shore A hardness, so that it resists kinking and bending. In the embodiment illustrated in FIG. 9A, the transtracheal ventilation catheter (60) is placed into tracheal tube (TT). However the transtracheal ventilation catheter (60) of this embodiment can be placed in other types of transtracheal cannulae or prostheses that provide an access port to the trachea. Non-limiting examples of transtracheal prostheses include tracheal tubes, tracehostomy tubes, airway guides, catheter guides, tracheal prostheses, stoma guides, stoma stents, stents, outer cannulae, airway prostheses, tracheal stents, tracheal T-tubes, cricothyrotomy tubes, and other guiding structures. The embodiment illustrated in FIG. 9A, comprises ambient flow ports (46) in the catheter connector (61) that connects the transtracheal ventilation catheter (60) to the tracheal tube. The ports are open to ambient and to the tracheal tube, and the patient can breathe through these ports through the tracheal tube if air flow through the upper airway becomes more restricted than the air flow through the ports. The inspiratory air flow and expiratory relief air flow occurs in the annular gap between the transtracheal ventilation catheter (60) and tracheal tube (TT) and through the ambient flow ports (46) that are part of the catheter connector (61). When the upper airway is unobstructed, only a small amount of air is breathed through the ports because they are more resistive than the upper airway, for example 2-5 times as resistive, as previously explained. An intra-tracheal respiration sensor (200) is shown as being integral to the transtracheal ventilation catheter (60). The signal from the sensor synchronizes the ventilator output with the patient's spontaneous breathing, as desired; for example, triggering the ventilator to provide a pulse of gas to the patient at a certain point within the inspiratory cycle. The sensor signal also provides an indication of the pressure or flow in the patient's trachea and lung, which is useful in providing the user or ventilator control system information about obstructions, for example, a weakening airflow signal would indicate an obstruction, or a strengthening pressure signal would also indicate an obstruction. FIG. 9B describes an end cross sectional view of the small caliber ventilation gas delivery circuit (20), the ambient flow ports (46A), the catheter connector (61), the ambient flow ports (46), and the tracheal tube flange (5). Ambient flow ports (46A), as well as ambient flow ports (46B), (46C), (46D), (46E), and (46F) (shown in FIGS. 10B, 15B, 16C, 16D, and 16E, respectively), are each types of ambient flow port (46); and each of these types of ambient flow ports, as well as other suitable shapes and configurations, and combinations thereof, can be used with any embodiments of the invention.

Non-limiting examples of respiratory (or respiration) sensors include intra-tracheal sensors, such thermal sensors, airway pressure sensors, impedance sensors, airflow sensors, neurological or muscular activity sensors, respiratory gas sensors, oximetry sensors, breath sensors, and combinations thereof. Respiratory sensors may be, as non-limiting examples, positioned in the trachea (intra-tracheal), positioned in a transtracheal prosthesis, positioned outside the patient and connected to an airflow channel within the gas delivery circuit lumen, or positioned outside the patient and connected to an airflow channel separate from the gas delivery circuit. More specific, non-limiting examples include thermal sensor positioned in the tracheal lumen and an airway pressure sensor positioned in the tracheal lumen or in the transtracheal prosthesis.

FIG. 10A illustrates a portion of an open ventilation system comprising a small caliber ventilation gas delivery circuit (20) and a transtracheal ventilation catheter (60). In this embodiment, the transtracheal ventilation catheter (60) is placed into a tracheal tube (TT), for example. As with the embodiment of FIGS. 9A-9B, the transtracheal ventilation catheter (60) of this embodiment can be placed in other types of transtracheal cannulae or prostheses that provide an access port to the trachea. The transtracheal ventilation catheter (60) comprises an expiratory relief valve (50) which comprises an expiratory relief diaphragm (48) that closes ambient flow ports (46) during inspiration, but can open the ambient flow ports (46) during exhalation if the requisite conditions are met. If the patient experiences difficulty in exhaling due to an obstruction or malfunction, causing lung pressure to exceed a desired level, such as above 10-40 cmH$_2$O, the pressure flexes the expiratory relief diaphragm (48) such that the diaphragm moves away from catheter connector 61, which acts as expiratory diaphragm seat (62), thereby moving or flexing away from the ambient flow ports (46), thereby opening the ambient flow ports (46) and allowing the patient to exhale to ambient through the ports. FIG. 10B illustrates a cross section of FIG. 10A, showing the ambient flow ports (46), the expiratory diaphragm seat (62), and the tracheal tube flange (5). The expiratory relief diaphragm (48) can be comprised of, for example, an elastomeric membrane capable of flexing away from the expiratory diaphragm seat (62) in response to the desired pressure. The expiratory relief diaphragm (48) can be preloaded against expiratory diaphragm seat (62) during the free state so that it applies a light compression force against the seat, such that there are no inadvertent leaks near its cracking pressure, or can be shaped in a manner that tensions it against the seat during the free state. The seat section of the expiratory relief valve (50) is connected to the tracheal tube flange (5) with a friction fit. Expiratory relief diaphragm (48) is preferably fabricated of an elastomeric material, such as rubber, silicone, or other synthetic rubber-type material, and is typically 0.005-0.020 inches in thickness. A non-limiting example of a suitable material for the diaphragm is thermoplastic vulcanizate (TPV), such as that marketed as Santropene. The expiratory relief diaphragm (48) also may be a thermoplastic material, such as plasticized PVC, or PVC-urethane blends. Expiratory relief diaphragm (48) may be extruded as a sheet, then die cut to the desired final dimensions. Preferably, expiratory relief diaphragm (48) is molded. Preferably, expiratory relief diaphragm (48) comprises a slightly curved surface, which is useful for preloading the diaphragm in the closed state. Expiratory relief diaphragm (48) preferably overlaps with expiratory diaphragm seat (62). Preferably the overlap is 0.5-3 mm, more preferably 1.0-2.0 mm. Generally, diaphragms used in embodiments of the invention seat against another structure. The structure against which a diaphragm seats may be referred to herein as "expiratory diaphragm seat (62)" or "inspiratory diaphragm seat (64)". In certain cases, one part of a single structure may serve as expiratory diaphragm seat (62), while another part serves as inspiratory diaphragm seat (64).

Figure 11:
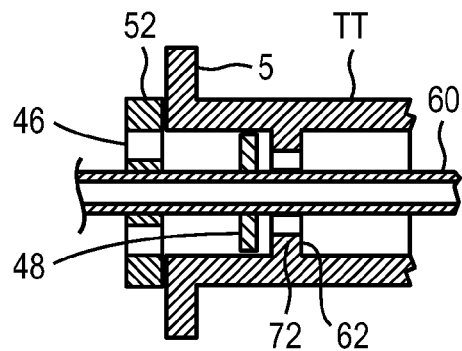
FIG. 11 illustrates a side view partial cross section of a portion of an open ventilation system with a passive ambient expiratory pressure relief valve.

FIG. 11 illustrates an axial cross section of a portion of an open ventilation system comprising a transtracheal ventilation catheter (60), a tracheal tube (TT), and an expiratory relief valve that comprises a expiratory relief diaphragm (48) attached to the transtracheal ventilation catheter (60), and a seat (72) that acts as an expiratory diaphragm seat (62) on the inner wall of the tracheal tube (TT). The expiratory relief diaphragm (48) comprises, for example, an elastomeric membrane attached to the wall of the transtracheal ventilation catheter (60). The transtracheal ventilation catheter (60) comprises a catheter connector (52) connecting it to the tracheal tube (TT). The catheter connector (52) has ambient flow ports (46) therethrough. In the embodiment illustrated in FIG. 11, the valve requires a mating of features between the transtracheal ventilation catheter (60) and tracheal tube (TT). The dimensions of the transtracheal ventilation catheter (60), catheter connector (52), and expiratory relief diaphragm (48) act together to position the expiratory relief diaphragm (48) such that it exerts a light pressure or tension against the expiratory diaphragm seat (62). The light pressure or tension, which may be, for example 0.05-0.1 pounds per square inch, defines the opening pressure of the valve. The expiratory relief diaphragm (48) will open in the direction of exhalation if the pressure against the valve exceeds its opening pressure, such as if 10-40 cm H$_2$O pressure is exerted against the valve. When the valve is open, expiratory relief air flow occurs in the annular gap between the transtracheal ventilation catheter (60) and tracheal tube (TT) and through the ambient flow ports (46).

Figure 12:
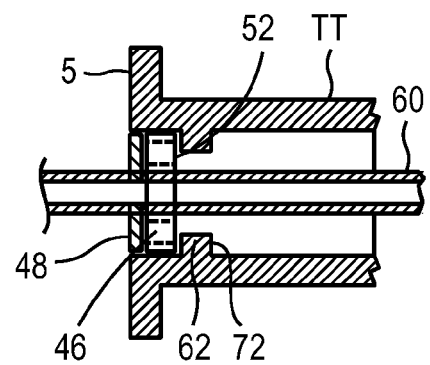
FIG. 12 illustrates a side view partial cross section of a portion of an open ventilation system with a passive ambient expiratory pressure relief valve.

It is important to note that the invention includes valves that are fully integral to the transtracheal ventilation catheter (60) only, valves that are fully integral to the tracheal tube (TT) only, valves that a part of both the catheter and tracheal tube, and valves that are separate from both the catheter and tracheal tube. For example, FIG. 12 illustrates an axial cross section of a portion of another open ventilation system. In this embodiment, the expiratory relief diaphragm (48) is attached to the transtracheal ventilation catheter (60), and the diaphragm seats against the catheter connector (52). The catheter connector (52) includes ambient flow ports (46). The catheter connector (52) seats inside the tracheal tube (TT) and seats against a seat (72) that acts as an expiratory diaphragm seat (62). When the opening pressure of the valve is reached, the diaphragm moves or flexes away from the valve seat, and air flows from the patient through the ambient relief flow ports.

Figure 13:
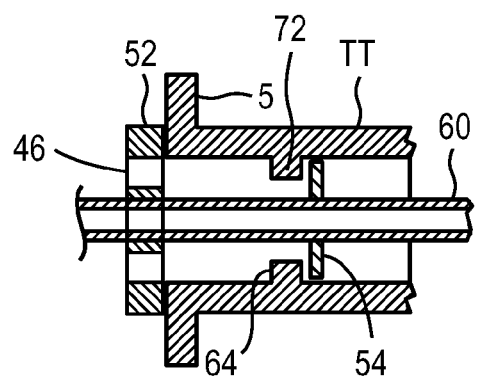
FIG. 13 illustrates a side view partial cross section of a portion of an open ventilation system with a passive ambient inspiratory relief valve.
Figure 14:
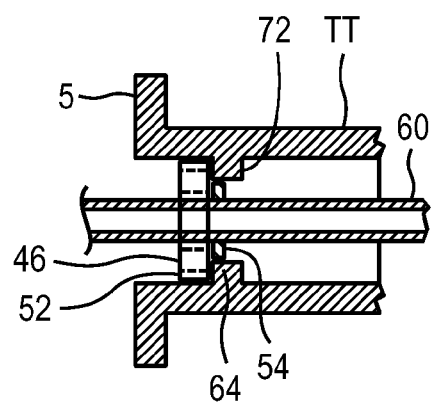
FIG. 14 illustrates a side view partial cross section of a portion of an open ventilation system with a passive ambient inspiratory relief valve.

FIG. 13 illustrates an axial cross section of a portion of an open ventilation system comprising an inspiratory relief valve. The system comprises a transtracheal ventilation catheter (60), a tracheal tube (TT), an inspiratory relief diaphragm (54) attached to the transtracheal ventilation catheter (60) and sealing against a seat (72) on the inner wall of the tracheal tube (TT); seat (72) acts as an inspiratory diaphragm seat (64). A catheter connector (52) attaches to the tracheal tube flange (5) to dimensionally position the transtracheal ventilation catheter (60) and inspiratory relief diaphragm (54) in the correct position, relative to the inspiratory diaphragm seat (64). The catheter connector includes ambient flow ports (46). The inspiratory relief diaphragm (54) will flex away from the inspiratory diaphragm seat (64) in the direction of inspiration if the cracking pressure of the valve is exceeded, such as below −6 to −20 cmH$_2$O, which can occur when the patient experiences difficulty with inspiring, thus increasing the negative pressure in the airway. The cracking pressure of inspiratory valves or diaphragms used in embodiments of the present invention can preferably be −5 to −50 cmH$_2$O, more preferably −10 to −40 cmH$_2$O, more preferably −10 to −20 cmH$_2$O, and most preferably −6 to −15 cmH$_2$O. In this embodiment, the valve requires a mating of features between the transtracheal ventilation catheter (60) and tracheostomy tube (TT); however it is important to note that the invention includes valves that are fully integral to the ventilation catheter only, valves that are fully integral to the tracheostomy tube only, and valves that are part of both the catheter and outer tube. For example, FIG. 14 illustrates an axial cross section of a portion of another open ventilation system comprising an inspiratory pressure relief valve wherein the inspiratory relief diaphragm (54), a seat (72) that acts as an inspiratory diaphragm seat (64), and ambient flow ports (46) are part of the construction of the transtracheal ventilation catheter (60). The catheter connector (52) comprises ambient flow ports (46), and is seated against a seat (72) that acts as an inspiratory diaphragm seat (64). An inspiratory relief diaphragm (54) is positioned on the patient side of the catheter connector (52) and ambient flow ports (46), such that when the opening pressure of the valve is reached, the diaphragm moves or flexes in the direction of inspiration, thus allowing the patient to inspire ambient air through the ports and the annular space between the tracheal tube and catheter.

Figure 15A:
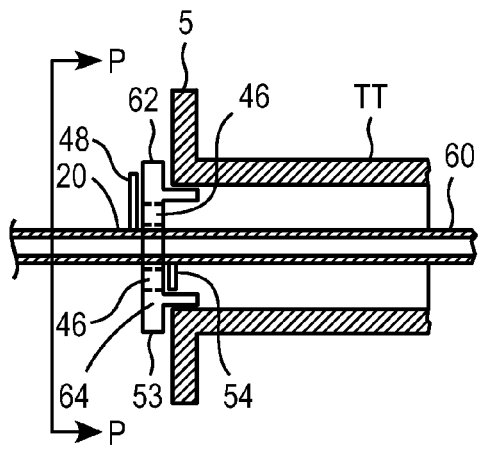
FIG. 15A illustrates a side view partial cross section of a portion of an open ventilation system with a passive combined ambient inspiratory and expiratory relief valve.
Figure 15B:
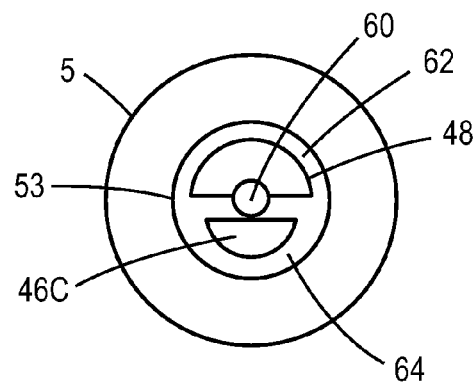
FIG. 15B illustrates a cross section of FIG. 15A at line P-P.

FIG. 15A illustrates an axial cross section of a portion of an open ventilation system comprising a combined inspiratory and expiratory relief valve. In this embodiment, the system comprises a transtracheal ventilation catheter (60) connected to a tracheal tube (TT) with a catheter connector (53) that comprises ambient flow ports (46). Catheter connector (53) acts as both inspiratory diaphragm seat (64) expiratory diaphragm seat (62). An inspiratory relief diaphragm (54) is positioned against an inspiratory diaphragm seat (64), and an expiratory relief diaphragm (48) positioned against an expiratory diaphragm seat (62). The inspiratory diaphragm seat (64) and expiratory diaphragm seat (62) are integral to the catheter connector (53). The inspiratory relief diaphragm (54) opens to allow the patient to inspire ambient air if other inspiration routes are unavailable or obstructed, and the expiratory relief diaphragm (48) opens to allow exhalation of gas from the patient if the airway pressure or lung reaches an undesirable level. The patient conditions required to open the valves, and the opening pressures of the valves are as previously described. FIG. 15B illustrates an end view of the catheter and tracheal tube described in FIG. 15A.

Figure 16A:
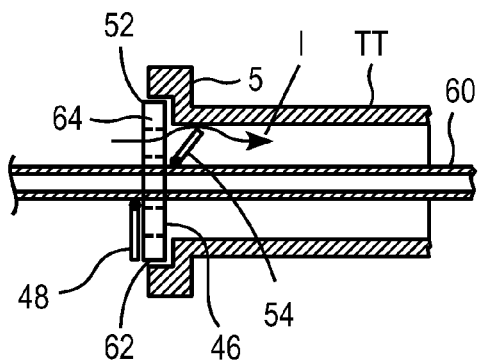
FIG. 16A illustrates a side view partial cross section of a portion of an open ventilation system with a passive combined inspiratory and expiratory relief valve and ambient flow ports, shown with the inspiratory relief valve open and the expiratory relief valve closed.
Figure 16B:
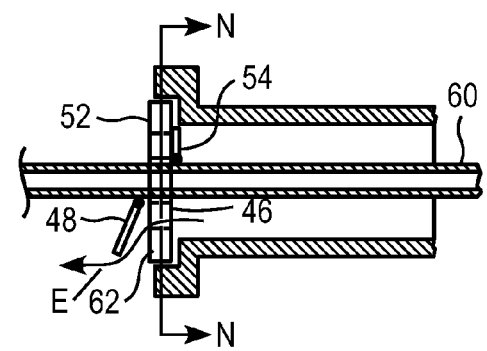
FIG. 16B illustrates a side view partial cross section of a portion of an open ventilation system with a passive combined inspiratory and expiratory relief valve and ambient flow ports, as illustrated in FIG. 16A shown with the expiratory relief valve open and the inspiratory relief valve closed.
Figure 16C:
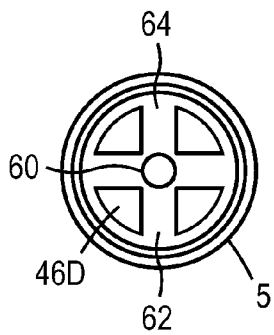
FIG. 16C illustrates an end cross sectional view of FIG. 16B at line N-N, showing the ambient flow port geometry of the valve.
Figure 16D:
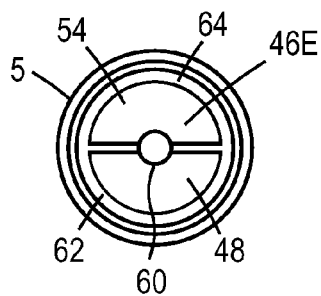
FIG. 16D illustrates an optional alternate ambient flow port geometry to the valve shown in FIG. 16C.
Figure 16E:
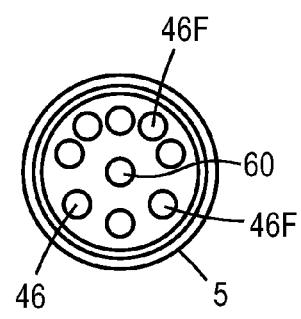
FIG. 16E illustrates an optional alternate ambient flow port geometry to the valve shown in FIG. 16C.

FIGS. 16A-16E illustrate the function and structure of a combined inspiratory and expiratory relief valve used in an open ventilation system. FIG. 16A illustrates axial cross section of a portion of an open ventilation system comprising a combined inspiratory and expiratory relief valve, showing the inspiratory relief valve in the open position and the expiratory relief valve in the closed position. The transtracheal ventilation catheter (60) includes a catheter connector (52) with ambient flow ports (46) with an inspiratory diaphragm seat (64) and an expiratory diaphragm seat (62) coaxial to the ambient flow ports (46). The inspiratory relief diaphragm (54) is shown connected to the catheter at its center and flexed open away from the center, allowing the patient to inspire ambient air through the valve and associated ambient flow port (46), and the expiratory relief diaphragm (48) is shown in the closed position against the valve seat, preventing any exhaled flow flowing through the valve and associated ambient flow port (46). FIG. 16B illustrates the axial cross section of the portion of the open ventilation system comprising a combined inspiratory and expiratory relief valve that is illustrated in FIG. 16A, but shows the inspiratory relief valve and inspiratory relief diaphragm (54) in the closed position and the expiratory relief valve and expiratory relief diaphragm (48) in the open position. FIGS. 16C-E illustrate end views of alternative exemplary embodiments of a combined inspiratory and expiratory relief valve. FIG. 16C shows the ambient flow ports (46D) configured in quadrants, with two of the quadrants associated with the inspiratory side of the valve and inspiratory diaphragm seat (64), and the other two quadrants associated with the expiratory side of the valve and the expiratory diaphragm seat (62). FIG. 16D illustrates a single ambient flow port (46E) for the inspiratory flow and a single ambient flow port (not shown, behind expiratory relief diaphragm (48), but of the same or similar size and shape as ambient flow port 46E) for the expiratory flow, with the inspiratory relief diaphragm (54) and inspiratory diaphragm seat (64) and expiratory relief diaphragm (48) and expiratory diaphragm seat (62) indicated. FIG. 16E illustrates multiple ambient flow ports (46F) in a pattern of tubes or holes, with more holes associated with the inspiratory side of the valve, and fewer holes associated with the expiratory side of the valve, in order to create less resistance to air flow in the inspiratory direction versus the expiratory direction. This later feature may be desirable in various applications, since inspiratory flow relief is often more urgent than expiratory flow relief, or since a slight positive pressure in the lung is sometimes desirable.

Figure 17A:
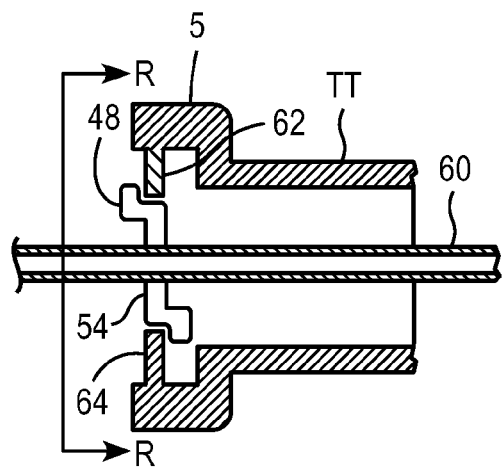
FIG. 17A illustrates a side view partial cross section of a portion of an open ventilation system with a combined passive inspiratory and expiratory relief valve, with the valve diaphragms overlapping with the valve seat.
Figure 17B:
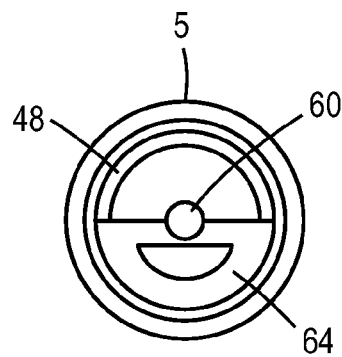
FIG. 17B illustrates an end cross sectional view of FIG. 17A at line R-R.

FIG. 17A illustrates an axial cross sectional view of a portion of an open ventilation system comprising a combined inspiratory and expiratory relief valve. A transtracheal ventilation catheter (60) is placed inside a tracheal tube (TT). The relief valve comprises an expiratory relief diaphragm (48) and an inspiratory relief diaphragm (54), each of which comprises a step so that it overlaps with the expiratory and inspiratory diaphragm seats (62, 64) in order to facilitate an effective seal and to bias the diaphragms in their closed positions. The inspiratory relief diaphragm (54) overlaps with the inspiratory diaphragm seat (64) and the expiratory relief diaphragm (48) overlaps with the expiratory diaphragm seat (62). As shown, the inspiratory and expiratory diaphragm seats (64, 62) are integral to the tracheal tube (TT) construction; alternatively, they can be part of the transtracheal ventilation catheter (60) construction or a separate assembly. FIG. 17B illustrates a cross sectional end view of the transtracheal ventilation catheter (60) and tracheal tube assembly, including the expiratory relief diaphragm (48) and the inspiratory diaphragm seat (64) and the tracheal tube flange (5) or connector.

FIGS. 18A and 18B illustrate portions of an open ventilation system comprising an active relief valve, which is opened by a mechanical source external to the patient, rather than the patient's inspiratory or expiratory effort or lung pressure conditions as in the previous examples. In the case of an active valve, versus a non-active or passive valve, a signal from a control system closes or opens the valve, based on a measurement being received from the patient and processed by the control system. Therefore, the cracking or opening pressure of an active valve is not an important design feature. Rather than opening when a cracking pressure is reached due to the patient's inspiratory effort or lung pressure, an active valve is opened by an external force. The control system makes a determination on when to open or close the valve, based on predetermined criteria and based on real time measurements of the patient's breathing and airway pressure, which may be determined using suitable art-known methods. The embodiment illustrated in FIGS. 18A and 18B comprises a small caliber ventilation gas delivery circuit (20), a transtracheal ventilation catheter (60) placed inside a tracheostomy tube (TT), and a pressure or flow relief valve. The pressure or flow relief valve comprises a valve seat (84), an inflatable valve element (80), a catheter connector (52) with ambient flow ports (46), a valve inflation/deflation channel (82), and an inflation/deflation mechanism (92) inside the ventilator (V). In the embodiment illustrated in FIG. 18B, the relief valve is an inflatable valve element (80); however, this inflatable valve is only exemplary, and other forms of active valves can be used in the invention. Non-limiting examples of other active valves include spring loaded valves, valves with electromechanical actuators, and electromagnetic valves. In the case of an inflatable relief valve, such as is illustrated in FIG. 18B, the transtracheal ventilation catheter (60) and small caliber ventilation gas delivery circuit (20) include a lumen or valve inflation/deflation channel (82) to operate the valve. An inflatable valve is preferably fabricated of an elastomeric material, such as silicone, and with a wall thickness of 0.002-0.010 inches. An inflatable valve preferably requires ¼-5 psi to inflate it and seal it against the valve seat. The valve's resting shape is close to the deflated shape, thus requiring pressurization and elongation of the material to inflate it to its use dimension. During normal operation of the ventilation system, the valve is inflated. In the event an obstruction or over-pressure condition occurs, the valve is deflated, and the patient can inspire and exhale through the tracheostomy tube to ambient air through the ambient flow ports (46). In the illustrated embodiment, the ventilator (V) comprises a mechanism to inflate and deflate the inflatable relief valve; a means to measure the pressure in the lung, and/or to detect overpressure in the lung, typically comprising a pressure transducer (90); and preferably a processor (170) to accept and process signals regarding the status of the system and the patient and to issue commands to control the ventilator and the relief valve. The valve deflation mechanism can be, for example, an inflation/deflation mechanism (92), such as a vacuum pump, which can be activated to deflate the valve upon command from the processor (170) after the processor has received a signal from the pressure measuring or detecting means that the lung pressure has exceeded a desired positive or negative limit. The vacuum pump can be used for both deflation (vacuum) and inflation (pressure) of the inflatable valve by connecting the inlet and outlet sides of the pump to a valve and controlling the valve accordingly. Or the pump can be switched so that the output attached to the inflation/deflation channel can switch from vacuum to pressure, based on the signal from the control system. The amount of gas required to inflate the inflatable diaphragm is preferably 0.2-5 ml under pressure, and more preferably 1-3 ml under pressure.

Alternatives to a vacuum pump can be used as an inflation/deflation mechanism (92) for inflating and deflating the relief valve. For example, the mechanism can be a mechanical apparatus, such as a spring loaded piston mechanism (98), such as is illustrated in cross section in FIG. 18C. The mechanism includes a piston (99), which moves in and out of a cylinder housing (164), such that the air in the cylinder chamber (163) compresses or decompresses the air in the valve inflation/deflation channel (82), which leads to the inflatable valve element (80) to inflate or deflate the valve. The spring loaded piston mechanism (98) includes a piston flange (161) and a piston stop (162), and a return spring (160). To inflate the inflatable valve element (80), an actuator (not shown) pushes the piston (99) away from the piston stop (162) in a direction into the cylinder housing (164) to pressurize the cylinder chamber (163) and valve inflation/deflation channel (82) and thus inflate the inflatable valve element (80). The relief valve may preferably be inflated during normal operation of the open ventilation system, so that the patient predominantly breathes through their natural upper airway. However, if an obstruction or high pressure condition is detected by way of monitoring airway pressure or breathing, the piston actuator is commanded to allow the piston move in a direction out of the cylinder housing (164) to depressurize the cylinder chamber (163) and valve inflation/deflation channel (82) and thus deflate the inflatable valve element (80), thereby allowing the patient to inspire and exhale through the tracheal tube (TT) to ambient air. In the system in FIG. 18C, the home position of the piston (99) is in a direction out of the cylinder housing (164), and the piston (99) only moves into the cylinder housing (164) while receiving a signal that the ventilator system is operating normally and/or the patient is breathing normally. Accordingly, the system in FIG. 18C would have the advantage that, in the case of ventilator malfunction, the piston will always stroke to its return home position, thus allowing the patient access to ambient air; thus, if the ventilator fails, the patient will have access to ambient air.

A pressure signal from the lungs may be received by the ventilator through the main gas delivery lumen of the transtracheal ventilation catheter (60) and small caliber ventilation gas delivery circuit (20), or through a dedicated pressure monitoring channel (not shown). The ventilator may alternatively or additionally measure lung pressure using a breathing signal from another breath sensor, such as one or more intratracheal breath sensors positioned on the catheter. Where breathing is sensed, the inflation/deflation mechanism (92) can be activated to deflate the valve upon command from the processor (170) after the processor has received a signal indicating that the patient's breathing has substantially slowed or stopped.

It should be noted that while the mechanism for inflating and deflating the inflatable relief valve preferably is controlled automatically by the ventilator and sensors, the ventilation system may also include a mechanism by which the inflation, deflation, or both inflation and deflation of the inflatable relief valve can be controlled manually by the patient or clinician. For example, the system can provide for manual inflation and automatic deflation, automatic deflation and manual inflation, manual inflation and manual deflation, or automatic deflation and automatic inflation. The system may alternatively provide providing both options of manually or automatically deflating and/or inflating. Manual inflation and deflation can be accomplished, for example, by a button that can be pushed on the ventilator, a syringe that can be actuated by the user, or a inflation and deflation bladder and valve that can be squeezed and pressurized and/or opened to ambient by the user. The same control options exist for other types of active relief valves.

FIGS. 19 and 20 each illustrates a portion of an alternative embodiment of an open ventilation system comprising an inflatable/deflatable active relief valve. In FIG. 19, a partial cross sectional view is shown in which the inflatable/deflatable valve (86) is part of the construction of the tracheostomy tube (TT) and is attached to the inside wall of the tracheostomy tube (TT). When deflated, the inflatable/deflatable valve (86) allows passage of gas between the transtracheal ventilation catheter (60) and tracheal tube (TT) and through the ambient flow ports (46) in the catheter connector (52). However, when inflated (as shown), the inflatable/deflatable valve (86) prevents passage of gas through the tracheal tube (TT), and thus the patient breathes ambient gas through their upper airway. In this case a portion of the valve inflation/deflation channel (82) is also part of the construction of the tracheal tube (TT). The channel can connect with the inflation/deflation mechanism (not shown) external to the tracheal tube through a length of tubing that can be either (a) part of the tracheal tube (TT), (b) part of the transtracheal ventilation catheter (60), or (c) a tube separate from the tracheal tube and catheter. In FIG. 20, a partial cross sectional view of a portion of an open ventilation system comprising an alternate inflatable active relief valve is shown. In this embodiment, the inflatable/deflatable valve (88) is part of the construction of the catheter connector (52) and is attached to the wall on the inner diameter of the catheter connector (52). When inflated, the inflatable/deflatable valve (88) expands inward to seal against the outside of the transtracheal ventilation catheter (60), thereby closing or blocking the ambient flow ports (46) to gas flow. When deflated, the inflatable/deflatable valve (88) is against the inner diameter of the connector, thus opening the ambient flow ports (46) to gas flow. The valve inflation/deflation channel (82) communicates with the inflatable/deflatable valve (88) to inflate or deflate the valve.

FIG. 21 illustrates a cross section of a portion of another alternative embodiment of an open ventilation system comprising an inflatable/deflatable valve (88). The valve is part of the construction of the catheter connector (106). When inflated, the valve closes the ambient relief port (46); and, when deflated, the valve opens the ambient relief port (46). The valve inflation/deflation channel (82) inflates or deflates the valve. A sensing channel (110), which communicates with a pressure transducer in the ventilator, may be placed through the catheter connector (106) and terminates at a sensing port at the distal end of sensing channel (110) to measure pressure, using the pressure transducer, in the annular space between the tracheal tube (TT) and the transtracheal ventilation catheter (60) to detect overpressure or under-pressure conditions in the airway and lung. If over- or under-pressure conditions are detected, the processor will signal the deflation mechanism to deflate the valve, so that the patient can exhale or inspire through the ambient flow ports (46). Alternatively, the pressure monitoring of the airway can be performed by measuring pressure in the gas delivery channel of the transtracheal ventilation catheter (60); by measuring pressure in a secondary channel within in the transtracheal ventilation catheter (60), which secondary channel extends beyond the catheter gas exit port by extending the secondary channel further into the tracheal tube (TT); or with an intra-tracheal sensor comprising an active sensing element integral to the transtracheal ventilation catheter (60) construction. If using pressure sensing lumens, such as when measuring pressure in the gas delivery channel of the catheter or measuring pressure in a secondary channel within in the catheter, a purge flow (114) is preferably created by a flow source in the ventilator, and the purge flow (114) preferably maintains patency of the sensing lumen.

FIGS. 22A-22D, provide exemplary graphs that illustrate conditions in the airway and lung that would trigger the operation of relief valves according to the present invention. The graphs show a breath sensor signal representing the pressure in the lung, airways, and/or trachea. Inspiratory (IP) pressure is indicated below the x axis and expiratory (EP) pressure is indicated above the x axis. The x axis represents time. FIG. 22A shows a normal spontaneous breathing pressure curve (120) is seen prior to an obstruction that occurs at time (500). After the obstruction that occurs at time (500), i.e., while the patient is suffering from the obstruction, FIG. 22A shows a spontaneous breathing pressure curve (122) that has reduced inspiratory amplitude. The loss or reduction of airflow or pressure can be a result of reduced respiratory drive, or can be a result of obstruction, thus retarding airflow. In ventilation systems according to the present invention, one or more relief valve is opened when obstruction or reduction in respiratory drive occurs or if it persists for a period of time. Alternatively, as shown in FIG. 22B, an obstruction can cause an increased negative pressure, as seen in the increased spontaneous inspiratory vacuum curve (126) as would be caused by an increased inspiratory effort to inspire air. Then, as pressure builds up in the lungs, an elevated expiratory pressure develops, as seen in the increased spontaneous expiratory pressure curve (124). Alternatively, as shown in FIG. 22C, an obstruction (occurring at time 500) can cause increased inspiratory effort as described by the increased spontaneous inspiratory vacuum curve (126). Alternatively, as shown in FIG. 22D, an obstruction (occurring at time 500) can cause an increase in lung pressure due to the trapping of gas in the lung as seen by the increased spontaneous expiratory pressure curve (124). In any case, drifts and slope changes in the respiratory signal, or amplitude swings of the respiratory signal caused by intensified effort to inspire across the obstruction, or breath trapping due to obstructions not allowing complete exhalation, are indicative that something is wrong with the open ventilation system and an intervention—either inspiratory pressure/flow relief, or expiratory pressure/flow relief, or both—is required. In FIGS. 22A-22D, pressure is used as the respiratory signal; however use of pressure as the respiratory signal is exemplary only, and any form of respiratory signal or measurement that will detect an obstruction or reduced respiratory drive can be used. As non-limiting examples, intra-tracheal airflow sensors, chest impedance sensors, flow sensors, gas composition sensors, pulse oximetry, respiratory neural drive signals, and muscle activity sensors may be used to monitor respiration. In any case, once an obstruction or reduced respiratory drive is detected, opening of one or more relief valve in a ventilation system according to the present invention would restore the airway pressure and the representative signal to a more normal amplitude.

FIG. 23 illustrates a partial axial cross sectional view of a portion of an open ventilation system comprising an active inspiratory and expiratory relief valve (134). In previous embodiments described, the active relief valves illustrated are inflatable valves; however, other types of active valves can be used according to the invention. FIG. 23 shows an active valve mechanism consisting of a sliding valve diaphragm (132) that slides away from a seat (73) in order to open the valve and allow passage of gas through the ambient flow ports (46), which are located in seat (73). The sliding valve diaphragm (132) is pressed against the seat (73) when the valve is closed. The valve diaphragm is controlled and commanded to slide to the closed or opened position by a valve actuator (130), in this case depicted as an electromagnetic actuator. The actuator, can optionally be housed in a catheter connector (52), which also includes secondary ambient flow ports (56) for the passage of air. The actuator can be electrical, mechanical, electromechanical, or electromagnetic. For example a coil can be used to create a magnetic field to move the valve diaphragm, actual magnets can be used to move the diaphragm, or a mechanical armature can be used to physically contact and move the diaphragm. The valve diaphragm can be fabricated from, for example, a light weight metal alloy, such as aluminum, with a 2-10% iron content if the mechanism is electromagnetic. Alternatively, the valve diaphragm can be fabricated from an engineering plastic, such as a polyimide thermoplastic resin, such as sold under the trademark ULTEM with iron particles blended into the material. The valve seat is preferably a soft plastic, such as a silicone, in order for the valve diaphragm to seal more effectively.

FIG. 24 illustrates a partial axial cross sectional view of a portion of an open ventilation system comprising an active relief valve that receives a pilot pressure signal from a pilot pressure signal line (142), that seats a convoluted diaphragm (140) against a valve seat (136) to seal the valve closed. The pilot pressure signal can be a pressure delivered to the valve from the ventilator. Alternatively or in addition, as shown in FIG. 24, an airway pressure signal line (143) can be applied to the diaphragm from the airway pressure. When the pressure signal from the airway pressure signal line (143) is abnormal, the valve chamber (147) becomes unbalanced, and the diaphragm moves away from the valve seat so that air can flow between the seat and the diaphragm to ambient. Alternatively, if the pilot pressure signal line (142) detects an abnormal pressure in the chamber because of the pressure exerted on the convoluted diaphragm (140) from the airway pressure signal line (143), a sensor measuring the pressure in the pilot pressure signal line would signal a control system to evacuate air from the valve chamber (147), thus moving the diaphragm away from the seat and opening the valve to ambient. This principle can be applied for an inspiratory pressure relief valve or an expiratory pressure relief valve or both, with the requisite modifications, which will be clear to one skilled in the art provided with the disclosure herein.

FIGS. 25A-25E illustrate partial axial cross sectional views of different configurations of ventilation catheters that are placed into a tracheal tube, outer cannula, or guide, in a portion of an open ventilation system. Preferably, in order to maximize the annular cross sectional space between the catheter and tracheostomy tube, outer cannula, or guide, the catheter diameter is minimized. The maximized annular space minimizes the breathing resistance through that space. For example, catheters having an outer diameter of 2 mm to 6 mm are preferred; and catheters having an outer diameter of ideally 3 mm-4 mm are more preferred when placed in an tracheal tube having an inner diameter of 6-10 mm. The maximized annular space is desired so that, in the event breathing through this gap is needed, the patient can breathe more easily through this annular gap. However, where the annular space is large, it is desirable to stabilize the catheter within the tracheostomy tube, to prevent it from whipping, to maintain its proper orientation, and, if breath sensors are associated with the catheter, to prevent them from moving with the catheter to an undesirable position inside the tracheal tube. The transtracheal ventilation catheter (60) is positioned in the tracheal tube by connecting it to the tracheal tube (TT) with a catheter connector (61), which will typically include a relief valve, although a relief valve is not depicted in FIGS. 25A-25E. In FIG. 25A, the catheter is self-stabilizing due to stiffness of the catheter itself, which is achieved, for example, by constructing it with a material of 60-90 Shore A hardness, or by including a stiffening wire or strip within the catheter wall, so that it resists deflection when exposed to pressures of up to 5 psi. In FIG. 25B, the catheter is stabilized by non-obstructive and low resistance catheter centering members (508). Non-limiting examples of non-obstructive and low resistance centering members include wire baskets, filaments, spokes, or coils, made from stainless steel, nitinol, or thermoplastic material. The members should introduce a resistance of less than 10 cm $H_2O$/L/sec, and preferably less than 3 cm $H_2O$/L/sec. In FIG. 25C, the catheter is stabilized by the geometry of catheter itself. In this embodiment, the catheter has a radius Rc that is larger than the tracheostomy tube radius Rt, so that the catheter, when inserted, rides along the inner upper, or posterior, wall of the tracheostomy tube, and is hence stabilized there. In FIG. 25D, the catheter is stabilized by the geometry of catheter itself. In this embodiment, the catheter has a radius Rc that is smaller than the tracheostomy tube radius Rt, so that the catheter, when inserted, rides along the inner lower, or anterior, wall of the tracheostomy tube, and is hence stabilized there. FIG. 25E illustrates a ventilation catheter having a generally sinusoidal or spiral configuration along at least part of its length, wherein the topmost and bottommost portions of the curves in the catheter contact the inner wall of the tracheostomy tube and thereby stabilize the catheter.

FIGS. 26A-26D are partial axial cross sectional views of portions of open ventilation systems. FIGS. 26A-26D illustrate alternative positions of an ambient relief valve in an open ventilation system comprising a transtracheal ventilation catheter (60), a tracheal tube (TT), and a relief valve. Previous figures have shown the relief valve at the proximal end of the ventilation catheter or the proximal end of the tracheostomy tube as shown by the inspiratory/expiratory relief valve (51) in FIG. 26A; however, the relief valve can be positioned in other locations, such as in the mid section of the tracheal tube such as is shown in FIG. 26B or in the distal section of the tracheal tube such as is shown in FIG. 26C. Where more than one relief valve is used, such as where a separate inspiratory relief valve (49) and expiratory relief valve (50) are used, the valves may be positioned in different locations from one another, such as is shown in FIG. 26D.

FIG. 27 illustrates portions of an open ventilation system in which a transtracheal ventilation catheter (60) is inserted into the lumen of a tracheal tube (TT), in this case a cuffed tracheal tube, for administering open ventilation through the transtracheal ventilation catheter (60). If the tracheal tube cuff (4) is accidentally inflated, the upper airway is obstructed and the patient can not naturally inspire or exhale through the upper airway, nor can the patient breathe through the tracheal tube (TT) since the proximal end of the tracheal tube is blocked by the catheter connector (52). In order to prevent inadvertent inflation of the tracheal tube cuff (4), the cuff inflation line (152) is blocked by a inflation line plug (153), which can be a component of the ventilation catheter, a component of the ventilation gas delivery circuit, or a separate component. The plug can be a "smart" plug, sending a signal, such as a pneumatic signal or electrical contact signal, to the ventilator, such that the ventilator can sense if the plug is accidentally not connected or inadvertently disconnected to the cuff inflation line, and thus activating an alarm or other signal by sensing the lack of connection, through. Therefore, inadvertent inflation of the cuff is prevented by or detected by the plug. Or, alternatively, a cuff vacuum line (154) can be attached to the cuff inflation line, where the vacuum line is in communication with a vacuum source (102) in the ventilator, preferably through a channel integral to the gas delivery circuit assembly. This assures deflation of the cuff during administration of open ventilation, so that the patient is assured to be able to breathe spontaneously through the upper airway unless there is some other form of obstruction, in which case the previously described relief valves will be useful. Although relief valves are not illustrated in FIG. 27, relief valves as described herein may be used with this embodiment. The vacuum can be constantly or intermittently active, can be activated when an obstruction has been sensed by means previously described, or could be applied continuously or intermittently. Optionally, instead of or in conjunction with the vacuum source, a mechanism can be used to regulate and control both the inflation and deflation of the cuff, in order to switch between closed ventilation (fully inflated cuff) and open ventilation (fully deflated cuff), and/or partially open or closed ventilation (partially inflated cuff). Lung pressures can therefore be regulated during administration of ventilation therapy.

FIG. 28 illustrates partial axial cross sectional view of a portion of an open ventilation system in which the transtracheal ventilation catheter (60) is inserted into the lumen of a stoma stent (180), as shown, or a stoma guide. The stoma stent (180) is placed in a stoma, which is a percutaneous hole through the skin of the neck (184) and the tracheal wall (182). The stoma stent (180) includes a flange or petals against the outside of the neck (184) and against the inside anterior wall of the tracheal wall (182), to position the stoma stent (180) correctly in the stoma. The catheter connector (52), which positions and connects the transtracheal ventilation catheter (60) to the stoma stent (180), includes ambient flow ports (46); and the catheter includes an expiratory relief diaphragm (48) which seals the ambient flow ports (46) and stoma stent (180) in normal operation. In this embodiment, the relief valve is an expiratory relief valve only; however, with the requisite modifications, the relief valve can be an inspiratory relief valve or a combined expiratory and inspiratory relief valve, and can function as previously described.

FIGS. 29A-29C illustrate a portion of an open ventilation system, showing alternative configurations for a relief valve positioned between the transtracheal ventilation catheter (60) and stoma guide (181). The stoma guide (181) is different than the stoma stent (180) of FIG. 28 in that the stoma guide (181) protrudes a distance into the patient's tracheal lumen, whereas the stoma stent (180) is flush with the tracheal wall. The stoma guide (181) preferably protrudes to approximately the center of the tracheal lumen; however, the stoma guide (181) can protrude any distance. The stoma guide (181) is preferably curved in order to direct the catheter toward the lung. FIG. 29A illustrates a transtracheal ventilation catheter (60) inserted into a stoma guide (181) with a sealing connector (103) and an inflatable valve element (80). FIG. 29B illustrates a sealing connector (104) between the transtracheal ventilation catheter (60) and stoma guide (181). In FIGS. 29A and 29B, the sealing connector (103, 104) seals the annular space between the stoma guide and catheter so that the patient can not breathe through the stoma guide (181); however, the sealing connector (103, 104) can be manually removed by the patient or clinician if the patient is suffering from an obstruction, or can be configured and arranged so that it automatically pops off in the event of an overpressure condition. In the embodiment of FIG. 29B, the transtracheal ventilation catheter (60) also includes a catheter connector (52) having ambient flow ports (46) therethrough. When the sealing connector (104) is removed or pops off, the ambient flow ports (46) in the catheter connector (52) are opened to atmosphere and the patient can now breathe ambient air through the stoma guide. In the embodiment of FIG. 29A, an active valve, such as inflatable valve element (80), can then perform the functions of pressure and flow relief as described previously in conjunction with active relief valves. FIG. 29C illustrates a sealing connector (105) that includes ambient flow ports 46 therethrough and an expiratory relief diaphragm (48). Sealing connector (105) is removably attached to the stoma guide (181). In this embodiment, the transtracheal ventilation catheter (60) is placed through the sealing connector (105) and expiratory relief diaphragm (48), such as through hole in the sealing connector (105) and a slit in a expiratory relief diaphragm (48). FIG. 29C shows an expiratory relief valve; however, the embodiment of an insertable catheter through the valve and sealing connector can exist also with a expiratory valve or a combined inspiratory/expiratory valve, and with passive valves as well as active valves. The embodiments described in FIGS. 29B and 29C allow the user to remove the entire transtracheal ventilation catheter (60) from the airway and discontinue the open ventilation therapy, during which time the user will have the option to seal the stoma guide (181) using sealing connector (104, 105) or open the stoma guide, (181) depending on the preferences and clinical situation.

Each of FIGS. 30A-30I illustrates the relief valve portion of an open ventilation system. These figures show additional non-limiting examples of types of relief valves that may be used in accordance with the present invention. FIG. 30A illustrates a disk valve (210), FIG. 30B a diaphragm valve (212), and FIG. 30C a convoluted diaphragm (214), which is biased to open more easily in a desired direction by design of the convolution which amplifies the force applied to the diaphragm. As in the embodiment shown in FIG. 30C, the convoluted diaphragm can be a compound convolution, which is convoluted in one direction to open in one direction for inspiratory pressure relief and also convoluted in the opposite direction to open in the opposite direction for expiratory pressure relief. FIG. 30D illustrates a poppet valve (216), FIG. 30E a duck billed valve (218), FIG. 30F a spring loaded check valve comprising a spring (220) and spring valve (222), and FIG. 30G an umbrella diaphragm valve (224). FIGS. 30H and 30I describe a swing valve with a hinge; FIG. 30I describes the swing valve in partial cross section. The a valve comprises a valve leaflet (228), a leaflet valve seal (230), and ambient flow ports (46). FIG. 30I describes an end view of the valve showing the leaflet valve hinge (226) for the valve leaflet (228). Each of these types of valves, as well as other suitable art-known valves, and combinations thereof, can be used with any embodiments of the invention. Additional non-limiting types of valves that may be used with the present invention include film check valves, poppet check valves, duck billed check valves, umbrella check valves, swing check valves, spring check valves, diaphragm check valves, magnet check valves, sliding armature check valves, inflatable valves, deflatable relief valves, inflatable/deflatable valves, spring loaded valves, valves with electromechanical actuators, electromagnetic valves, and combinations thereof. Valves useful in embodiments of the present invention include one-way valves, such as valves that are one-way valve in the direction of inspiration and valves that are one-way in the direction of exhalation; two-way valves, such as valves that open both in the direction of inspiration and in the direction of exhalation; and combinations thereof.

The cracking pressure of expiratory relief valves or diaphragms used in embodiments of the present invention can preferably be 1-50 $cmH_2O$ pressure, more preferably 5 to 50 $cmH_2O$, even more preferably 10 to 40 $cmH_2O$, even more preferably 5 to 30 $cmH_2O$, even more preferably 20 to 25 $cmH_2O$, and most preferably 8 to 12 $cmH_2O$. The cracking pressure of inspiratory valves or diaphragms used in embodiments of the present invention can preferably be −5 to −50 $cmH_2O$, more preferably −10 to −40 $cmH_2O$, more preferably −10 to −20 $cmH_2O$, and most preferably −6 to −15 $cmH_2O$. The cracking pressure can also be adjustable by a clinician or patient, for example by tightening the valve against the seat. The ventilator can also be adapted to automatically adjust the cracking pressure of valves and diaphragms in response to breathing effort or breathing pressure information obtained by sensor(s).

Further, various combinations of active and passive valves, and inspiratory relief valves and expiratory relief valves may be used in accordance with the present invention. As non-limiting examples, an active inspiratory relief valve may be used with a passive expiratory relief valve; a passive inspiratory relief valve may be used with an active expiratory relief valve; an active inspiratory relief valve may be used with a passive inspiratory relief valve; an expiratory relief valve may be used with a passive expiratory relief valve; and other combinations may be used, including using three or more valves in combination. An combination of valves may be referred to as a "valve" or as a "respiratory relief device" or "respiratory relief devices". Valve(s) may also be used in combination with ambient flow ports and/or breathing circuit ambient flow ports. Combinations of valve(s) and ambient flow ports and/or breathing circuit ambient flow ports may be referred to as a "respiratory relief device" or "respiratory relief devices". Valves may also be configured so that they may be manually opened or closed by a patient or clinician. The present invention includes both valves for which manual opening and closing is the only method of operation; as well as valves that open or close passively or actively in response to a selected condition or occurrence, but that can also be opened or closed manually.

FIG. 31 graphically illustrates the operation of an additional embodiment of the invention, specifically an open ventilation system similar to previous embodiments, however comprising an apnea mode, or back up rate mode, and an active relief valve. To accomplish this, the ventilator comprises a control system to receive information from respiration sensors and to control the back up rate mode and the active relief valve. Respiration sensors are used to measure spontaneous breathing and pressure in the airway and lung and to provide that information to the ventilator control system. The apnea or back up rate mode of the ventilator is used to supplement or replace the patient's spontaneous ventilation when it has been reduced due to an obstruction or reduced respiratory drive, so the patient receives enough ventilation. At least one relief valve is used to prevent over pressurization of the lung by the ventilator when operating in back up mode, which could otherwise increase lung pressure due to breath stacking and inadequate evacuation of the gas. The apnea mode of the ventilator, as well as opening of the relief valve, is activated when breath sensors detect a loss of or reduction in respiration, a loss of or reduction in tracheal airflow, or a shift in lung pressure indicating an obstruction or restriction of the patient's airway. The signal from the breath sensor is received by the ventilator processing unit or control system, and, based on predetermined criteria or algorithms, or by real-time deterministic criteria, the control system will activate the back up mode and/or the relief valve opening. The back up rate mode and active relief valve can be adjusted during the course of the obstruction or apneic event, based on knowledge of the patient's condition using the information from the respiration sensor(s), so that the proper lung and ventilation conditions are achieved by the back up rate and relief valve. When the desired conditions are restored, based on preset criteria and algorithms, the back up mode is disabled, and the relief valve is closed.

Referring to the graphs of FIG. 31, in which the x axis represents time, an obstruction occurs at time (500), a back up apnea ventilator rate (or "apnea mode" or "back up rate mode") begins at time (502), and the relief valve opens at time (504), however, the relief valve opening can occur before the back up apnea ventilator rate beginning in other examples. During the time preceding the obstruction (occurring at time 500), the relief valve is closed, the breath sensor signal indicates a normal amplitude for a spontaneous inspiration and exhalation, in this case graphed as tidal volume per breath, the ventilator output signal indicates that the ventilator is delivering the prescribed volume or pressure delivery per breath, and the lung pressure indicates a normal inspiratory and expiratory lung pressure expected in an open ventilation system. The time period succeeding the obstruction (occurring at time 500), graphically indicates the response of the apnea mode, the relief valve, and the effect these interventions have on tidal volume and lung pressure. When in the apnea mode, (beginning at time 502), the ventilator operates with a back up ventilation rate, in which the ventilator starts to deliver ventilation volumes at an automatic rate, rather than in response to a patient inspiratory effort. The rate of gas delivery in apnea mode is preferably 1-5 times the normal spontaneous breath rate as determined by historical trending of the patient, or by clinical normal values, thereby delivering enough volume to compensate for the patient's reduction in spontaneous breathing. As an alternative to, or in addition to, a higher rate of gas delivery, the augmentation volume can be automatically increased in apnea mode to deliver enough volume to compensate for the patient's lack of spontaneous breathing. In addition to the back up rate, an active exhalation relief valve may be signaled to open when the lung pressure reaches a predetermined threshold, so that the back up augmentation rate and volume delivery doesn't cause dangerously high lung pressure. Specifically, if the reduction in respiration was caused by or partially caused by an obstruction, the back up rate may elevate lung pressure to an undesirable level, hence the relief valve will provide the required safety. Or, the back up rate frequency may not provide enough time to allow exhalation between ventilator cycles, which could cause a ramping up of lung pressure, in which case the relief valve will provide the required safety.

FIG. 32 illustrates an embodiment similar to the embodiment in FIG. 31, with the difference however that the relief valve is a passive relief valve in FIG. 31, instead of an active relief valve. The expiratory relief valve in FIG. 31 is a passive relief valve with a certain cracking pressure. In FIG. 32 an obstruction occurs at time (occurring at time 500), the back up apnea ventilator rate begins at time (502), and the passive relief valve opens at time (506). During the time preceding the obstruction (occurring at time 500), the graphs indicate normal tidal volume and normal lung pressure. The time succeeding the obstruction indicates a reduction in breathing tidal volume and a ramping up of lung pressure due to trapping of gas and incomplete exhalation. The relief valve opening indicates that the lung is prevented form a continued increase in pressure. Also shown in the graphs for contract and for reference purpose is a graph of lung pressure assuming there is no relief valve. In this case, the lung pressure continues to increase, potentially to unsafe levels, especially during the time that the ventilator back up rate is active.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The present invention may be embodied in other specific forms without departing from its spirit or essential characteristics. Such additional embodiments and forms will be clear to one skilled in the art provided with the disclosure herein. The described embodiments are to be considered in all respects only as illustrative and not restrictive. For example, often in the foregoing descriptions the catheter is described to be positioned in a tracheostomy tube or tracheal tube, terms that are used interchangeably. However, the catheter can be placed in other types of transtracheal cannulae or prostheses that provide an access port to the trachea. Non-limiting examples of such devices include such as an airway guides, catheter guides, tracheal prostheses, stoma guides, stents, outer cannulae, airway prostheses, and other guiding structures. As another example, the ventilation delivery system is typically described as comprising a transtracheal ventilation catheter; however, the ventilation delivery system can comprise other types of tubes or cannula, and/or can enter the airway from other sites/in other manners besides transtracheally. As yet another example, combinations of different types of valves can be used; as non limiting examples, a passive inspiratory valve may be used in combination with an active expiratory relief valve; or, conversely, an active inspiratory relief valve can be used in combination with a passive expiratory relief valve. As still another example, a valve that provides both passive and active inspiratory pressure relief may be used. As a still further example of variations that may be made without departing from the present invention, the relief valve(s) are described herein as part of a transtracheal ventilation tube or catheter, but it should be understood that the invention applies to patient interfaces introduced into the body in other locations, such as trans-cricothyrotomy tubes, upper airway tubes, endotracheal tubes and catheters, and oro-nasal ventilation tubes and catheters. For simplicity, portions of the ventilation gas delivery catheter are often depicted in the figures as a side view showing only the outside surface of the catheter without showing the gas delivery lumen or walls of the catheter.

It should also be noted that in the described embodiments, the relief valves are typically described as having two states, an opened state and a closed state. However, other states can exist, such as partially opened states. Relief valves in partially opened states may be used, for example, to control lung pressure at a desired level, such as maintaining 5 cmH₂O lung pressure during exhalation phase.

Although a ventilator (V) is not always explicitly illustrated or described with relation to all embodiments described herein, the embodiments of the present invention are generally used in conjunction with a ventilator (V). The embodiments of the present invention may be used with any suitable ventilator, non-limiting examples of which include stationary ventilators, ventilators suitable for use in vehicles, ventilators suitable for home use, ventilators sized for a patient to carry or wheel on a cart, wearable ventilators, and central respiratory systems, such as those in medical facilities.

Also, while the invention is described to treat respiratory insufficiency and airway or breathing disorders, it can also be applied to any ventilation therapies or interventions such as anesthesia delivery, drug delivery to name a few.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:

1. A ventilation apparatus comprising
   (a) a ventilator adapted to
      (i) provide a pulse of gas to the patient during inspiration by a patient, wherein the pulse has a first volume; and
      (ii) provide pulses of gas to a patient after detection of a cessation of breathing or reduction in breathing volume of the patient, wherein the pulses each have a second volume and wherein (1) the pulses are provided at a rate that is 1-5 times the normal breathing rate, (2) the second volume is 25-500% greater than the first volume, or (3) the pulses are provided at a rate that is 1-5 times the normal breathing rate and the second volume is 25-500% greater than the first volume;
   (b) a gas delivery circuit operably connected to the ventilator;
   (c) one or more respiratory sensor adapted to determine when the patient inspires, to calculate a normal breathing volume for the patient, to detect a cessation of breathing or reduction in breathing volume of the patient; and
   (d) a respiratory relief device, wherein the respiratory relief device is configured to allow the patient to exhale to atmosphere;
   (e) a pressure transducer to measure the pressure in the lungs, to detect overpressure in the lungs, or both; and
   wherein the respiratory relief device comprises an active valve.

2. The ventilation apparatus of claim 1, wherein the respiratory relief device comprises a seat and a diaphragm; wherein the valve receives a pilot pressure signal from the lungs or from the ventilator, and wherein the pilot pressure signal regulates the position of the diaphragm against the seat.

3. The ventilation apparatus of claim 1, wherein the respiratory relief device has an open state and a closed state.

4. The ventilation apparatus of claim 3, wherein the respiratory relief device is adapted to be provided in a closed state while the one or more respiratory sensor detects that the patient is breathing within the normal breathing rate, normal lung pressure, normal airway pressure, or a combination thereof.

5. The ventilation apparatus of claim 3, wherein the one or more respiratory sensor is adapted to detect a variation in the patient's breathing rate from the normal lung pressure, a variation in the patient's lung pressure from the normal lung pressure, a variation in the patient's airway pressure from the normal airway pressure, or a combination thereof.

6. The ventilation apparatus of claim 5, wherein the respiratory relief device is adapted to open or be opened in response to detection of the variation.

7. The ventilation apparatus of claim 1, further comprising:
   a ventilation catheter operably connected to the gas delivery circuit;
   wherein the pulses of gas are provided to the patient through the ventilation catheter.

8. The ventilation apparatus of claim 7, further comprising:
   a patient ventilation interface, wherein the ventilation catheter is placed coaxially in the patient ventilation interface; and wherein the patient ventilation interface and the ventilation catheter are arranged such that a patient using the ventilation apparatus can breathe freely through the patient's upper airway.

9. The ventilation apparatus of claim 1, wherein the respiratory relief device comprises an active valve.

10. The ventilation apparatus of claim 1, wherein the respiratory relief device comprises a seat and a diaphragm; wherein the respiratory relief device receives a pilot pressure signal from the lungs or from the ventilator, and wherein the pilot pressure signal regulates the position of the diaphragm against the seat.

11. A method of providing ventilation to a patient comprising
   (a) using one or more respiratory sensor to determine when the patient inspires;
   (b) providing a pulse of gas to the patient during inspiration by the patient, wherein the pulse has a first volume;
   (c) using the one or more respiratory sensor to calculate a normal breathing volume for the patient;
   (d) providing a respiratory relief device, wherein the respiratory relief device is configured to allow the patient to exhale to atmosphere;
   (e) detecting a cessation of breathing or reduction in breathing volume of the patient;
   (f) after detecting a cessation of breathing or reduction in breathing volume of the patient, providing pulses of gas to the patient, wherein the pulses each have a second volume and wherein (i) the pulses are provided at a rate that is 1-5 times the normal breathing rate, (ii) the second volume is 25-500% greater than the first volume, or (iii) the pulses are provided at a rate that is 1-5 times the normal breathing rate and the second volume is 25-500% greater than the first volume;
   (g) using a pressure transducer to measure the pressure in the lungs, to detect overpressure in the lungs, or both; and
   (h) opening the respiratory relief device when overpressure in the lungs is detected.

12. The method of claim 11, further comprising:
   using the one or more respiratory sensor to measure the patient's breathing rate;
   using the one or more respiratory sensor to calculate a normal breathing rate for the patient;
   providing the respiratory relief device in a closed state while the one or more respiratory sensor detects that the patient is breathing within the normal breathing rate;
   using the one or more respiratory sensor to detect a variation in the patient's breathing rate from the normal breathing rate; and opening the respiratory relief device in response to detection of the variation in the patient's breathing rate from the normal breathing rate.

\* \* \* \* \*